(12) United States Patent
Bramlet et al.

(10) Patent No.: US 6,695,844 B2
(45) Date of Patent: Feb. 24, 2004

(54) SURGICAL FASTENER ASSEMBLY

(75) Inventors: Dale G. Bramlet, St. Petersburg, FL (US); Peter Sterghos, St. Petersburg, FL (US); John Sodeika, Clearwater, FL (US)

(73) Assignee: Orthopedic Designs, Inc., St. Petersburg, FL (US)

( * ) Notice: Subject to any disclaimer, the term of this patent is extended or adjusted under 35 U.S.C. 154(b) by 414 days.

(21) Appl. No.: 09/729,243

(22) Filed: Dec. 5, 2000

(65) Prior Publication Data

US 2001/0000186 A1 Apr. 5, 2001

Related U.S. Application Data

(60) Division of application No. 09/239,862, filed on Jan. 29, 1999, now Pat. No. 6,183,474, which is a continuation-in-part of application No. 08/680,620, filed on Jul. 17, 1996, now Pat. No. 5,976,139, and a continuation-in-part of application No. 08/615,022, filed on Mar. 13, 1996, now Pat. No. 5,984,970.

(51) Int. Cl.[7] ............................................. A61B 17/76
(52) U.S. Cl. ............................. 606/66; 606/65; 606/69
(58) Field of Search ...................................... 606/60–73

(56) References Cited

U.S. PATENT DOCUMENTS

| | | |
|---|---|---|
| 3,462,765 A | 8/1969 | Swanson |
| 3,593,342 A | 7/1971 | Niebauer et al. |
| 3,791,380 A | 2/1974 | Dawidowski |
| 3,798,679 A | 3/1974 | Ewald |
| 3,805,302 A | 4/1974 | Mathys |
| 3,848,276 A | 11/1974 | Martinez |
| 3,875,594 A | 4/1975 | Swanson |
| 3,879,767 A | 4/1975 | Stubstad |
| 3,886,600 A | 6/1975 | Kahn et al. |
| 3,899,796 A | 8/1975 | Bahler et al. |
| 3,946,445 A | 3/1976 | Bentley et al. |
| 3,986,212 A | 10/1976 | Sauer |
| 3,990,116 A | 11/1976 | Fixel et al. |
| 3,991,425 A | 11/1976 | Martin et al. |
| 3,992,726 A | 11/1976 | Freeman et al. |
| 4,011,603 A | 3/1977 | Steffee |
| 4,059,854 A | 11/1977 | Laure |
| 4,150,444 A | 4/1979 | Hagert |
| 4,158,893 A | 6/1979 | Swanson |
| 4,175,555 A | 11/1979 | Herbert |
| 4,193,139 A | 3/1980 | Walker |
| 4,231,121 A | 11/1980 | Lewis |
| 4,242,759 A | 1/1981 | White |

(List continued on next page.)

FOREIGN PATENT DOCUMENTS

| | | |
|---|---|---|
| EP | 0 619 982 A2 | 10/1994 |
| EP | 0 636 346 A1 | 2/1995 |
| FR | 2 651 119 | 3/1991 |
| WO | 8 801 854 | 3/1988 |
| WO | WO 98/02105 | 1/1998 |

Primary Examiner—David O. Reip
(74) Attorney, Agent, or Firm—Kenyon & Kenyon

(57) ABSTRACT

A surgical fastener assembly for coupling first and second bone portions across a fracture therebetween is disclosed. In one embodiment of the present invention, the surgical fastener assembly includes an anchor that has a first externally threaded portion disposed in the first bone portion and a second portion which is at least partially disposed in the second bone portion. At least one pin is operably associated with the first portion of the anchor such that when the pin is in a retracted position the pin is disposed within the anchor and when the pin is in an extended position at least a portion of the pin extends outward from the anchor. An actuator is disposed within the anchor and is operably coupled with the at least one pin. A guide is adapted to be fixedly secured to the second bone portion and includes a sleeve. The second portion of the anchor is received within the sleeve. A fastener is provided that has a head portion and an externally threaded shank portion. The shank portion threadedly engages with the anchor and the head portion operably engages with the guide.

14 Claims, 35 Drawing Sheets

U.S. PATENT DOCUMENTS

| | | |
|---|---|---|
| 4,267,608 A | 5/1981 | Bora, Jr. |
| 4,313,232 A | 2/1982 | Habal et al. |
| 4,352,212 A | 10/1982 | Greene et al. |
| 4,375,703 A | 3/1983 | Evans et al. |
| 4,467,479 A | 8/1984 | Brody |
| 4,470,158 A | 9/1984 | Pappas et al. |
| 4,632,101 A | 12/1986 | Freedland |
| D291,731 S | 9/1987 | Aikins |
| 4,725,280 A | 2/1988 | Laure |
| 4,759,768 A | 7/1988 | Hermann et al. |
| 4,787,908 A | 11/1988 | Wyss et al. |
| 4,898,156 A | 2/1990 | Gatturna et al. .............. 606/72 |
| 4,911,719 A | 3/1990 | Merle |
| 4,944,758 A | 7/1990 | Bekki et al. |
| 4,946,468 A | 8/1990 | Li ............................... 606/232 |
| 4,968,315 A | 11/1990 | Gatturna ..................... 606/72 |
| 4,969,909 A | 11/1990 | Barouk |
| 5,002,550 A | 3/1991 | Li ............................... 606/139 |
| 5,007,910 A | 4/1991 | Anapliotis et al. ........... 606/65 |
| 5,041,116 A | 8/1991 | Wilson ........................ 606/65 |
| 5,046,513 A | 9/1991 | Gatturna et al. ............. 128/898 |
| 5,057,103 A | 10/1991 | Davis .......................... 606/63 |
| 5,062,851 A | 11/1991 | Branemark |
| 5,092,896 A | 3/1992 | Meuli et al. |
| 5,108,443 A | 4/1992 | Branemark |
| 5,133,761 A | 7/1992 | Krouskop |
| 5,147,386 A | 9/1992 | Carignan et al. |
| 5,171,284 A | 12/1992 | Branemark |
| 5,192,303 A | 3/1993 | Gatturna et al. ............. 606/232 |
| 5,207,679 A | 5/1993 | Li ............................... 606/72 |
| 5,207,712 A | 5/1993 | Cohen |
| 5,217,486 A | 6/1993 | Rice et al. ................... 606/232 |
| 5,290,314 A | 3/1994 | Koch et al. |
| 5,314,479 A | 5/1994 | Rockwood, Jr. et al. |
| 5,324,292 A | 6/1994 | Meyers ....................... 606/73 |
| 5,356,413 A | 10/1994 | Martins et al. ................ 606/75 |
| 5,478,342 A | 12/1995 | Kohrs ......................... 606/73 |
| 5,534,004 A | 7/1996 | Santangelo .................. 606/68 |
| 5,578,035 A | 11/1996 | Lin ............................. 606/68 |
| 5,591,168 A | 1/1997 | Judet et al. ................... 606/65 |
| 5,643,321 A | 7/1997 | McDevitt .................... 606/232 |

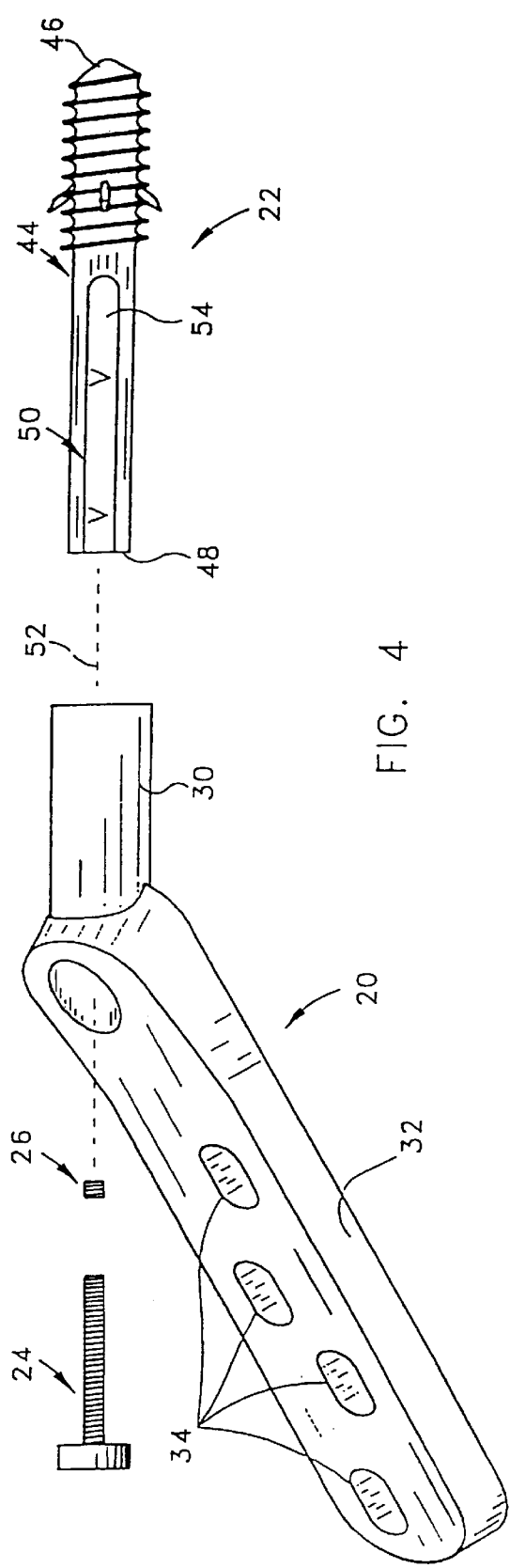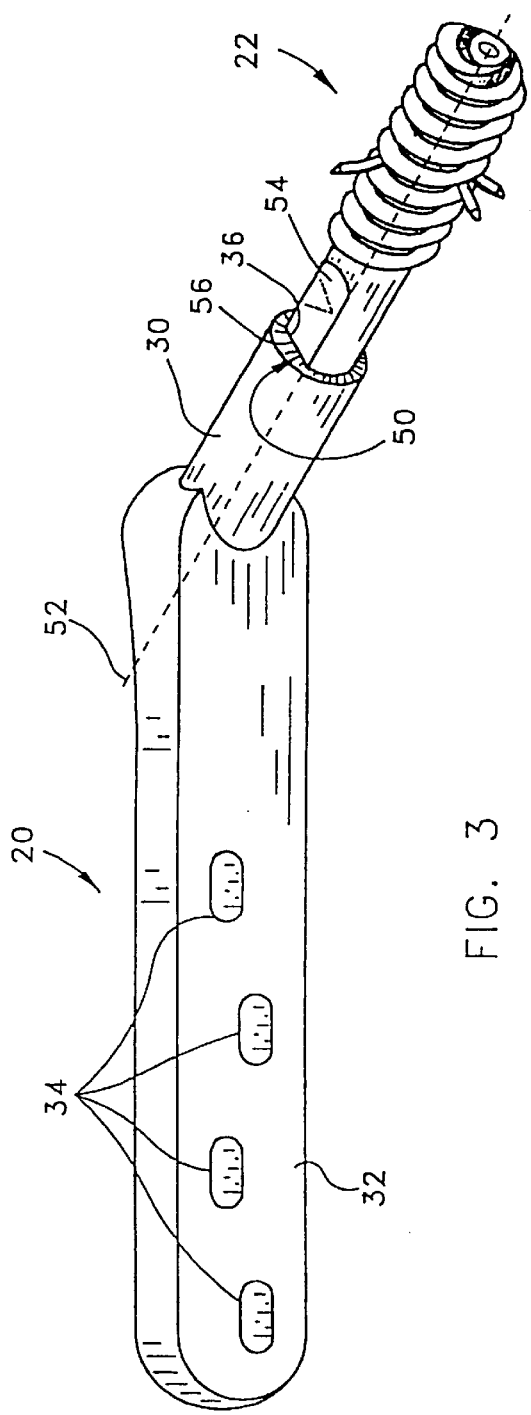
FIG. 4
FIG. 3

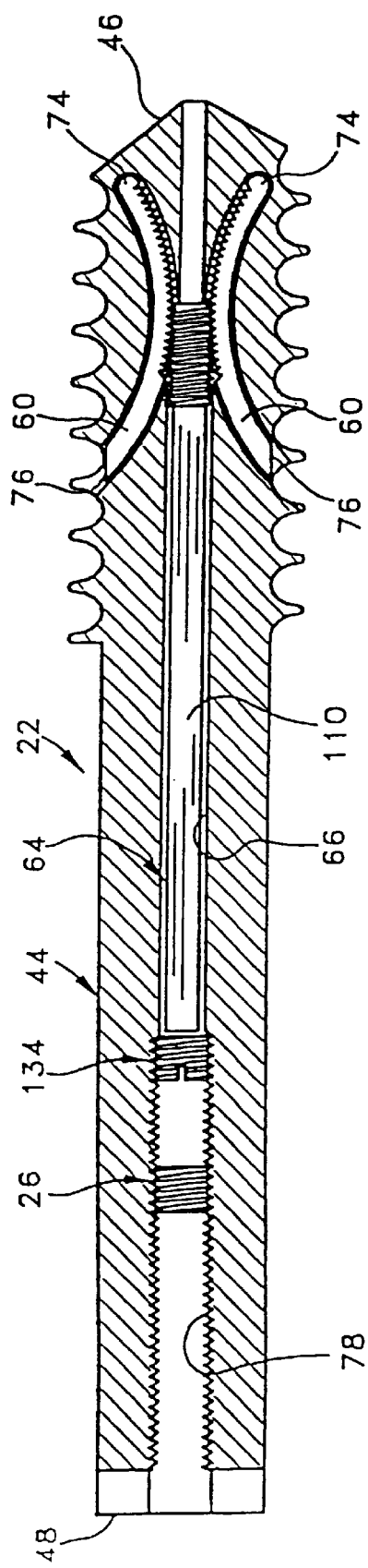
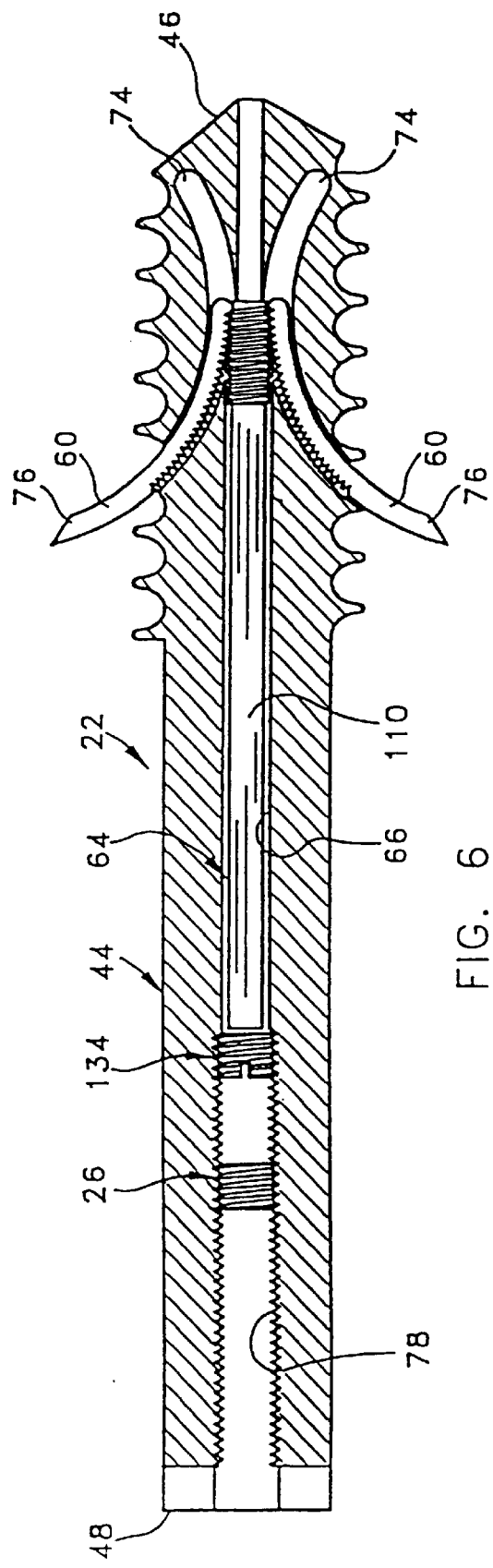
FIG. 5
FIG. 6

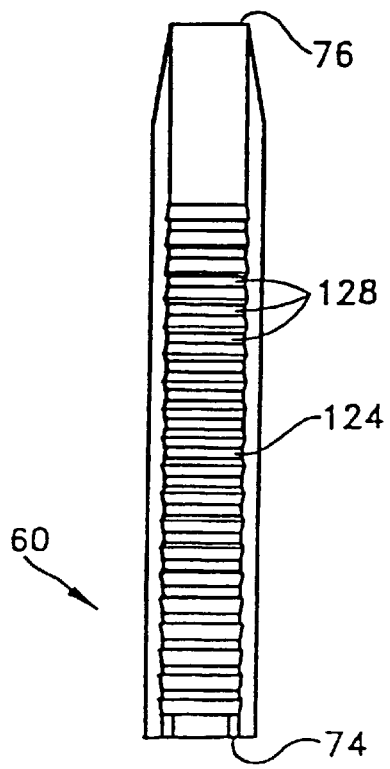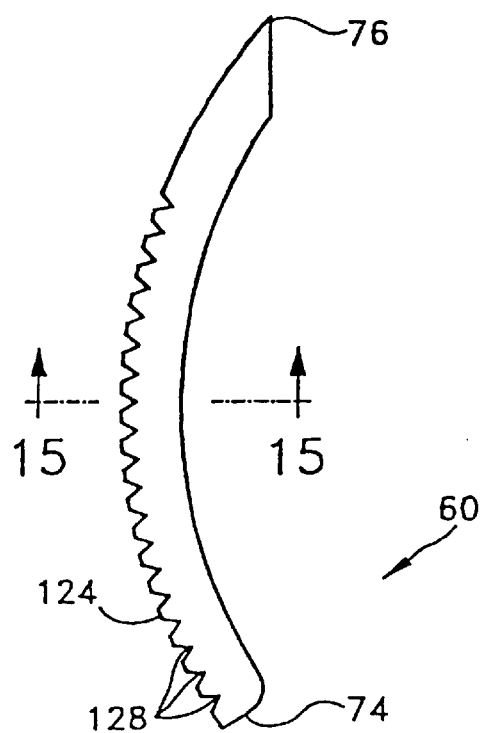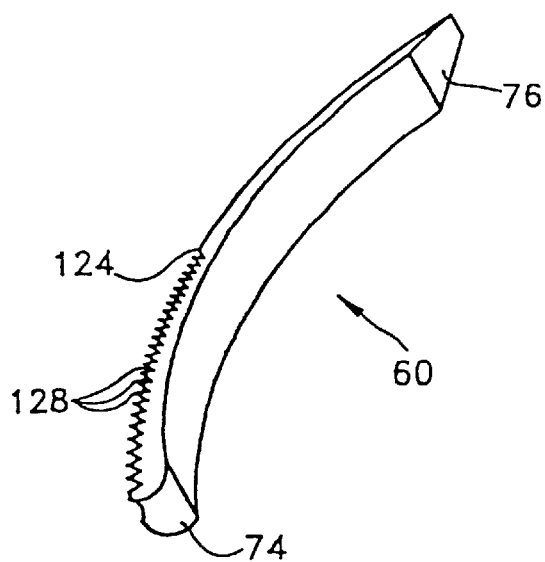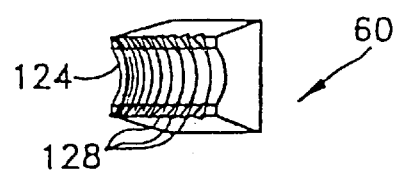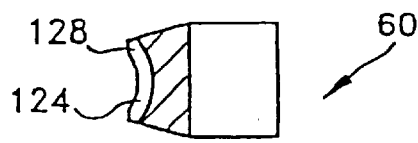
FIG. 13
FIG. 12
FIG. 14
FIG. 11
FIG. 15

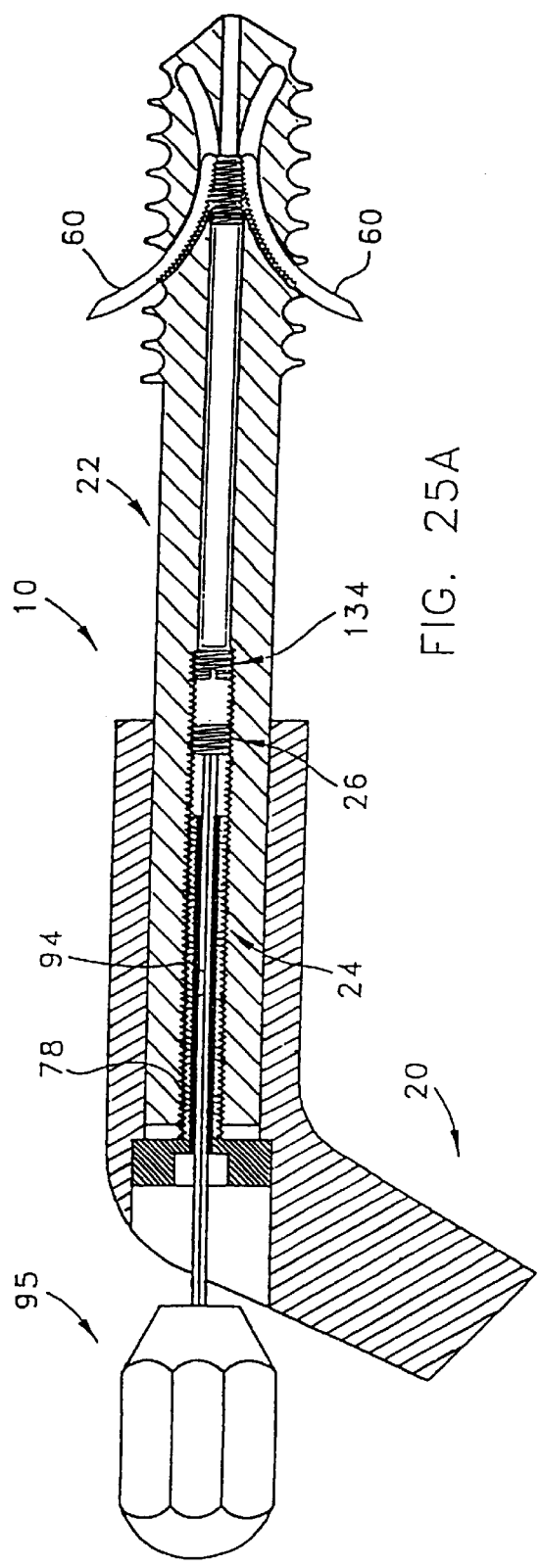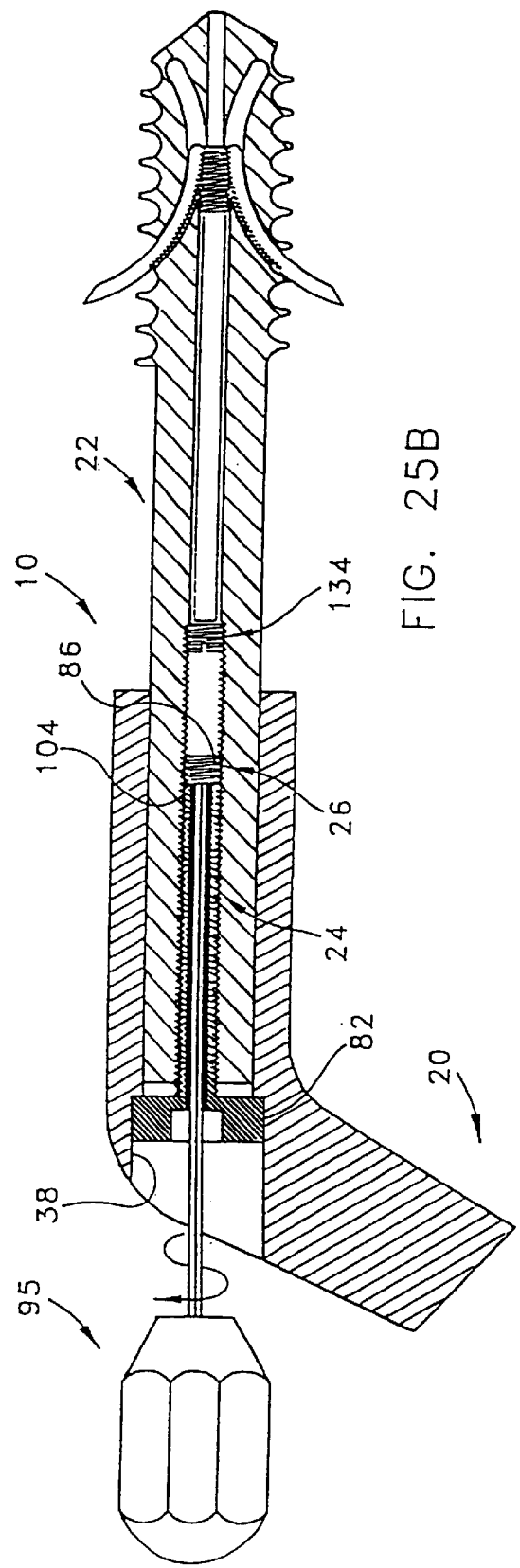

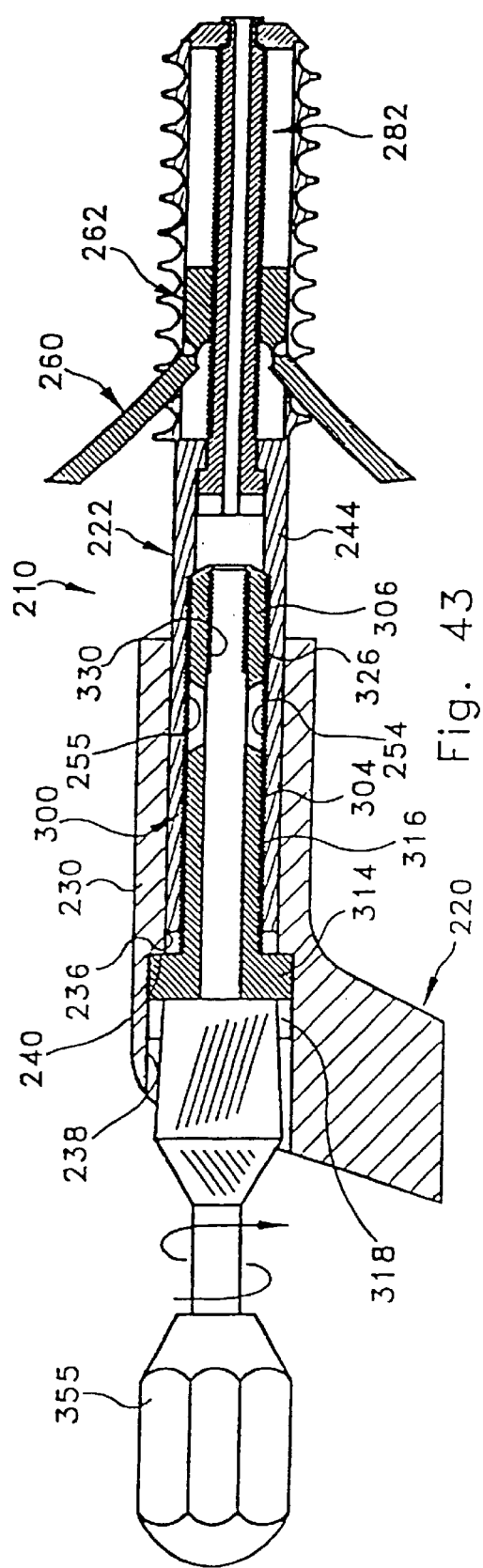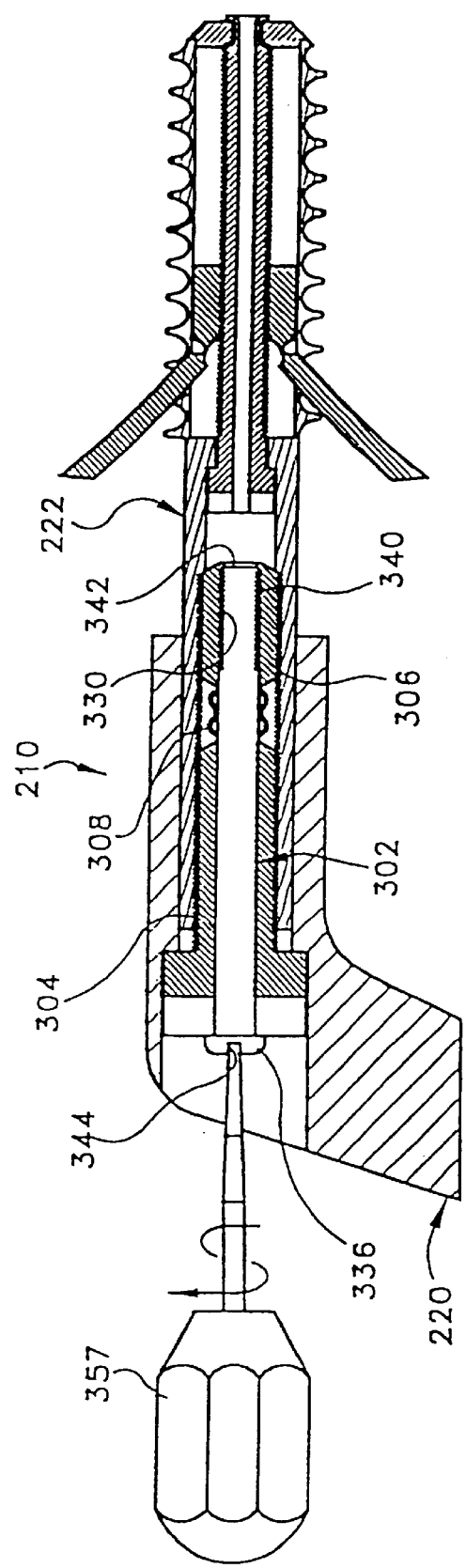

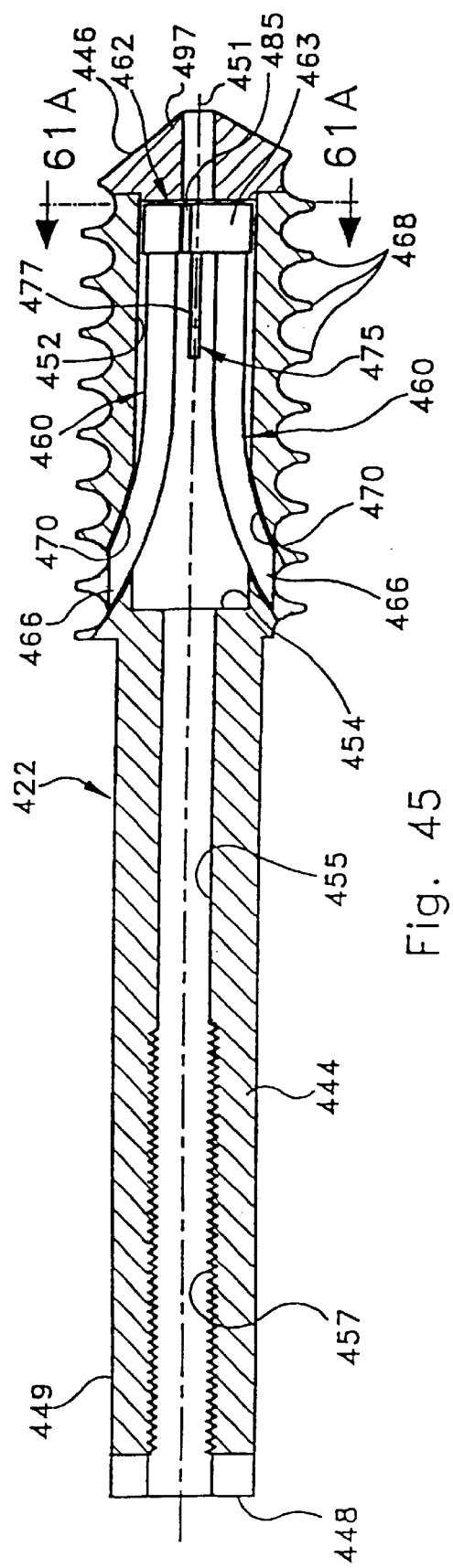
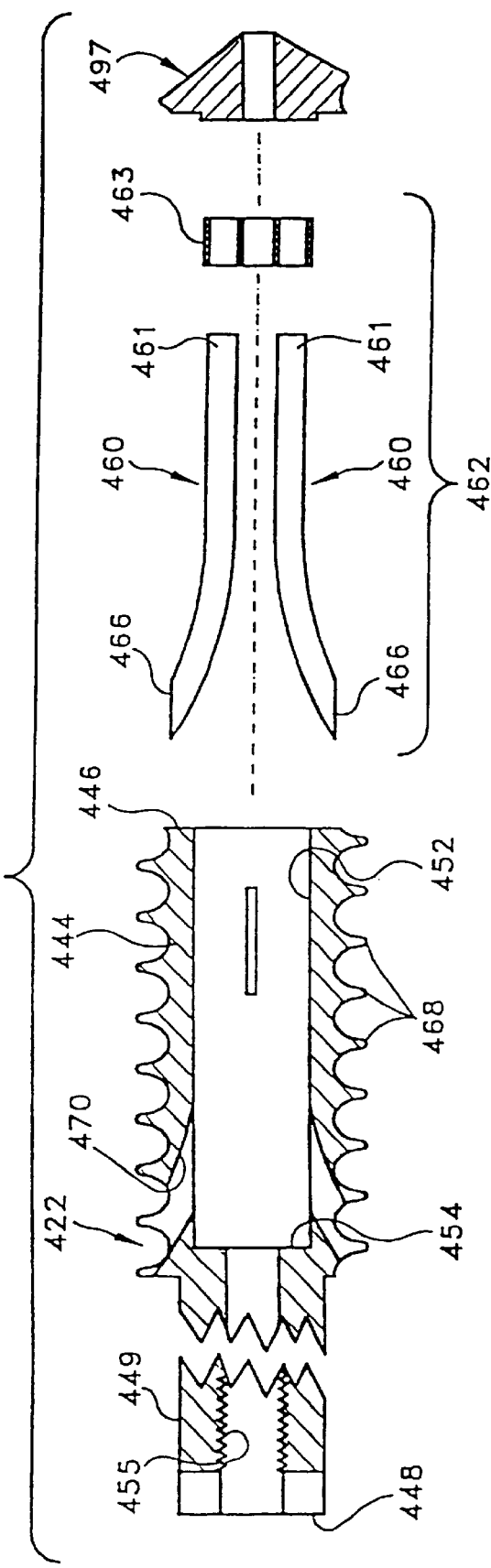
Fig. 45
Fig. 46

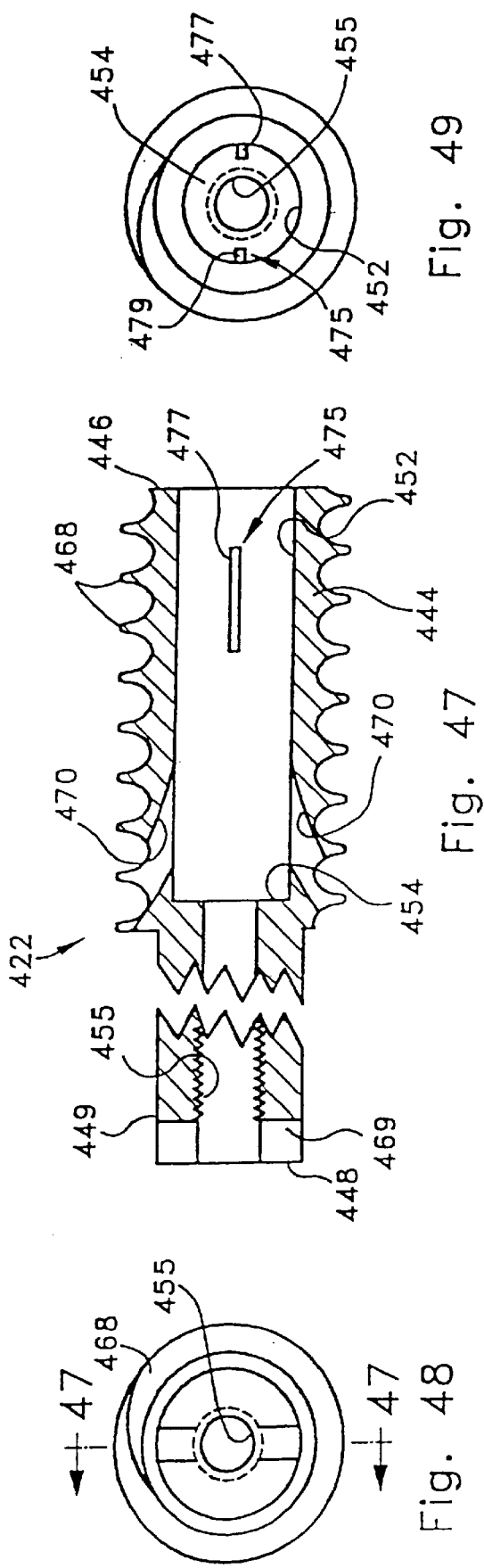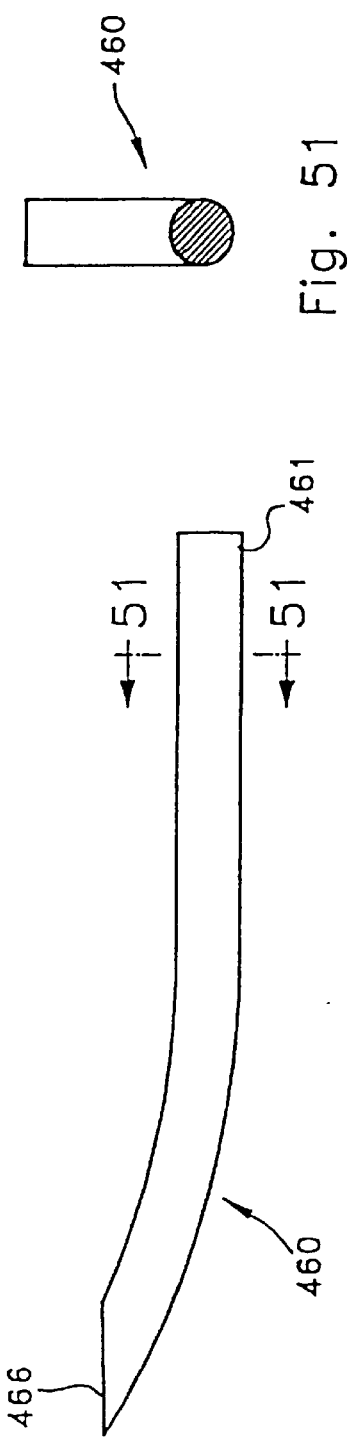
Fig. 49
Fig. 51
Fig. 47
Fig. 50
Fig. 48

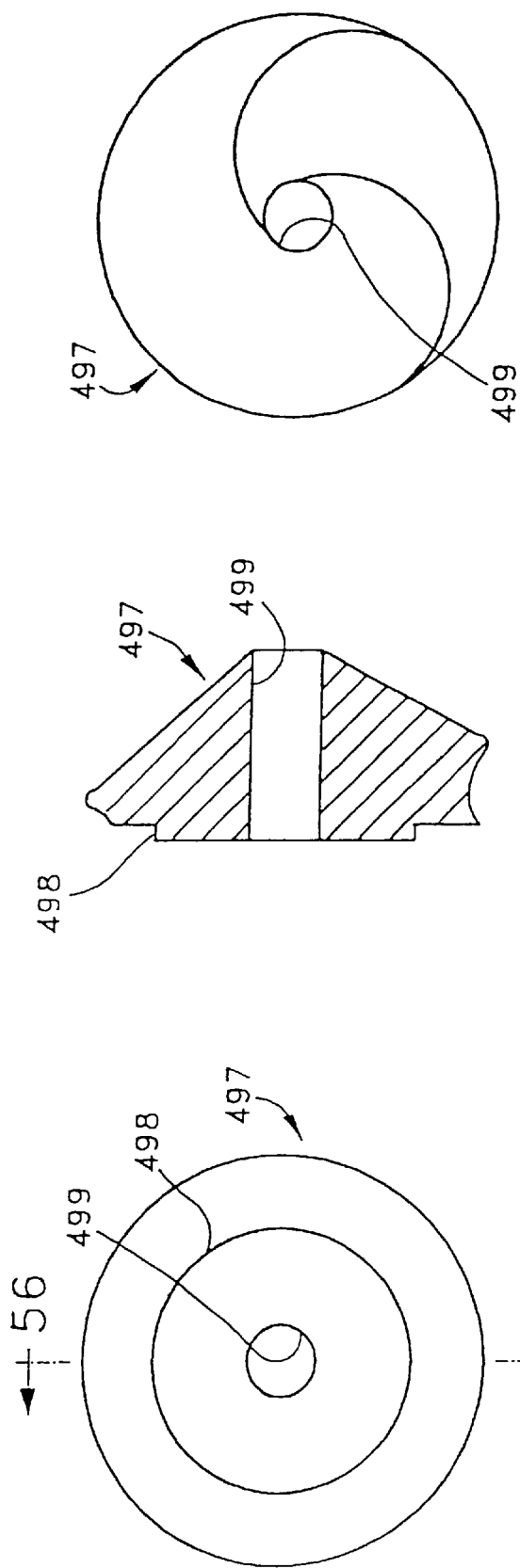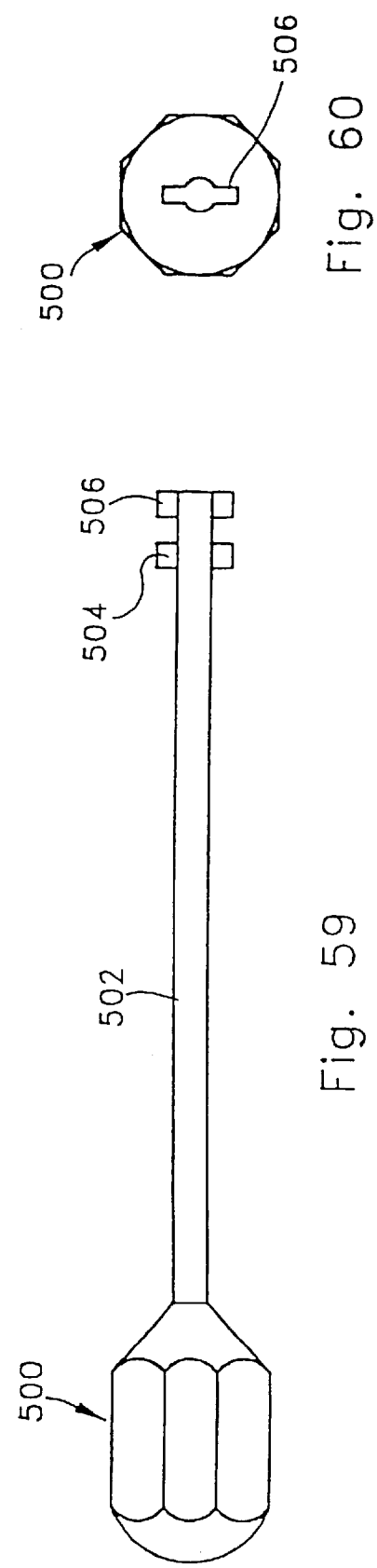

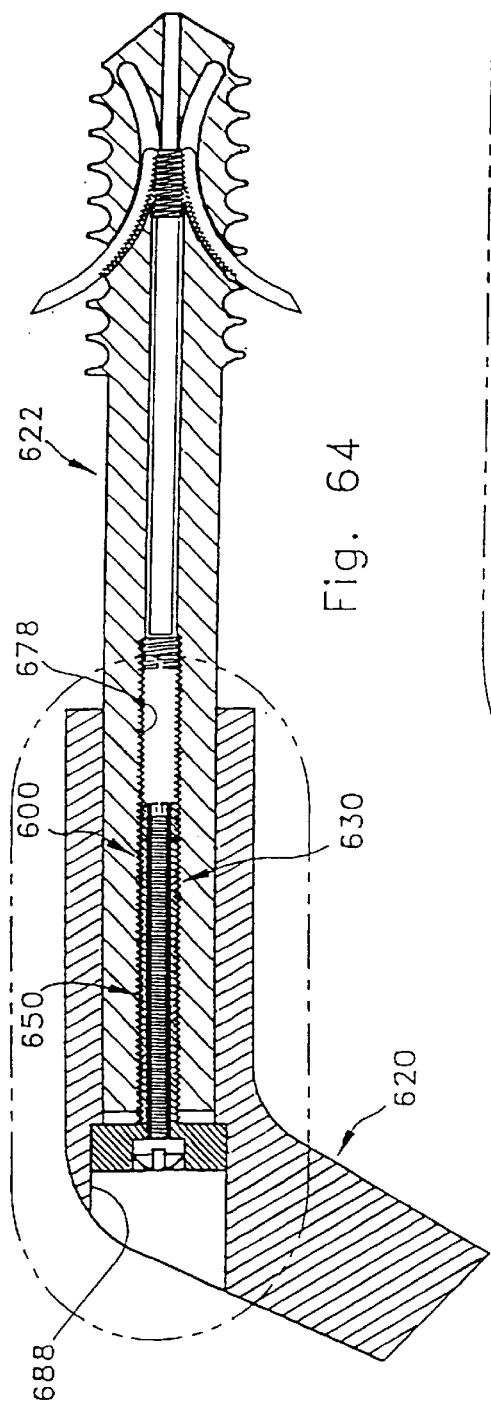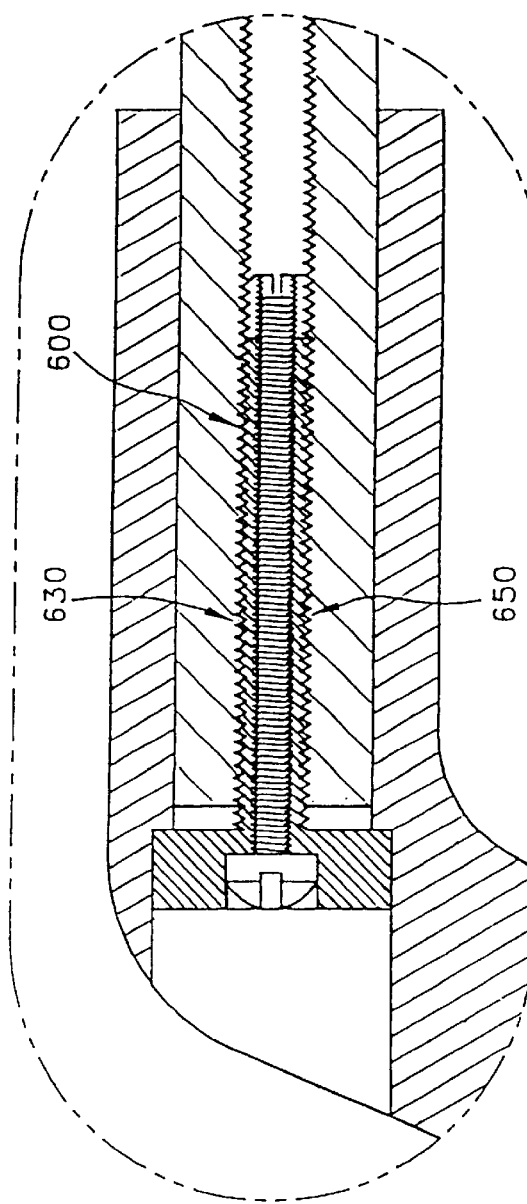

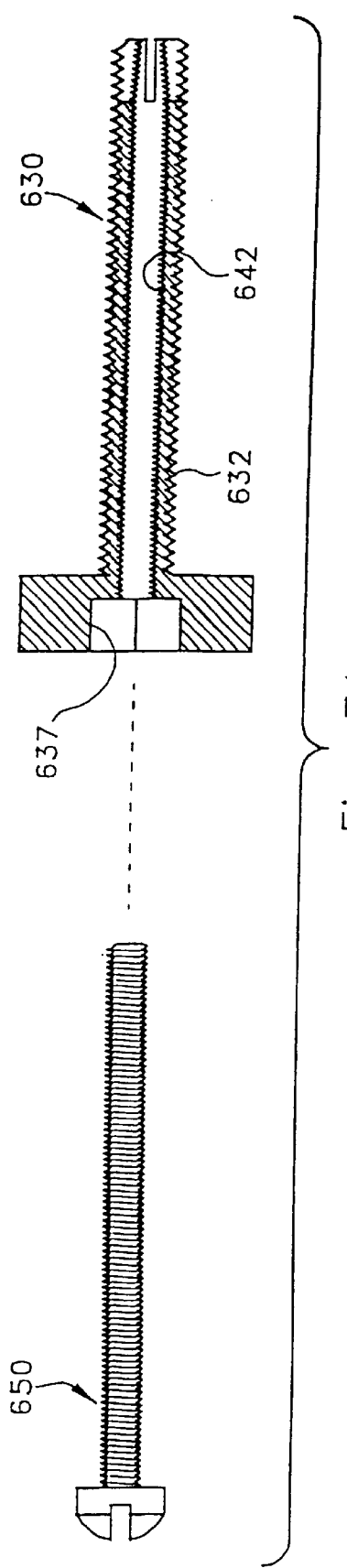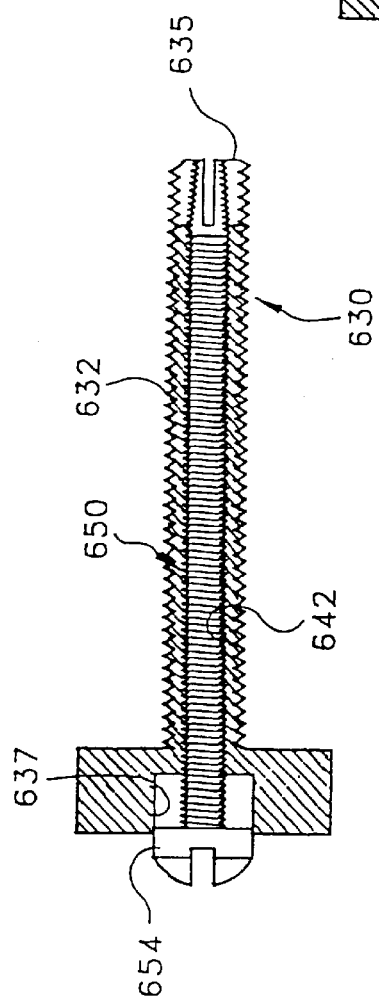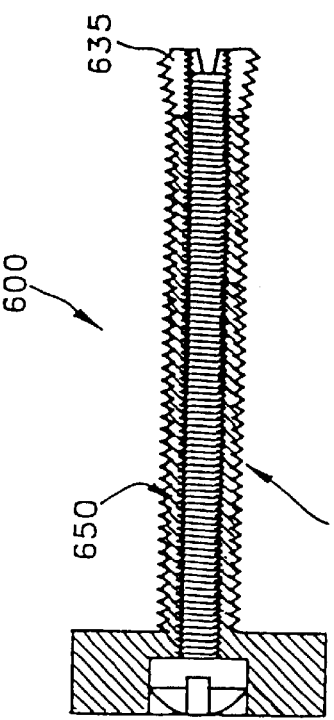
Fig. 71
Fig. 72
Fig. 73

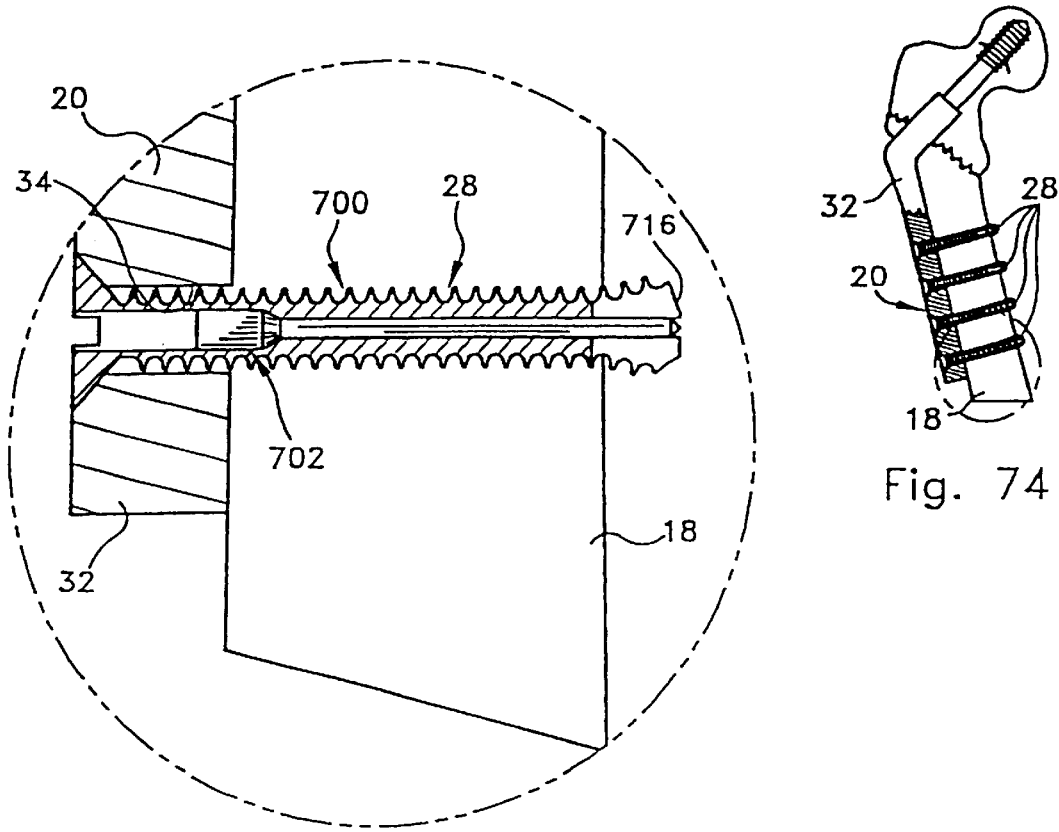
Fig. 75
Fig. 74
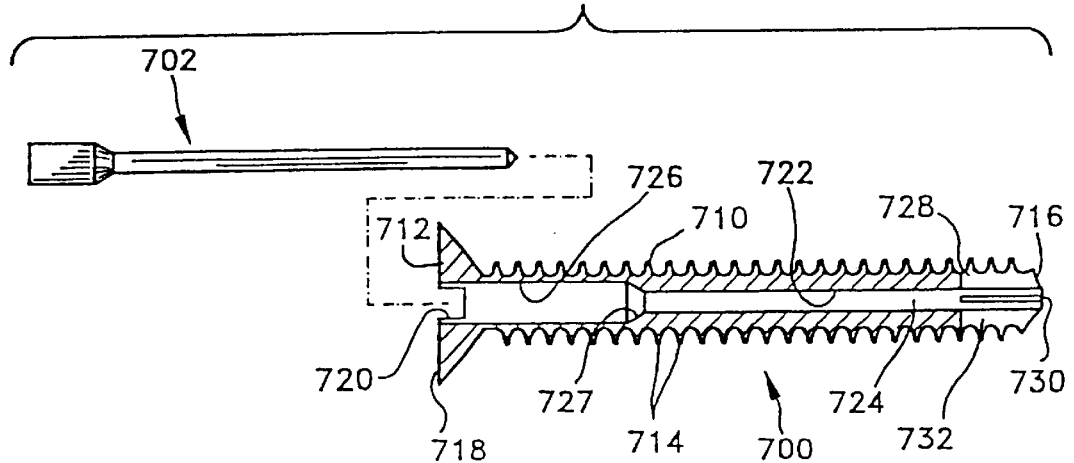
Fig. 76

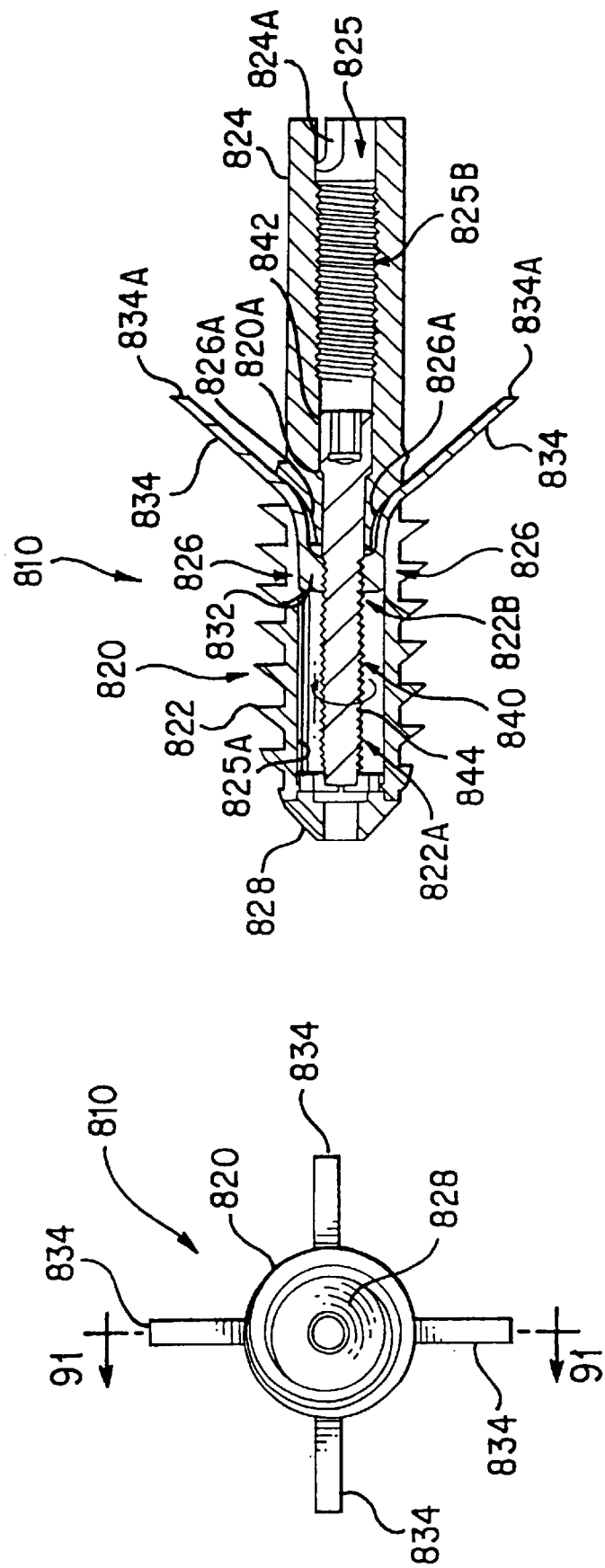

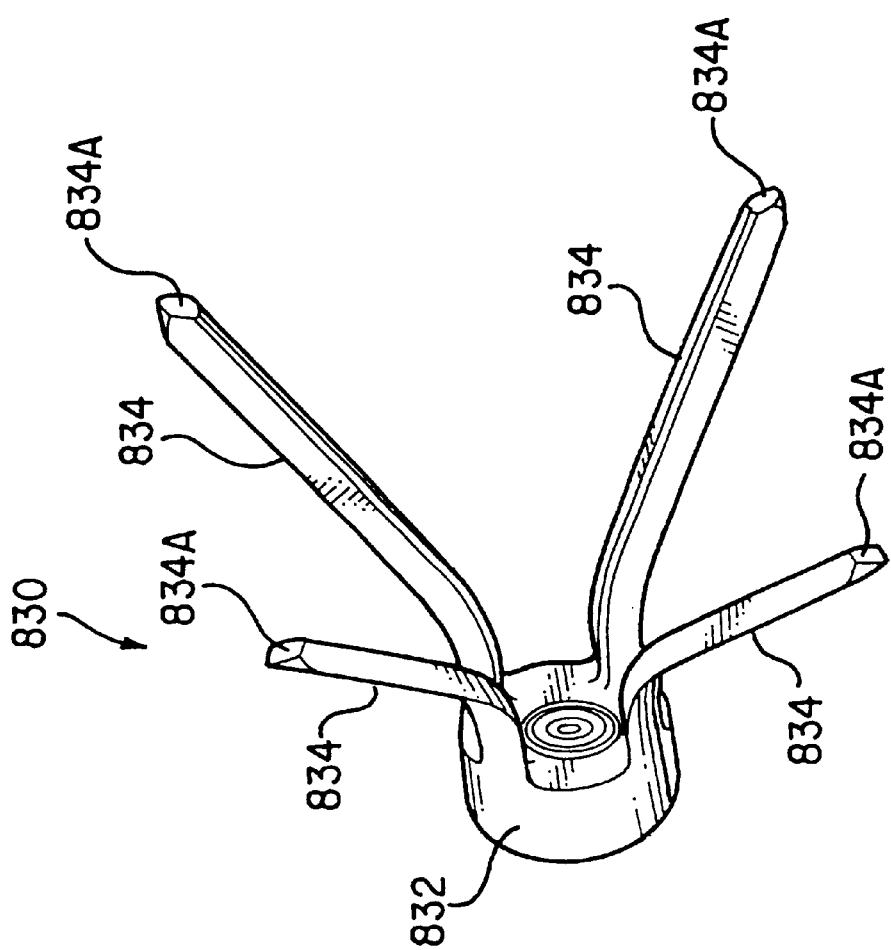

SURGICAL FASTENER ASSEMBLY

This application is a divisional of application Ser. No. 09/239,862, filed Jan. 29, 1999, now U.S. Pat. No. 6,183,474, which is a continuation-in-part of application Ser. No. 08/680,620, filed Jul. 17, 1996, now U.S. Pat. No. 5,976,139, and is also a continuation-in-part of application Ser. No. 08/615,022, filed Mar. 3, 1996, now U.S. Pat. No. 5,984,970.

FIELD OF THE INVENTION

The present invention generally relates to a surgical fastener assembly for coupling first and second bone portions across a fracture therebetween and, more specifically, to a hip-pinning system for rigidly interconnecting a femoral head to the remaining portion of the femur and across a fracture in the area of the femur neck.

BACKGROUND OF THE INVENTION

A hip joint is a heavily stressed, load-carrying bone joint in the human body. It is essentially a ball and socket joint formed by the top of the femur which pivots within a cup-shaped acetabulum at the base of the pelvis. When a break or fracture occurs adjacent to the top of the femur, the separated portions of the femur must be held together while healing occurs.

There have been a number of techniques used historically for treatment of fractures of the proximal and distal ends of the femur. In early parts of this century, patients were merely placed in bed or in traction for prolonged periods, frequently resulting in deformity or death. In the 1930s, the Smith-Peterson nail was introduced, resulting in immediate fixation of hip fractures, early mobilization of the patient, and a lowered morbidity and mortality. A number of nails have been introduced for a fracture fixation about the femur in its proximal end, including the Jewett nail and, in more recent years, dynamic compression devices that allow capture of the most proximal fragments of the femur, compression of intertrochanteric and subtrochanteric fracture fragments, rigid fixation of the most proximal and distal fragments, and a sliding lag screw or anchor which fits within a barreled side plate for allowing further compression of fragments as the patient ambulates and begins to bear weight on the fractured limb. The side plate is typically secured to the bone fragment with a series of screws or fasteners.

The use of a rigid, blade plate, has been used both at the proximal end of the femur for fixation of subtrochanteric femur fractures, and at the distal end for fixation of supracondylar and intercondylar fractures about the knee. Because these fractures can be technically challenging to fix, a dynamic compression screw, similar in many respects to a dynamic hip compression screw, but with a side plate design and angle similar to a blade plate, have been utilized for several years.

All of the known prior art, whether in the patient literature as described above, or in commercial devices, fails to take into account the shifting of the lag screw or anchor and its compression screw in the barrel as the break heals and the fragments move closer together. When this movement occurs, the compression screw can back out of the lag screw and move away from the break and into the soft tissue causing discomfort, pain and a painful bursa. With osteogenic patients, the dynamic hip compression screws can loosen or erode through the superior bone of the head of the femur, resulting in joint penetration and destruction of the joint, producing arthritis. This can necessitate additional surgery for the removal of the hip compression screw, and replacement of the hip with a prosthesis. Similarly, the use of a dynamic compression screw in osteogenic patients may result in inadequate purchase of the lag screw threads within the bone. With loss of purchase of the lag screw or anchor within the head of the femur, compression forces are dissipated, and the implant device can fail, resulting in a nonunion or malunion of the fracture fragments. Similar loss of fixation can occur about the supracondylar and intercondylar fractures of the distal femur with osteogenic patients.

To prevent loss of fixation with compression and to decrease required removal of the anchoring lag screw within the femoral head in osteogenic patients, some devices have been modified to increase purchase of the anchoring lag screw within the femoral head, by enlarging the lag screw, or by alternative means of fixation of the proximal fragment with a money bolt concept. This later device has not gained as wide an acceptance with surgeons in the United States as it differs from traditional lag screw techniques of screwing in the device, giving the surgeon a sense of "feel" of the degree of purchase of the lag screw with the bone, and thus, an idea of the degree to which the surgeon may compress the lag screw and side plate assembly without loss of fixation by "over-compression".

As the lag screw slides within the barrel of the side plate, it can become prominent on the side of patients who are cachectic. Frequently, the compression screw will back out once implanted, leading to further prominence of the device and possible erosion through the skin. This can lead to premature or unwanted additional surgery for removal of the compression screw or device increasing the morbidity, rate of infection and mortality caused by additional surgery, frequently in frail elderly patients who are least able to withstand additional surgical insult to their body. Many surgeons remove the compression screw for this very reason, to prevent it from backing out. With removal of the compression screw, however, the possibility of disassembly of the device can occur with resultant failure of fracture fixation and the necessity for further surgical operations. Some hip pinning systems have been modified to prevent the inadvertent disassembly of the lag screw and side plate by constraining the degree to which the lag screw and side plate can dissociate and by increased modularity of the side plate and lag screw component, enabling perhaps a smaller incision on the patient. This modularity, however, introduces another theoretical variable of potential loss of fixation of the side plate in the lag screw portions of the devices. Furthermore, the side plates can loosen their purchase from the distal fragments by biological resorption with resultant loss of purchase of fixation of the screws holding the side plate to the lateral side of the femur. This can happen in either the dynamic hip compression screws or the dynamic compression screws used about distal condylar fractures of the femur or for subtrochanteric fractures of the femur. Closer placement of the screw holes in the side plate, enabling more threads per unit of length of the femur, or alternating the number and location of holes in the side plate with a broader side plate have been advocated to reduce the incidence of loss of purchase of the side plate. The use of a distal compression screw allows more proximal compression in the longitudinal axis of the femur, to increase compression at the fracture site.

Furthermore, the screws or fasteners used to hold the side plate to the lateral femur often become loose as bone is resorbed about the external threading on the screws. Thus, the side plate often becomes loose from the bone, resulting in failure of the implant and loss of fixation of the fracture.

Thus, there is a need for an improved hip pinning or surgical fastener assembly that allows greater purchase of the lag screw within the femoral head of the hip bone while yielding a "feel" of fixation to the surgeon during insertion of the lag screw. Such a pinning system for fixation assembly should furthermore be designed to allow a compression screw to remain permanently in place after surgery thus maintaining the degree of compression between the lag screw and side plate. It is also desirable to prevent the screws used to maintain the side plate in fixed relation relative to the bone fragment from loosening thereby maintaining the side plate in secure relation relative to the bone to which it was initially secured.

SUMMARY OF THE INVENTION

A surgical fastener assembly for coupling first and second bone portions across a fracture therebetween is provided. In one embodiment of the present invention, the surgical fastener assembly includes an anchor that has a first externally threaded portion disposed in the first bone portion and a second portion which is at least partially disposed in the second bone portion. At least one pin is operably associated with the first portion of the anchor such that when the pin is in a retracted position the pin is disposed within the anchor and when the pin is in an extended position at least a portion of the pin extends outward from the anchor. An actuator is disposed within the anchor and is operably coupled with the at least one pin. A guide is adapted to be fixedly secured to the second bone portion and includes a sleeve. The second portion of the anchor is received within the sleeve. A fastener is provided that has a head portion and an externally threaded shank portion. The shank portion threadedly engages with the anchor and the head portion operably engages with the guide.

DESCRIPTION OF THE DRAWINGS

FIG. 3 is an assembled perspective view of the present invention;

FIG. 4 is a disassembled side elevational view illustrating component parts of one form of the present invention;

FIG. 5 is a longitudinal sectional view through a fastener forming part of the present invention;

FIG. 6 is a sectional view similar to FIG. 5 but showing pins or barbs of the fastener in an extended position;

FIG. 11 is an enlarged perspective view of a pin or barb forming part of the first embodiment of the surgical fastener assembly according to the present invention;

FIG. 12 is a side elevational view of the pin illustrated in FIG. 11;

FIG. 13 is another side elevational view of the pin or barb illustrated in FIG. 11;

FIG. 14 is an end view of the pin or barb illustrated in FIG. 12;

FIG. 15 is a sectional view taken along line 15—15 of FIG. 12;

FIG. 25A illustrates assembly of the surgical anchor assembly according to one form of the invention with the pins or barbs extended and a tool positioned to engage the retainer illustrated in FIGS. 21 through 25;

FIG. 25B is similar to FIG. 25A but illustrates further assembly of the surgical anchor assembly according to one form of the invention with the pins or barbs extended and a tool for moving the retainer illustrated in FIGS. 21 through 25 into operable engagement with the compressive cannulated fastener illustrated in FIGS. 16 through 20;

FIG. 43 is a view similar to FIG. 42 but showing an alternative form of compression screw assembly arranged in operable combination with the anchor and a conventional side plate;

FIG. 44 is a view similar to FIG. 43 but showing a driver of the compression screw assembly arranged in a locking relationship relative to a compression screw;

FIG. 45 is a longitudinal sectional view of a third embodiment of a surgical anchor assembly according to the present invention with an alternative form of pins operably associated therewith and in a retracted relationship therewith;

FIG. 46 is a fragmentary longitudinal sectional view showing component parts of the third embodiment of the present invention in exploded or disassembled relation relative to each other;

FIG. 47 is a fragmentary longitudinal sectional view of an anchor or insert forming part of the third embodiment of the present invention;

FIG. 48 is a left end view of the anchor illustrated in FIG. 47;

FIG. 49 is a right end view of the anchor illustrated in FIG. 47;

FIG. 50 is a side elevational view of a pin forming part of the third embodiment of the present invention;

FIG. 51 is a sectional view taken along line 51—51 of FIG. 50;

FIG. 56 is a sectional view of an end cap forming part of the third embodiment of the present invention;

FIG. 57 is a left end view of the end cap shown in FIG. 56;

FIG. 58 is a right end view of the end cap shown in FIG. 56;

FIG. 59 is a side elevational view of a tool used to extend and retract the pins in the third embodiment of the anchor assembly shown in FIG. 45;

FIG. 60 is a right end view of the tool shown in FIG. 59;

FIG. 64 is another form of surgical anchor assembly having an alternative form of a compression screw assembly for holding the anchor and guide in compressive relationship relative to each other;

FIG. 64A is an enlarged sectional view of the compression screw assembly encircled in FIG. 64;

FIG. 71 is a schematic partially sectional elevational view of the compression screw (FIG. 65) and driver (FIG. 68) shown in exploded or disassembled relation relative to each other;

FIG. 72 is a schematic representation of the driver being illustrated in partial relation with the compression screw;

FIG. 73 is a schematic representation of the driver being illustrated in complete relation with the compression screw;

FIG. 74 is a reduced view similar to FIG. 2;

FIG. 75 is an enlarged view of that area encircled in FIG. 74;

FIG. 76 illustrates component parts of an alternative form of a screw assembly used to secure the guide to the bone, with the component parts thereof shown in disassembled relationship relative to each other;

FIG. 90 is a front view of the anchor assembly with the tangs in a deployed position;

FIG. 91 is a cross-sectional view of the anchor assembly as taken along line 91—91 of FIG. 90;

FIG. 92 is a perspective view of the tang assembly with the tangs in a deployed position.

DETAILED DESCRIPTION

Figure 1:
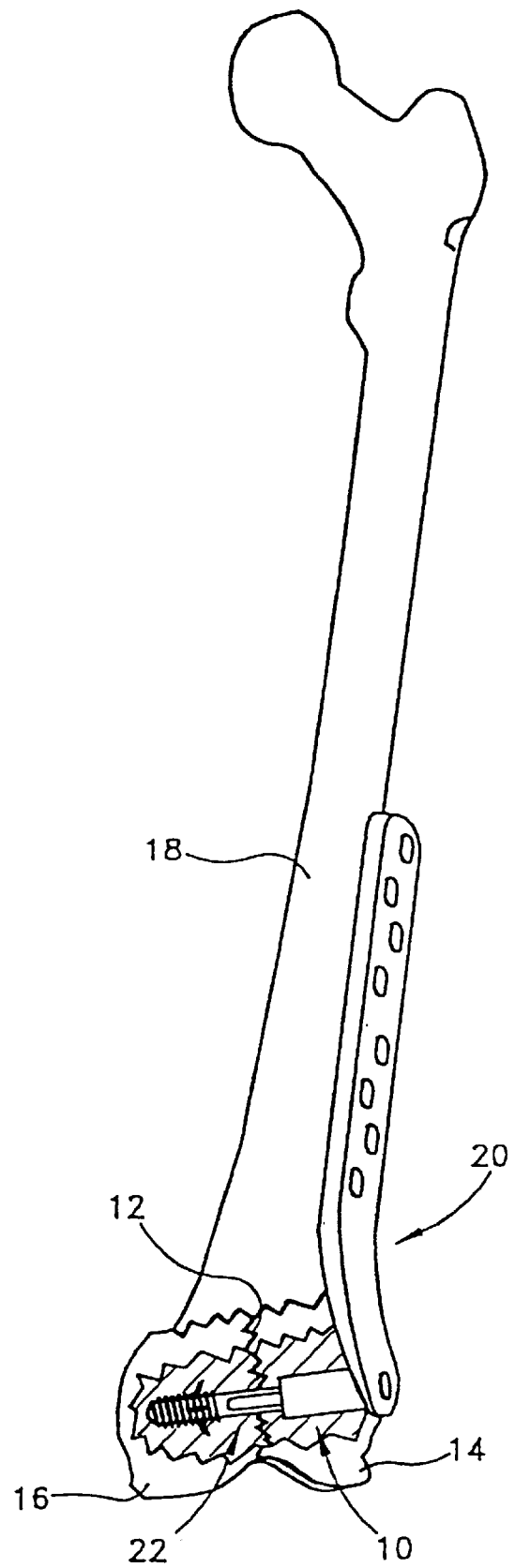
FIG. 1 is a view showing a surgical fastener assembly according to the present invention in operable association with and extending across a condylar fracture.

While the present invention is susceptible of embodiment in various forms, there is shown in the drawings and will hereinafter be described preferred embodiments of the invention with the understanding that the present disclosure is to be considered as setting forth exemplifications of the invention which are not intended to limit the invention to the specific embodiments illustrated.

Referring now to the drawings, wherein like reference numerals refer to like parts throughout the several views, there is schematically represented in FIG. 1 one form of a fastener assembly 10 used to compressively secure fractured first and second bone fragments across the fracture therebetween. In the illustrated embodiment, the surgical fastener assembly 10 is used to set a condylar fracture accurately along a fracture line 12 disposed between proximal and distal portions 14 and 16, respectively, of a bone 18.

Figure 2:
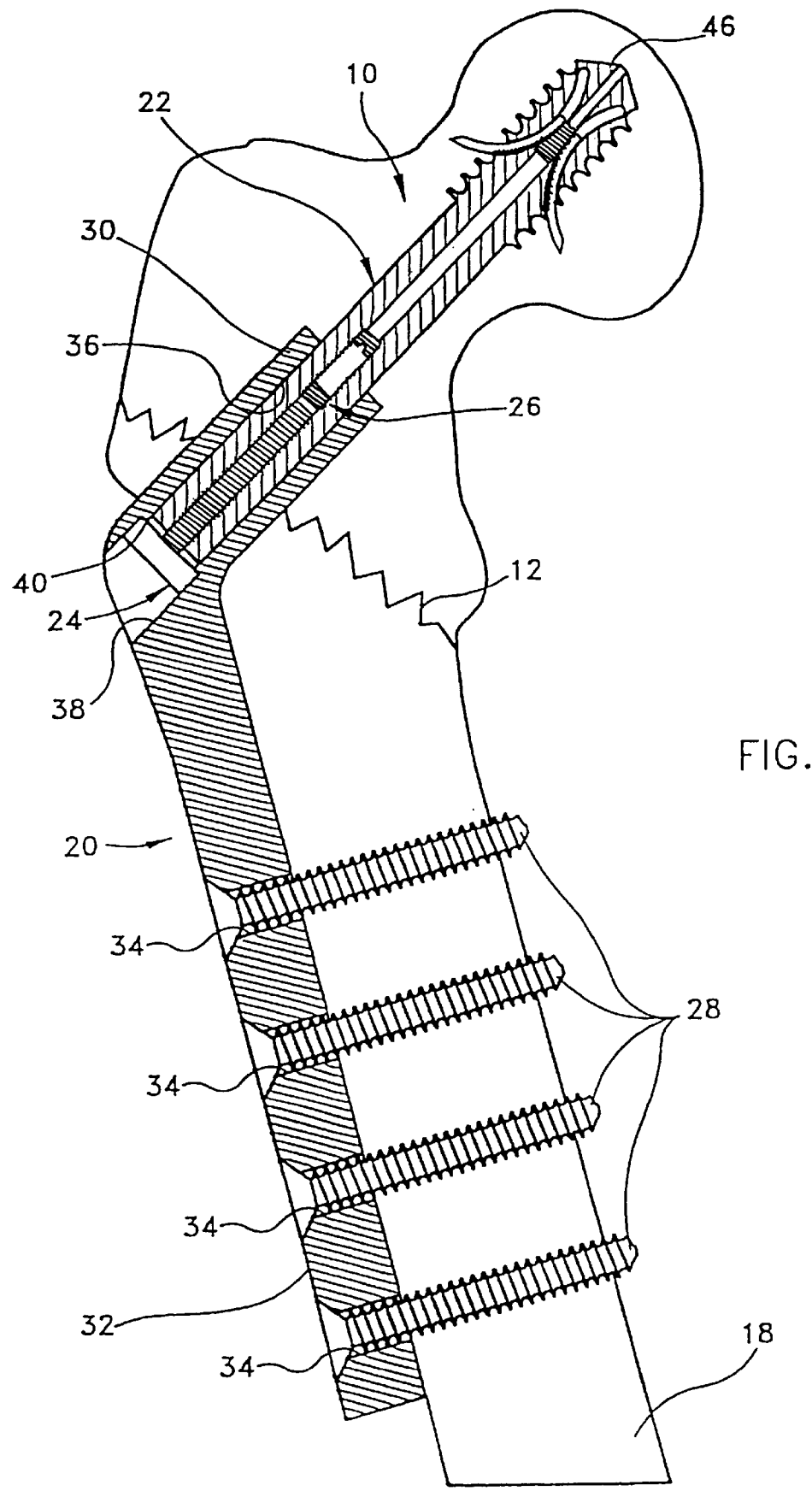
FIG. 2 is an enlarged view, partly in section, of the apparatus of the present invention shown in FIG. 1.
Figure 10:
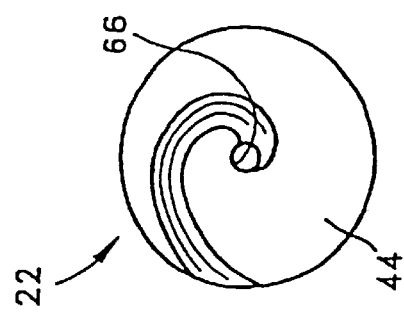
FIG. 10 is another end view of the present invention.
Figure 7:
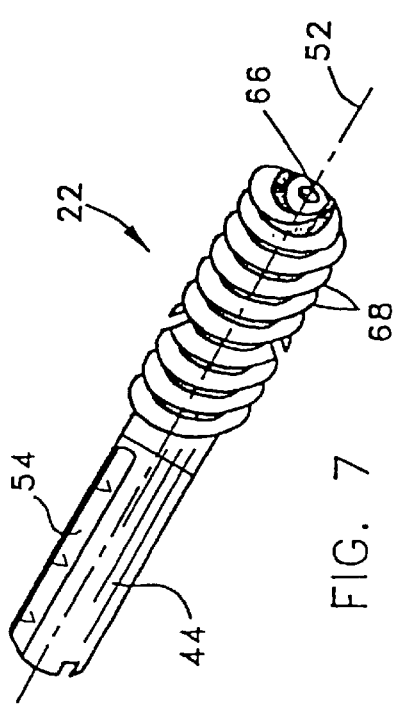
FIG. 7 is a perspective view of the fastener illustrated in FIGS. 5 and 6.

As shown, the surgical fastener assembly 10 includes a guide, generally represented by reference numeral 20 and an elongated anchor, generally represented by reference numeral 22. As shown in FIG. 2, the surgical anchor assembly 10 further includes a compression screw or fastener 24 and a retainer 26 for releasably locking the fastener 24 against rotation. As shown in FIG. 2, a series of screws 28 operate in combination with and serve to secure the guide 20 to the bone section 18.

As shown in FIGS. 2 through 4, guide 20 includes a hollow sleeve 30 that is rigidly attached to a trochanteric plate 32 at the proper angle. The proximal portion 14 of the bone 18 is bored so as to receive the sleeve 30. The distal portion 16 of the bone 18 is configuratively manipulated to accommodate an end portion of the sleeve 30 therewith. As shown, the plate 32 is provided with a plurality of throughholes 34 that allow the screws 28 to pass endwise therethrough, thereby securing the guide 20 to the bone section 18. The sleeve 30 defines a throughbore 36 that is open at opposite ends thereof. In a preferred form of the invention, the guide 20 is formed from a material chosen from the class comprised of: titanium, a titanium alloy, stainless steel, or cobalt chromium alloy.

Notably, the throughbore 36 is provided with a counterbore 38 at one end thereof. In the illustrated embodiment, the counterbore 38 has a larger diameter than does the throughbore 36. Accordingly, an annular or radial step 40 is defined toward one end of the throughbore 36.

As shown in FIG. 4, the anchor 22 includes an elongated insert 44 preferably formed from a material chosen from the class comprised of: titanium, a titanium alloy, stainless steel or cobalt chromium alloy. The insert 44 has opposed first and second axially aligned ends 46 and 48, respectively. The insert 44 is sized such that when inserted within the bone, the first end 46 is disposed on one side of the fracture line 12 while the second end 48 of insert 44 is disposed on an opposite side of the fracture line 12. Notably, cooperative instrumentalities 50 are defined on the sleeve 30 of guide 20 and on insert 44. The purpose of the cooperative instrumentalities 50 is to allow for axial movement of the sleeve 30 along an axis 52 defined by the insert 44 while preventing rotational movement of the sleeve 30 relative to the anchor 22.

In the illustrated embodiment, and as well known, the cooperative instrumentalities 50 preferably comprises a pair of flats 54 extending axially along and inwardly from the second end 48 of insert 44. The flats 54 are diametrically opposed and generally parallel to each other. As shown in FIG. 3, the throughbore 36 of sleeve 30 includes generally flat sides 56 that are arranged in opposed and generally parallel relationship relative to each other. The flat sides 56 of bore 36 to allow the second end 48 of the insert to slidably move therewithin while the flats 54 cooperate with the flat sides 56 in preventing rotation of the sleeve 30 and, thereby, the guide 20 relative to the anchor 22. It will be appreciated, and it is within the spirit and scope of the present invention that other forms of cooperative instrumentalities for allowing endwise axial movement of the anchor 22 relative to the guide 20 while preventing rotational movement therebetween would equally suffice.

As shown in FIGS. 5 and 6, the anchor 22 of the surgical fastener assembly 10 further includes a series of elongated pins 60 operably associated toward the first end 46 of the insert 44 for movement between a retracted position (FIG. 5) and a radially extended position (FIG. 6). As shown, the pins 60 are carried by the insert 44 for endwise and radial displacement relative thereto. In the illustrated embodiment of the invention, four pins 60 are equidistantly spaced relative to each other for positive endwise movement in opposite directions between the retraced and extended positions shown in FIGS. 5 and 6., respectively.

A salient feature of the present invention relates to the provision of a mechanism 64 for positively positioning the pins 60 relative to the surgical anchor 22. That is, and as will be described in detail below, the purpose of mechanism 64 is to positively extend the pins 60 radially outwardly from the insert 44, thereby enhancing securement of the anchor 22 within the bone (FIG. 1). Additionally, and in response to mechanical manipulation, the mechanism 64 furthermore operates to positively retract the pins 60 into the surgical anchor 22, thereby facilitating surgical removal of the anchor 22 when desired or when found to be surgically necessary.

Turning to FIGS. 7 through 10, insert 44 of anchor 22 defines an elongated bore 66 preferably arranged coaxially about the longitudinal axis 52 and opening to the first and second ends 46 and 48, respectively, of the insert 44. As shown, the first end 46 of the fastener 24 is preferably pointed to facilitate insertion of the fastener 24 into the bone.

As will be appreciated by those skilled in the art, the exterior configuration of the insert 44 can take a myriad of shapes and forms. According to the present invention, and as illustrated in FIGS. 7 through 10, the elongated insert 44 preferably has external threading 68 axially extending therealong and leading rearwardly from the pointed first end 46. As mentioned, the pointed configuration of the insert 44 promotes insertion and, in the illustrated embodiment, self tapping of the anchor 22 within the substance of the bone. The external threading 68 along the exterior of insert 44 has a relatively coarse pitch to enhance the purchasing ability and the anchorage of the anchor 22 within the substance of the bone in response to turning movements being imparted to the anchor 22.

Figure 9:
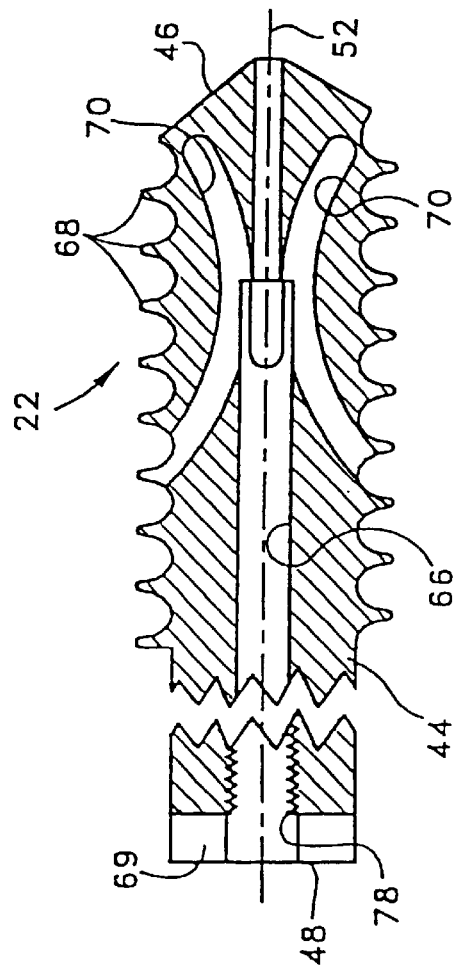
FIG. 9 is a sectional view taken along line 9—9 of FIG. 8.
Figure 8:
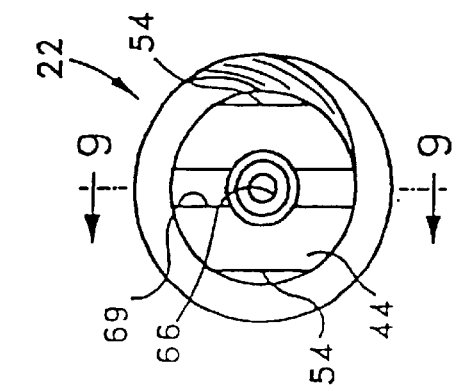
FIG. 8 is an end view of the fastener as shown in FIG. 7.
Figure 16:
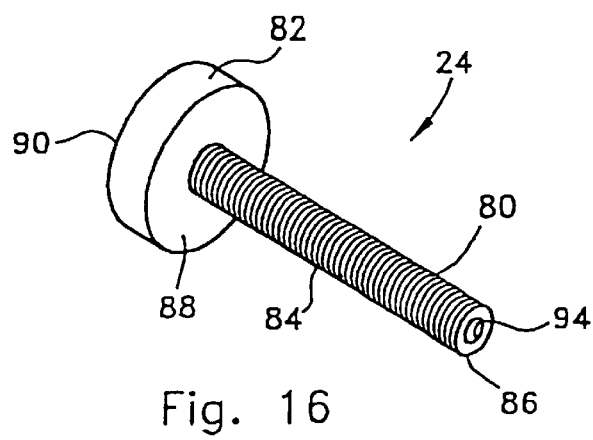
FIG. 16 is a perspective view of one form of a compression screw forming part of the present invention.

As shown in FIG. 9, the second or trailing end 48 of the insert 44 is preferably configured to releasably accommodate a driving tool (not shown) capable of imparting turning movements to the anchor 22. In a preferred form, and as shown in FIGS. 8 and 9, the trailing or second end of the insert 44 is suitably configured with a slot-like opening 69 for releasably accommodating a distal end of a driving tool. It will be appreciated, however, that any suitable configuration including a socket-like configuration would equally suffice without detracting or departing from the spirit and scope of the present invention.

As shown in FIG. 9, the insert 44 further defines a series of axially elongated openings arranged in spaced circumferential relation relative to each other. In the illustrated form of the invention, insert 44 is provided with four openings 70. Since the openings 70 are all substantially similar, only one opening 70 will be described in detail with the understanding that the other openings in the insert are similar thereto. Each opening 70, intermediate positive ends thereof, intersects with and opens to the elongated bore 66 defined by insert 44. Preferably, each elongated opening 70 has a blind configuration but opens at one end to the exterior of the insert 44. As will be appreciated, the openings 70 are generally equally disposed about the axis 52 of insert 44. In the form of the invention illustrated in FIG. 9, each elongated opening 70 has a curvilinear or arcuate configuration between opposite ends thereof. That is, in the illustrated form of the invention, each opening 70 has an arcuate configuration having a predetermined and substantially constant radius.

An exemplary form of pin 60 is illustrated in FIGS. 11 through 15. Each pin 60 is shaped to slidably fit endwise within a respective one of the openings 70 formed in the insert 44. The shape and size of each pin 60 generally corresponds to the shape and size of an opening 70 defined by the insert 44. Preferably, each pin 60 is formed from a substantially rigid material that is biocompatible with the bone tissue of human beings. That is, the pins 60 should be configured with sufficient strength so as to allow for insertion in and through the bone tissue without substantially bending intermediate opposite ends thereof. In a most preferred form of the invention, each pin 60 is formed from a material selected from the class comprised of: titanium, a titanium alloy, stainless steel, or a cobalt chromium alloy.

In the embodiment illustrated in FIGS. 11 through 15, each pin 60 has a leading end 74 and an opposite generally pointed end 76. Intermediate its ends, each pin 60 preferably has a curvilinear or arcuate configuration. In the illustrated form of the invention, each pin 60 has a curved arc with a predetermined radius that is substantially equal to the predetermined radius of each opening 70 formed in insert 44 (FIG. 9) and which extends proximate to and outwardly away from the axis 52 of insert 44.

In a most preferred form of the invention, each pin 60 preferably forms an arc of about 80 degrees between opposite ends thereof, and with the length of each pin 60 being selected such that when the leading end 74 of the pin 60 is fully retracted within the fastener (FIG. 5), the opposite pointed end 76 of the pin or barb 60 will be positioned within the outside diameter of the insert 44 (FIG. 5) to facilitate insertion of the surgical anchor 20 within the bone of the patient. Moreover, it is to be appreciated that the length of each barb or pin 60 is sized such that when the pins 60 are displaced to their extended position (FIG. 6) the leading end 74 of each pin 60 remains operably associated with the mechanism 64 to allow for positive retraction of the pins 60 from their extended positions when desired or found necessary by the surgeon.

The compressive and cannulated fastener 24 as schematically illustrated in FIGS. 16 through 20. The purpose of the cannulated fastener 24 is to maintain the bone fragments (FIG. 1) in adjustable compressive relationship relative to each other as by axially fixing the guide 20 to the anchor 22 (FIG. 2).

Returning to FIGS. 5, 6, and 9, the elongated bore 66 of the insert 44 opens to the second or trailing end 48 thereof. The bore 66 defines an internally threaded portion 78 extending inwardly from the second or trailing end 48 of the insert 44. Preferably, the internally threaded portion 78 of bore 66 has a relatively fine pitched threading extending therealong.

The compressive and cannulated fastener 24 is schematically illustrated in FIGS. 16 through 20. The purpose of the cannulated fastener 24 is to maintain the bone fragments (FIG. 1) in adjustable compressive relationship relative to each other as by axially fixing the guide 20 to the anchor 22 (FIG. 2) such that the guide 20 is prevented from axially moving away from the anchor 22, but allows movement of guide 20 toward the pointed or first end 46 of the anchor 22 (FIG. 2).

Fastener 24 is preferably formed from a material that is biocompatible with bone tissue or a substance and is preferably selected from the class comprised of: titanium, a titanium alloy, stainless steel, or a cobalt chromium alloy. As will be appreciated, and although not specifically mentioned herein, other unnamed materials may well equally suffice without detracting or departing from the spirit and scope of the present invention.

As shown, the fastener 24 is provided with an elongated shank position 80 and an enlarged head portion 82. The shank portion 80 of fastener 24 is provided with external threading 84 extending axially from a leading end 86 of the fastener 24. The external threading 84 has a relatively fine pitch that corresponds to the threading extending internally along the threaded portion 78 of anchor 22. The enlarged head portion 82 of fastener 24 has a diameter slightly smaller than the diameter of the counterbore 38 defined by the insert 44 (FIG. 2). As will be appreciated from an understanding of the present invention, the axial length of the head portion 82 can be altered from that illustrated without detracting or departing from the spirit and scope of the present invention. That is, during a surgery, surgeon may have a collection of different fasteners 24 to select from; with each anchor having a different length such that a proper relationship is maintained between the guide 20 and anchor 22. Notably, the enlarged head portion 82 defines a radial shoulder 88 relative to the shank portion 80.

Figure 18:
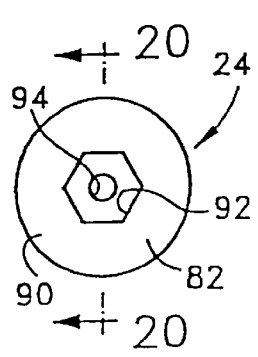
FIG. 18 is a left end view of the compression screw illustrated in FIG. 17.
Figure 17:
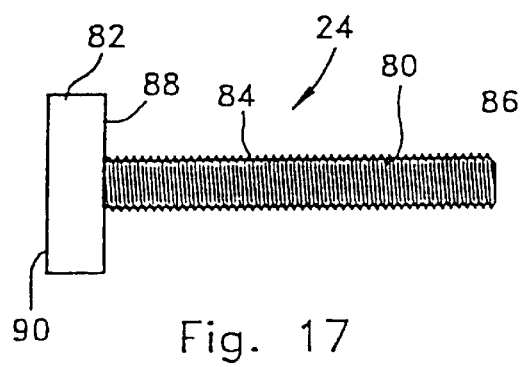
FIG. 17 is a side elevational view of the compression screw illustrated in FIG. 16.
Figure 19:
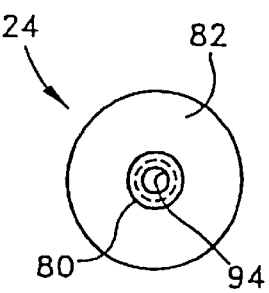
FIG. 19 is a night end view of the compression screw illustrated in FIG. 17.
Figure 20:
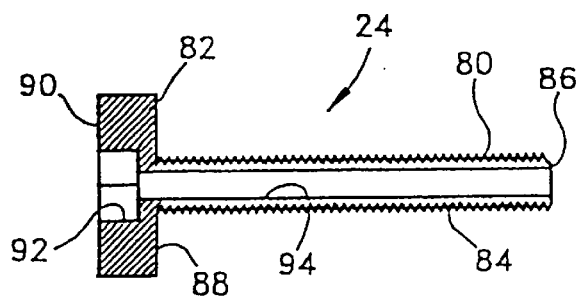
FIG. 20 is a sectional view taken along line 20—20 of FIG. 18.
Figure 21:
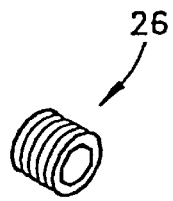
FIG. 21 is a perspective view of a retainer forming part of the anchor assembly illustrated in FIG. 2.

As shown in FIGS. 18 and 20, a trailing end 90 of the fastener 24 is preferably configured to releasably accommodate a driving tool (not shown) capable of imparting turning movements to the fastener 24. In a preferred form, and as shown in FIGS. 18 and 20, the trailing end 90 of fastener 24 is configured with a socket-like opening 92 for releasably accommodating a distal end of a driving tool. In a most preferred form of the invention, and as shown, the socket or opening 92 has a hexagonal-like cross sectional configuration. It will be appreciated, however, that any suitable configuration including an elongated slot would equally suffice without detracting or departing from the spirit and scope of the present invention. The cannulated fastener 24 furthermore defines an elongated bore 94 that opens to the leading and trailing ends 86 and 90, respectively, of the fastener.

In the illustrated embodiment shown in FIG. 2, the anchor 22 is fastened within the bone fragment to one side of the fracture line 12. As mentioned, anchor 22 is configured such that the opposite or second end 48 of the anchor 22 extends to an opposite side of the fracture line 12. Thereafter, the guide 20 is arranged in cooperative relationship relative to the anchor 22. As shown, the sleeve 30 of guide 20 slidably fits endwise over and telescopically along the free end of the anchor 22. The screws 28 are used to fasten the plate 32 of guide 20 to the bone 18. It will be observed that the cannulated compressive fastener 24 is thereafter arranged in operable combination with the anchor 22 and guide 20. That is, the leading end 86 of the compressive screw 24 is inserted through the bore 36 of the sleeve 30 in turn such that the external threading 84 extending there along operably engages with the internal threading 78 at the proximal end of the anchor 22. Continued rotation of the fastener 24, ultimately, will cause the radial shoulder 88 on the enlarged head portion 82 to engage the radial stop 40 defined by the counterbore 38 and the guide 20. As will be appreciated, continued rotation of the screw 24 will cause the bone fragments to be brought into compressive relationship relative to each other. The compressive screw 24 furthermore allows the surgeon the appropriate "feel" as the screw is tightened, thus bringing the bone fragments into compressive relationship relative to each other.

One form of a retainer 26 is schematically illustrated in FIGS. 21 through 25. As shown, retainer 26 has external threading 100 extending axially there along between leading and trailing ends 102 and 104, respectively thereof. The retainer 26 is preferably formed from a material that is biocompatible with bone tissue or substance and is preferably ultra-high molecular weight polyethylene. It should be appreciated, however, that other unnamed materials would equally suffice without detracting or departing from the spirit and scope of the present invention. Notably, the external threading 100 extending along the outside of retainer 26 has a fine pitch thereto which corresponds to the threading extending along the internally threaded portion 78 of the insert 44.

Figure 25:
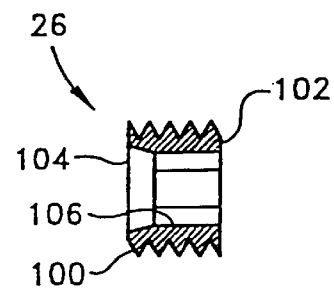
FIG. 25 is a sectional view taken along line 25—25 of FIG. 23.
Figure 23:
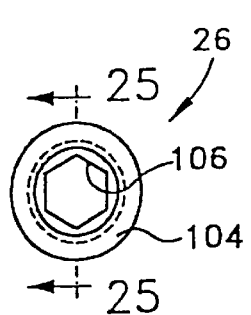
FIG. 23 is a left end view of the retainer illustrated in FIG. 22.
Figure 22:
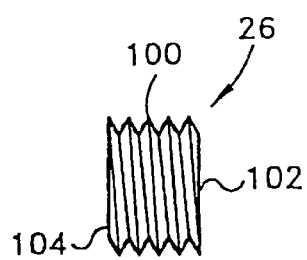
FIG. 22 is a side elevational view of the retainer illustrated in FIG. 21.
Figure 24:
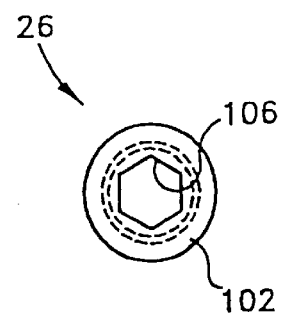
FIG. 24 is a right end view of the retainer shown in FIG. 22.
Figure 26:
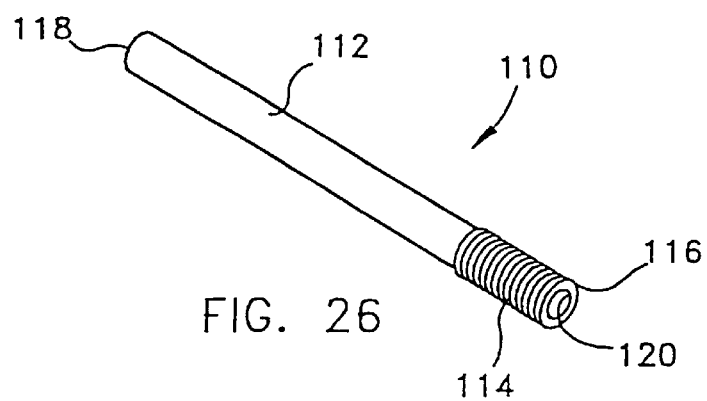
FIG. 26 is a perspective view of a driver forming part of the first embodiment of this surgical fastener assembly according to the present invention.

As shown in FIGS. 23, 24 and 25, the retainer 26 is provided with a throughbore 106 that opens to opposite ends 102 and 104 of the retainer. In a preferred form, and as shown in FIGS. 23, 24 and 25, a lengthwise portion of the throughbore 106 has a hexagonal-like cross sectional configuration for releasably accommodating a distal end of the driving tool. It will be appreciated, however, that any suitable socket-like configuration other than hexagonal would equally suffice without detracting or departing from the spirit and scope of the present invention.

During assembly of the surgical fastener assembly 10, and as shown in FIG. 25A, the retainer 26 is initially threaded into the internally threaded portion 78 of the anchor 22. Thereafter, and in the manner described above, the compressive fastener 24 is operably associated with the anchor 22. After the compressive relationship between the guide 20 and anchor 22 has been established, as a result of turning the compressive screw 24, a suitably elongated tool 95 is passed through the bore 94 (FIG. 20) of the cannulated fastener 24 and into releasable engagement with the socket-like configuration defined in the throughbore 106 of retainer 26.

As shown in FIG. 25B, appropriate rotation of the retainer 26 under the influence of tool 95 will thereafter cause the trailing end 104 to be moved into abutting relationship to the leading end 86 of the compressive screw 24, thereby locking the compressive screw 24 and, thus, maintaining the compressive relationship between the bone fragments. As will be appreciated, however, the bone fragments are allowed to shift through the axial movement of the head portion 82 along the length of the counterbore 38. The head portion 82 of the compressive screw 24 limits, however, movement of the anchor 22 and the bone fragments secured thereby away from the bone 18, thereby maintaining the compressive relationship therebetween.

The mechanism 64 for positively displacing the pins 60 in opposite directions between retracted and extended positions (FIGS. 5 and 6, respectively) will now be described. As will be appreciated, the mechanism for positively displacing the pins 60 in opposite directions can take a myriad of different forms without detracting or departing from the spirit and scope of the present invention. One mechanism which has proven advantageous and quite effective involves equipping the anchor 20 with a manually operated driver 110 (FIGS. 5 and 6) which is operably associated with the pins 60 such that upon manipulation of the driver 110 the pins 60 will endwise be displaced relative to the anchor 22, thereby effecting the anchorage of the surgical anchor 22 within the bone.

Figure 28:
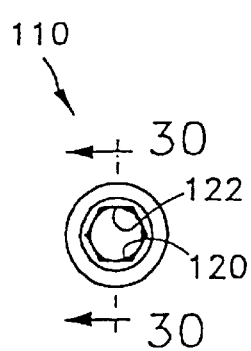
FIG. 28 is a left end view of the driver illustrated in FIG. 27.
Figures 27, 29:
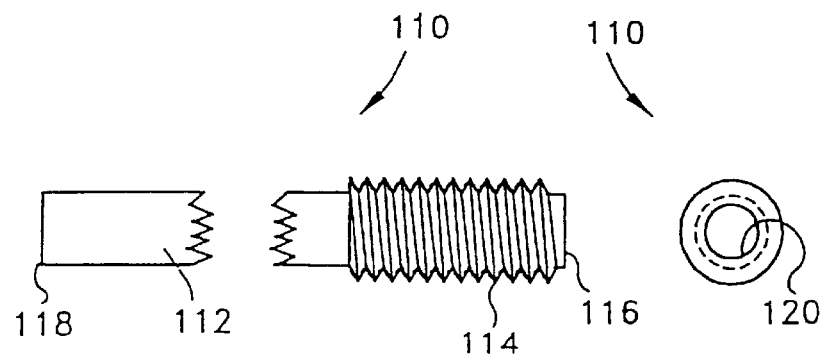
FIG. 27 is a fragmentary side elevational view of the driver illustrated in FIG. 26.
FIG. 29 is a right end view of the driver illustrated in FIG. 27.
Figure 30:
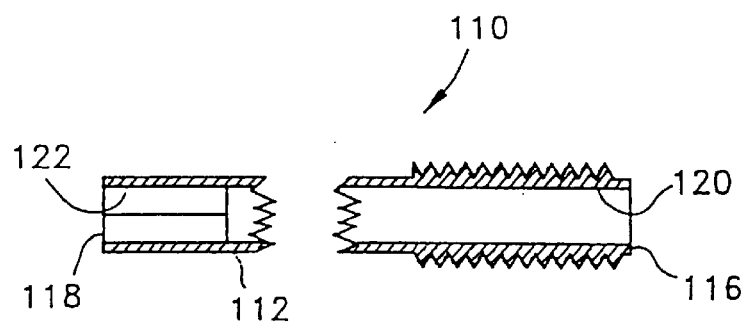
FIG. 30 is a longitudinal sectional view taken along line 30—30 of FIG. 28.

FIGS. 26 through 30 illustrate one form of a driver 110 for axially and appositively displacing the pins 60 (FIGS. 5 and 6) of the surgical anchor in opposite directions. As shown, driver 110 comprises an axially elongated member 112 having external threading 114 extending axially rearwardly from a leading end 116 toward a trailing end 118. The driver member 112 is formed from a material that is biocompatible with bone tissue or a substance that is preferably selected from the class comprised of: titanium, a titanium alloy, stainless steel, or a cobalt chromium alloy. It should be appreciated, however, that other unnamed materials would equally suffice without detracting or departing from the spirit and scope of the present invention. The outside diameter of the threading 114 of member 112 is such that it slidably fits endwise through the elongated bore 66 defined by insert 44 (FIGS. 5 and 6) and is accommodated for free turning movements in either rotational direction within the bore 66 of insert 44. Preferably, the external threading 114 on member 112 has a relatively fine pitch thereto. As shown in FIGS. 26, 28, 29 and 30, the member 112 preferably has an elongated bore 120 that opens to the leading and trailing ends 116 and 118 of member 112. The trailing end 118 of the member 112 is preferably configured to releasably accommodate a driving tool (not shown) capable of imparting turning movements to the driver 110. In a preferred form, and as shown in FIGS. 28 and 30, the trailing end 118 of member 112 is suitably configured with a socket-like opening 122 for releasably accommodating the distal end of a driving tool. In a most preferred form of the invention, and as shown in FIGS. 28 and 30, the socket or opening 122 has a hexagonal-like cross sectional configuration. It will be appreciated, however, that any suitable configuration, including a square or triangular configuration would equally suffice without detracting or departing from the spirit and scope of the present invention.

As will be described hereinafter in detail below, the driver 110 of mechanism 64 is operably associated with each pin 60 such that manipulation of the driver 110 results in positive endwise displacement of the pins 60 either toward an extended or retracted position depending upon the movements provided to the driver 110 of mechanism 64. In the illustrated form of the invention and returning to FIGS. 11 through 15, each pin or barb 60 preferably has an inner surface 124, which proximates the axis 52 (FIGS. 7 and 9) of the anchor 22 when the pins 60 are inserted within the insert 44, and an outer surface 126. As shown, in FIGS. 11 through 15, the inner surface 124 of each pin 60 has a series of vertically spaced serrations 128 thereon. The serrations 128 extend axially rearwardly from the leading end 74 and for a lengthwise distance toward the pointed end 76 of each pin 60. Notably, the serrations 128 on each pin 60 are configured for threadable engagement with the exterior threading 114 extending axially along the outer surface of driver 110. As such, the driver 110 is operably engaged or associated with each of the pins 60 of this surgical anchor assembly.

Figure 31:
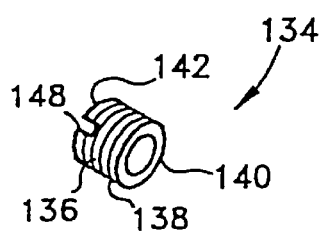
FIG. 31 is a perspective view of a limit stop forming part of the first embodiment of the present invention.
Figure 35:
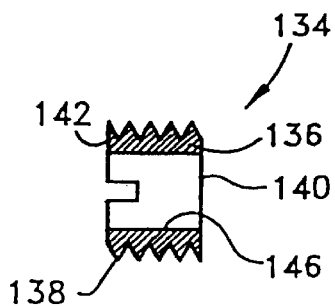
FIG. 35 is a sectional view taken along line 35—35 of FIG. 33.
Figure 33:
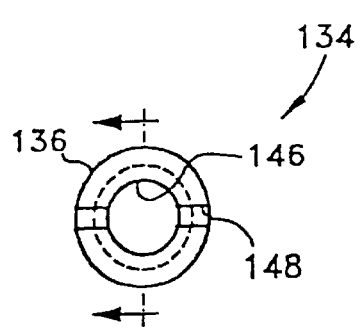
FIG. 33 is a left end elevational view of the limit stop illustrated in FIG. 32.
Figure 32:
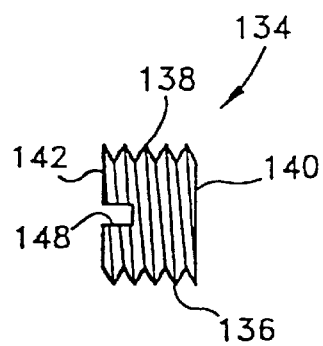
FIG. 32 is an enlarged side elevational view of the limit stop illustrated in FIG. 31.
Figure 34:
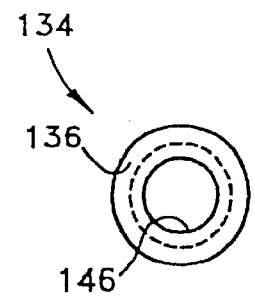
FIG. 34 is a right end view of the limit stop illustrated in FIG. 32.

As shown in FIGS. 5 and 6, mechanism 64 for positively displacing the pins 60 between retracted and extended positions and vice-versa, further includes a limit stop 134 for preventing axial displacement of the driver 110 when rotated. One form of the limit stop 134 is illustrated in FIGS. 31 through 35. Preferably, the limit stop 134 is formed from a material that is biocompatible with human bone tissue. In a most preferred form of the invention, the limit stop 134 is formed from a material chosen from the class comprised of: titanium, a titanium alloy, stainless steel, or a cobalt chromium alloy. It will be appreciated, however, that other materials would equally suffice without detracting or departing from the spirit and scope of the present invention. As shown in FIGS. 31 through 35, the limit stop 134 preferably includes a hollow member 136 with external threading 138 extending between leading and trailing ends 140 and 142, respectively, thereof. The external threading 138 has a relatively fine pitch which corresponds to the threading extending along the internally threaded portion 78 of insert 44 at the second end 48 of anchor 22. The trailing end 142 of the limit stop 134 is preferably configured to releasably accommodate a driving tool (not shown) capable of imparting turning movements to the limit stop 134. In a preferred form, and as shown in FIGS. 31, 32 and 33, the trailing end 142 of limit stop 134 is provided with an elongated slot 148 for releasably accommodating a distal end of the driving tool. Moreover, the limit stop 134 defines a throughbore 146 that opens to leading and trailing ends 140 and 142, respectively, of the limit stop and thereby allowing a tool to be passed endwise therethrough into operable engagement with the driver 110.

Figure 36:
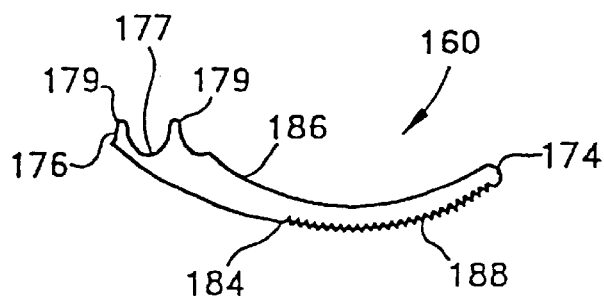
FIG. 36 is a view similar to FIG. 12 but showing an alternative form of pin or barb according to the present invention.
Figure 37:
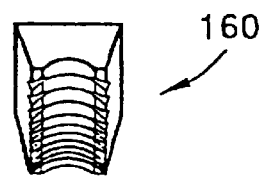
FIG. 37 is an enlarged right end elevational view of the pin or barb illustrated in FIG. 36.

An alternative form of pin 160 to be arranged in operable combination with the anchor 22 is shown in FIGS. 36 and 37. Pin 160 is substantially similar to pin 60 illustrated in FIGS. 11 through 15 and described in detail above. In the embodiment illustrated in FIGS. 36 and 37, each pin 160 has a leading end 174 and an opposite end 176. Intermediate its ends, each pin 160 preferably has a curvilinear or arcuate configuration. In the illustrated form of the invention, each pin has a curved arc with a predetermined radius that is substantially equal to the predetermined radius of each opening 170 formed in an insert 144 as shown in FIG. 38.

In the embodiment of the pin shown in FIG. 36, each pin 160 preferably forms an arc of about 80° between opposite ends thereof, and with the length of each pin being selected such that when the leading end 174 of the pin 160 is fully retracted within the fastener or anchor 22, the opposite end 176 of the pin or barb 160 will be positioned within the outside diameter of the insert 144.

In the illustrated embodiment shown, end 176 of each pin 160 is formed with a configuration that complements the configuration of the anchor or fastener 22. In the illustrated embodiment the end 176 of each pin 160 is formed with a channel 177 disposed between two substantially similar projections 179. As shown in FIG. 38, when the pin 160 is fully retracted the channel-like configuration and the projections 179 on opposite sides thereof blend into the outer threaded configuration extending axially along the fastener 22. It is to be appreciated that the length of each barb or pin 160 is sized such that when the pins 160 are displaced to their extended position, as shown in FIG. 39, the leading end 174 of each pin 160 remains operably associated with the mechanism 64 to allow for positive retraction of the pins 160 from their extended positions when desired or found necessary by the surgeon.

Figure 38:
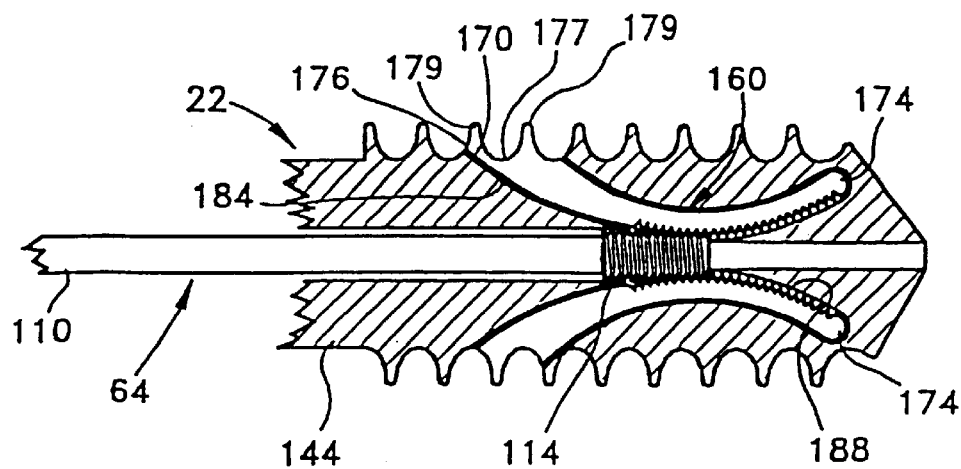
FIG. 38 is a view similar to FIG. 5 showing the alternative form of pins or barbs arranged in combination with the insert and in retracted positions relative thereto.
Figure 39:
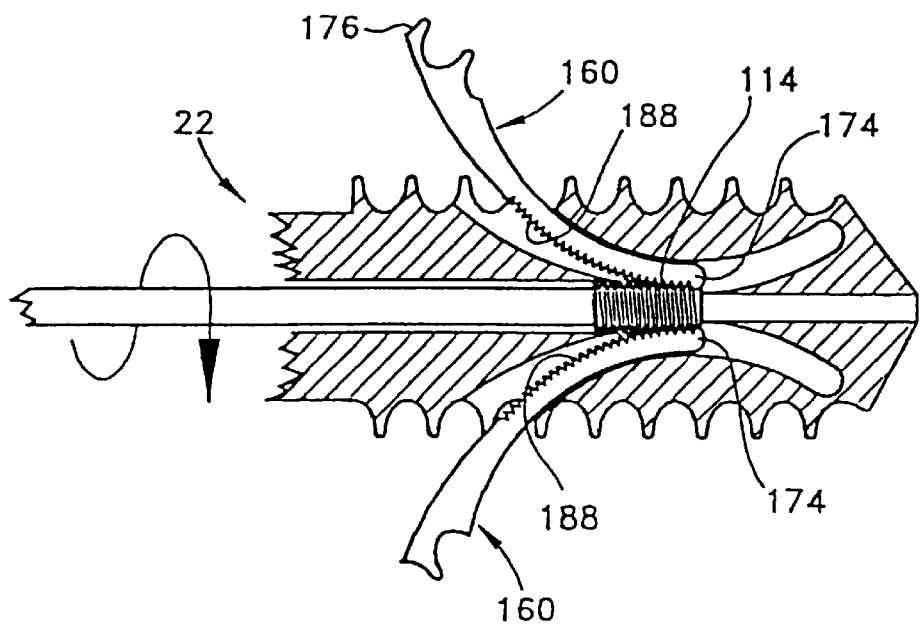
FIG. 39 is a view similar to FIG. 38 but showing the alternative form of the pins or barbs in an extended position.

As shown in FIG. 36, each pin or barb 160 preferably has an inner surface 184 which, as illustrated in FIGS. 38 and 39, proximates the axis 52 of the anchor when the pins are inserted within the insert 144 and an outer surface 186. The inner surface 184 of each pin has a series of spaced serrations 188 that extend axially rearwardly from the leading end 174 and for a lengthwise distance toward the second or other end 176 of each pin 160. The serrations 188 on each pin are configured for threadable engagement with the exterior threading 114 extending axially along the outer surface of driver 110 of mechanism 64 as described in detail above. As such, the driver 110 is operably engaged or associated with each of the pins 160 of this surgical anchor assembly.

Figure 40:
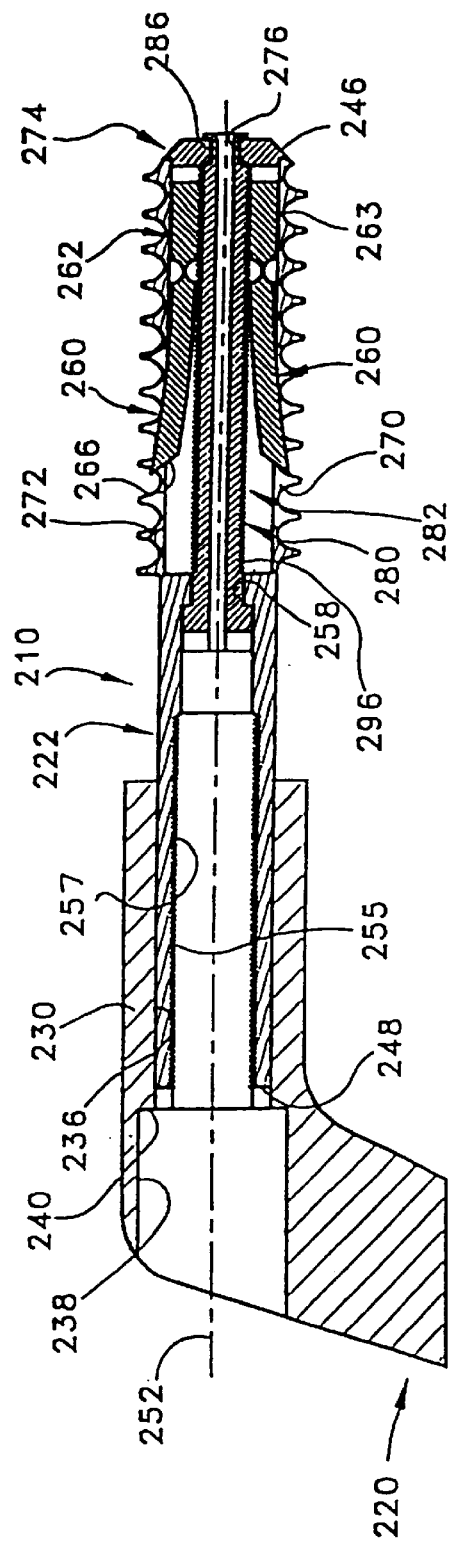
FIG. 40 is a view similar to FIG. 5 but showing a second embodiment of the present invention.
Figure 41:
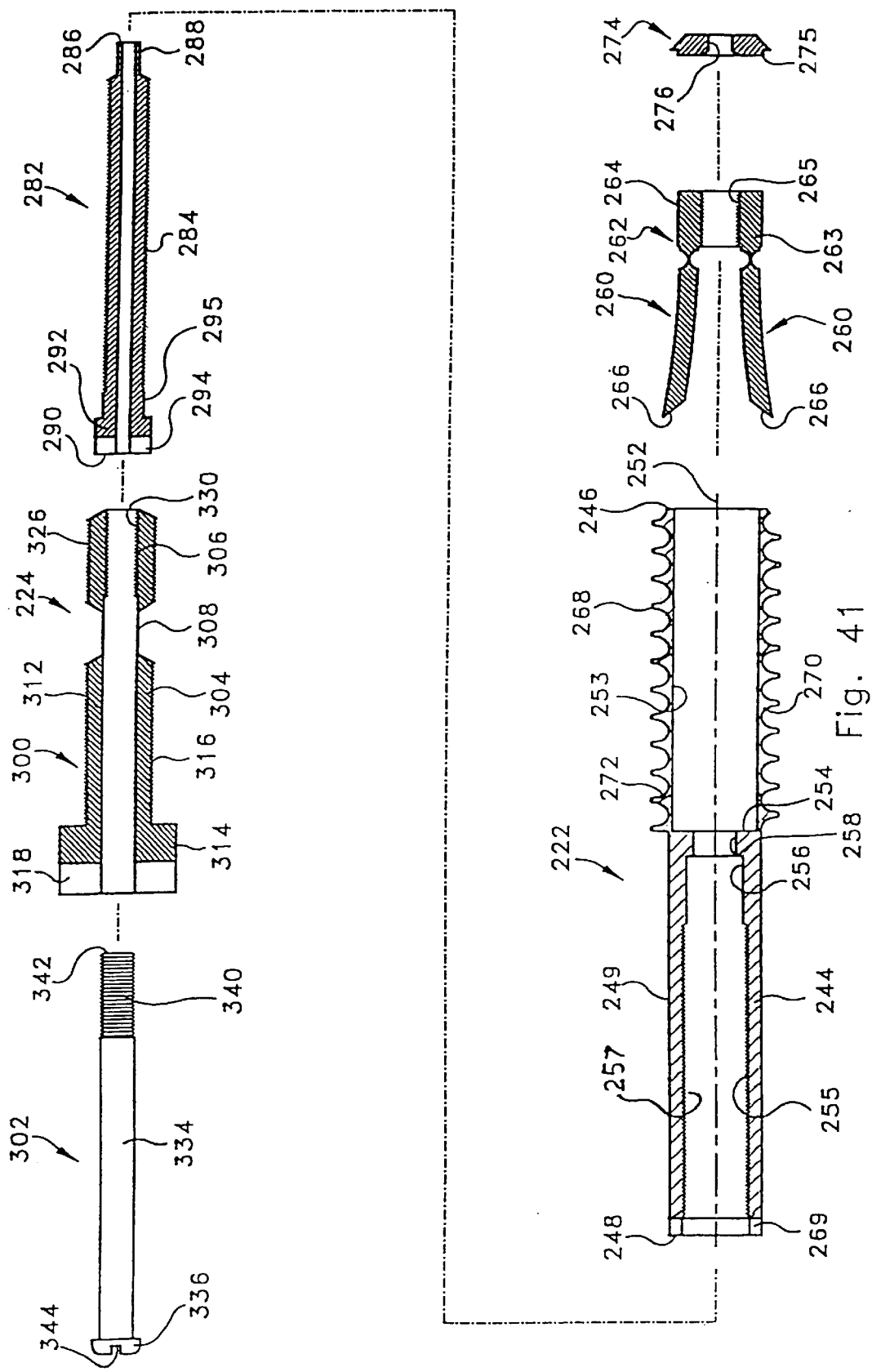
FIG. 41 is a longitudinal sectional view showing the components of the second embodiment of the present invention in exploded or disassembled relationship relative to each other.
Figure 54:
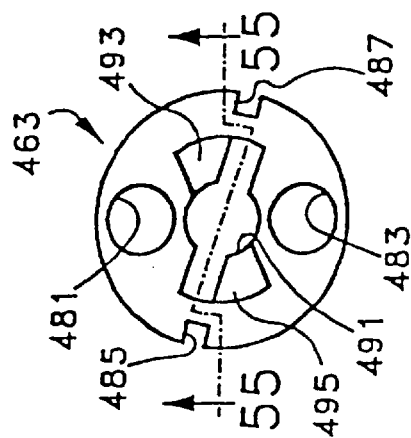
FIG. 54 is a right end view of the slide illustrated in FIG. 52.
Figure 55:
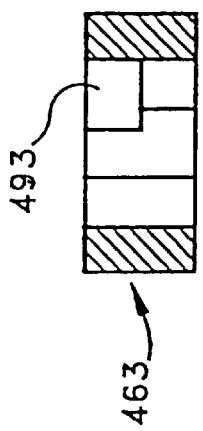
FIG. 55 is a sectional view taken along line 55—55 of FIG. 54.
Figure 52:
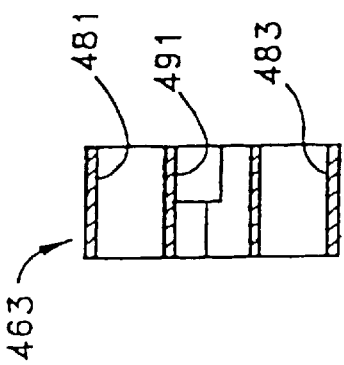
FIG. 52 is a sectional view of a slide forming a component part of the third embodiment of the present invention.
Figure 53:
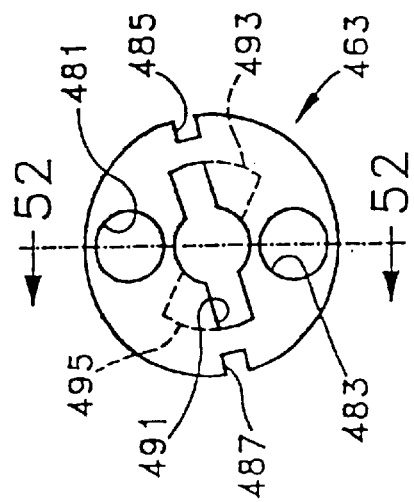
FIG. 53 is a left end view of the slide illustrated in FIG. 52.
Figure 61:
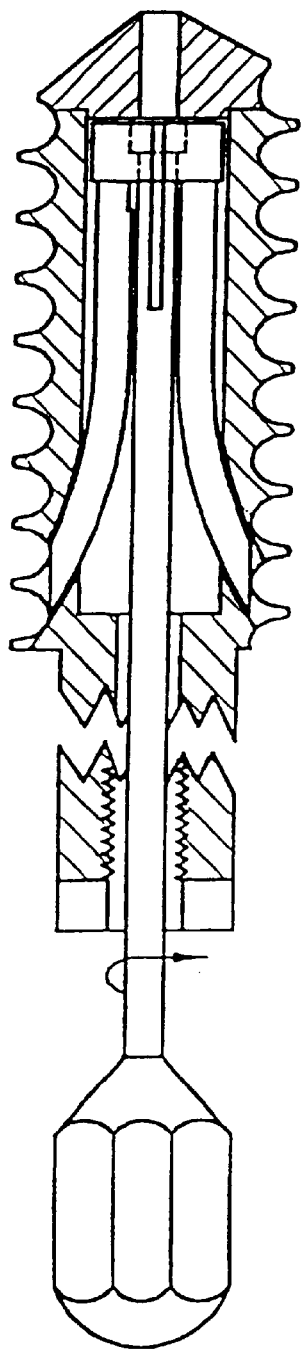
FIG. 61 is a sectional view showing the tool illustrated in FIGS. 59 and 60 arranged in operable combination with a slide assembly forming part of the third embodiment of the present invention and with the pins or barbs shown in retracted position relative to the anchor.

FIG. 40 schematically illustrates an alternative form for the surgical anchor assembly. This alternative form of the surgical anchor assembly is generally represented by reference number 210. As shown in FIG. 40, the surgical anchor assembly 210 includes a guide, generally represented by reference numeral 220 and an elongated anchor, generally represented by reference numeral 222. As shown in FIG. 41, and as will be discussed in detail below, the surgical fastener assembly 210 further includes a compressive fastener assembly 224 for holding the guide 220 in compressor relationship relative to the anchor 222.

The guide 220 is substantially similar to the guide 20 described in detail above and, thus, a detailed description need not be provided therefor. Suffice it to say, the guide 220 includes a hollow sleeve 230 that is substantially similar to the sleeve 30 discussed above. Sleeve 230 defines a throughbore 236 that is open at opposite ends thereof. The throughbore is provided with a counterbore portion 238 at one end thereof. In the illustrated embodiment, the counterbore 238 has a larger diameter than does the throughbore 236 and, thus, an annular or radial step 240 is defined therebetween.

The anchor 222 includes an elongated insert 244 having opposed first and second ends 246 and 248. The insert 244 is preferably formed from a material similar to that used to form insert 44. Insert 244 is sized such that when inserted within the bone, the first end 246 is disposed to one side of a fracture line while the second end 248 of the insert 244 is disposed to an opposite side of the fracture line.

Figure 42:
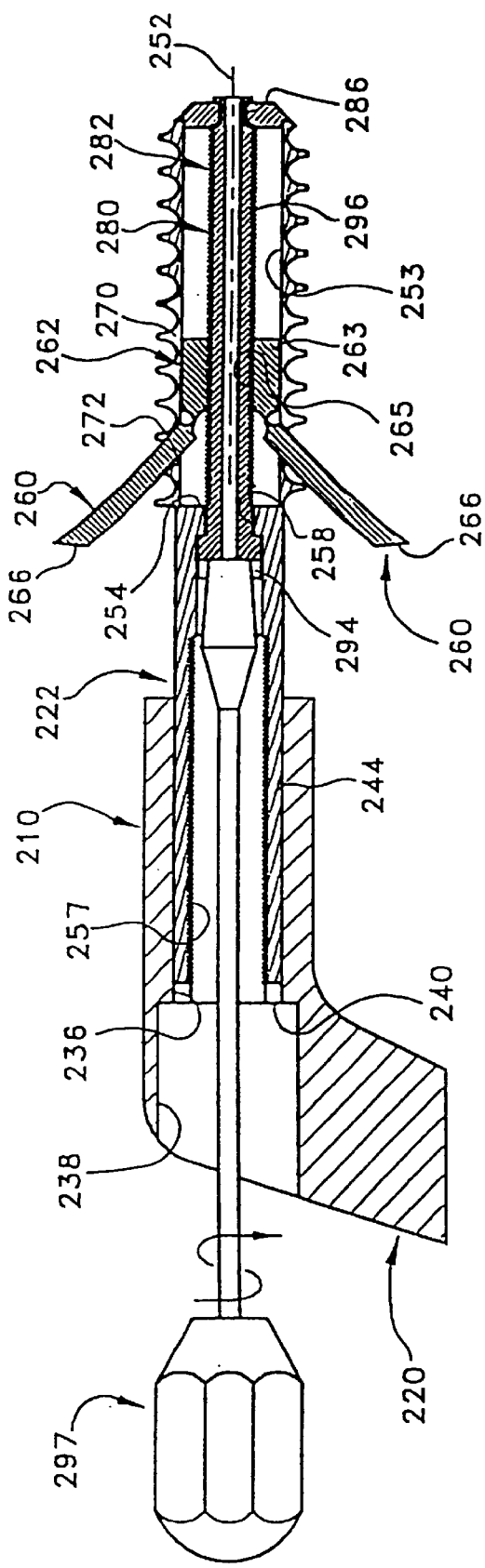
FIG. 42 is a view similar to FIG. 40 schematically illustrating distention of the pins or barbs relative to the anchor.

As shown in FIG. 40, the anchor 222 of the surgical fastener assembly 210 further includes a series of elongated pins or barbs 260 operably associated toward the first end 246 of the insert 244 for movement between a retracted position (FIG. 40) and a radially extended position (FIG. 42). As shown, the pins 260 arc carried by the insert 244 for endwise and radial displacement relative thereto. In the illustrated embodiment of the invention, four pins 260 are equidistantly spaced relative to each other for positive endwise movement in opposite directions between the retracted and extended positions shown in FIGS. 40 and 42, respectively.

As will be appreciated by those skilled in the art, the exterior configuration of the insert 244 can take a myriad of shapes and forms. According to the present invention, and as illustrated in FIG. 41, the elongated insert 244 preferably has external threading 268 axially extending therealong and leading rearwardly from the first end 246 thereof. The external threading 268 along the exterior of insert 244 has a relatively coarse pitch to enhance the purchasing ability and the anchorage of the anchor 222 within the substance of the bone in response to turning movements being imparted to the anchor 222.

Extending axially forward from the second or trailing end 248, the insert 244 of anchor 222 has a constant generally cylindrical-like configuration 249 extending to the terminal end of the exterior threading 268 and having a slightly smaller outside diameter than that of the exterior threading 268. Notably, the cylindrical-like configuration 249 extending axially forward from the terminal end 248 of the insert 244 has a diameter which is generally equal to the diameter of the throughbore 236 in the guide 220 thereby facilitating sliding movement of the anchor 222 axially within the sleeve 230 of the guide 220. Although not specifically shown, as is conventional, cooperative instrumentalities are defined on the sleeve 230 of guide 220 and on the insert 244. As mentioned above, the purpose of the cooperative instrumentalities is to allow for axial movement of the anchor 222 relative to the sleeve 230 along an axis 252 defined by the insert 244 while preventing rotational movement of the sleeve 230 relative to the anchor 222.

As shown in FIG. 41, insert 244 defines a constant diameter counterbore portion 253 extending axially inward from the first end 246 of insert 244. At an inner end, the counterbore portion 253 defines a radial wall 254. Between end 246 and wall 254, the insert 244 further defines a series of axially elongated openings arranged in spaced circumferential relation relative to each. In the illustrated form of the invention, insert 244 is provided with four openings 270. Each opening 270 intersects with and opens to the counterbore 253 defined by insert 244. As shown in FIG. 41, an axially inward portion 272 of each opening 270 has an inwardly slanted surface for purposes to be described in detail hereinafter.

At an opposite end of the insert 244, another elongated bore 257 having an internally threaded portion 255 and a counterbore portion 256. The internally threaded portion 255 extends inwardly from the second or trailing end 248 of the insert. Preferably, the internally threaded portion 255 of bore 257 has a relatively fine pitched threading extending therealong. Notably, the internally threaded portion 255 has a larger diameter than does counterbore portion 256. The insert 244 further defines a passage 258 extending between counterbore portions 253 and 256.

As shown in FIG. 41, the second or trailing end 248 of the insert 244 is furthermore configured to releasably accommodate a driving tool (not shown) capable of the parting tuning movements to the anchor 222. In a preferred form, and as shown in FIG. 41, the trailing or second end of the insert 244 is suitably configured with a slot-like opening 269 for releasably accommodating a distal end of a driving tool. It will be appreciated, however, that any suitable configuration would equally suffice without detracting or departing from the spirit and scope of the present invention.

As shown in FIG. 41, the pins or barbs 260 in this form of the invention form part of a carrier assembly 262. Carrier assembly 262 preferably includes a slide 263 to which one end of each pin 260 is articulately connected to allow the pins 260 to flex or hingedly move relative to the slide while remaining operably connected thereto. As shown, slide 263 has an outer surface configuration 264 having a diameter substantially equal to the diameter of the counterbore portion 253 defined by the insert 244. Slide 263 further defines a threaded opening 265 having a relatively fine pitched internal threading extending therealong. Notably, the free ends of the pins 260 are biased to spring outwardly away from the axis 252. Moreover, the free end of each pin 260 has a cam-like surface 266 thereon for purposes to be described in detail hereinafter.

As shown in FIG. 40, the carrier assembly 262 fits axially within bore 253 defined by insert 244 for axial movement and with the pins 260 extending toward the second end 248 of insert 244. After fitting the carrier assembly 262 within bore 253 of insert 244, the open end of insert 244 is closed by an end cap 274.

As shown in FIG. 41, end cap 274 preferably includes a reduced annular portion 275 sized to snugly fit within the free open end of bore 253 defined by insert 244. Suitable retaining means, such as welding, or staking, or the like securely fastens the end cap 274 to the remainder of the insert 244. End cap 274 is preferably formed form a material that is biocompatible with bone tissue or human substance and is preferably selected from the class comprised of: titanium or titanium alloy, stainless steel, or cobalt chromium alloy. It would be appreciated, however, that other unnamed materials would equally suffice without detracting or departing from the spirit or scope of the present invention. As shown in FIG. 41, the end cap 274 defines a central throughbore or hole 276 extending therethrough. Moreover, the annular or circumferential surface of end cap 274 is preferably chamfered to promote insertion of the anchor 222 into the bone.

Returning to FIG. 40, when the carrier assembly 262 is mounted within bore 253 of insert 244, the pins 260 tend to bias outwardly. The slots or opening 270 in the insert 253 are elongated such that a distal end of each pin 260 tends to project radially outwardly into the slot 270 with the slanted surface 266 being advantageously arranged to engage and cooperate With slanting surface 272 on each opening 270 in a manner forcibly projecting the pins 260 radially outwardly as shown in FIG. 42.

The mechanism 280 for positively displacing the pins 260 in opposite directions between retracted and extended positions (FIGS. 40 and 42, respectively) will now be described. The drive mechanism 280 preferably includes a manually operated driver 282 arranged in operative relation with the carrier assembly 262. As will be described below, manual activation of the drive mechanism 280 will affect axial displacement of the carrier assembly 262 within bore 253 of insert 244 thereby effecting positive displacement of the pins 260 with the carrier assembly 262.

Turning to FIG. 41, driver 282 preferably includes an axially elongated and hollow member 284 having a reduced diameter portion 286 axially projecting rearwardly from a first end 288 thereof. The driver 282 is formed from a material that is bio-compatible with bone tissue or human substance and is preferably selected from the class comprised of: titanium, titanium alloy, stainless steel, or cobalt chromium alloy. Of course, other unnamed materials will equally suffice without detracting or departing from the spirit and scope of the present invention. The reduced diameter portion 286 of member 284 has a diameter equal to the diameter of bore 276 defined by end cap 274. At a second end 290, driver 282 has an enlarged head portion 292. In a preferred form, and as shown in FIG. 41, the second end 290 is configured to releasably to accommodate a distal end of a driving tool. In a most preferred form of the invention, the second or terminal end 290 of driver 282 is provided with an elongated slot 294 that is configured to releasably accommodate a driving tool. Axially spaced inwardly from the terminal end 290 thereof, the driver 282 is provided with an axially extended shoulder 295. Between the shoulder and the reduced diameter portion 286, the driver 282 is provided with external threading 296. The external threading extending lengthwise along the driver 282 has a relatively fine pitch that corresponds to the internally threaded portion 265 of slide 263 forming part of the carrier assembly 262. Notably, the reduced diameter portion 286 and the externally threaded portion 296 of driver 282 are sized to permit their endwise insertion through passage 258 defined by insert 244. Moreover, the shoulder portion 295 has a diameter that is substantially equal to the passage 258 and is journalled thereby. Moreover, the enlarged head portion 292 is specifically sized with the diameter greater than the passage 258 thereby preventing axial displacement or movement of the head portion 292 past the passage 258.

During assembly of the surgical fastener assembly 210, the reduced diameter portion 286 and externally threaded portion 296 are passed endwise through the passage 258 defined in the insert 244 of anchor 222. The threaded portion 296 of driver 282 is likewise threadably engaged with the slide 263 of carrier assembly 262 to allow the reduced diameter portion 286 to pass endwise through and be journalled by the periphery of the bore 276 defined by end cap 274. The reduced diameter portion 286 is sized to allow a lengthwise portion thereof to pass endwise through and beyond the end cap 274. That free end of the reduced diameter portion 286 is thereafter swaged or flared outwardly thus preventing axial displacement of the driver 282 in response to rotational movement being imparted thereto.

Turning to FIG. 42, the pins 260 of carrier assembly 262 are radially and positively displaced in opposite directions relatively to axis 252 in response to and as a function of rotation of driver 282. As shown, a suitable tool 297 is displaced endwise through bore 236 of guide 220 and through the bore 257 of insert 244 into operable engagement with the slot 294 at the second end 290 of driver 282. Thereafter, rotation of the driver 282 will result in axial or endwise displacement of the slide 263 as a result of the threaded interconnection between the internal threading 265 on slide 263 and the external threading 296 on driver 282. As will be appreciated, and as the pins 260 are drawn toward the radial wall 254 of bore 253, the slanted surface configurations 266 thereon engage the outwardly slanting surfaces 272 of the openings thereby forcibly propelling the pins radially outwardly relative to the axis 252. As will be appreciated, rotation of the tool 297 in the opposite direction will likewise result in axial displacement of the carrier assembly 262 but in a direction opposed from that earlier discussed. As a result, the turning or rotation of the driver 282 will affect retraction of the pins 260 as the slide assembly 262 is moved in a direction toward the end cap 274.

Another aspect of the present invention relates to the surgical anchor assembly 210 having a compressive screw assembly 224 for maintaining the guide 220 and anchor 222 in compressive relationship relative to each other as by axially fixing the guide 220 to the anchor 222. In that embodiment shown in FIG. 41, the compression screw assembly 224 preferably includes a compression screw 300 and a driver 302. Both the compression screw 300 and driver 302 are formed from a material that is bio-compatible with bone tissue or human substance material and is preferably selected from the class comprised of titanium, a titanium alloy, stainless steel, or cobalt chromium alloy.

As shown in FIG. 41, the compression screw 300 is provided with first and second interconnected sections 304 and 306. The sections 304 and 306 of compression screw 300 are joined or interconnected to each other by a collapsible section 308 that transmits rotation and torque between the sections 304 and 306. The first section 304 of compression screw 300 is provided with an elongated shank portion 312 and an enlarged head portion 314. The shank portion 312 of the first section 304 is provided with external threading 316 therealong. The external threading 316 has a relatively fine pitch that corresponds to the internal threading 255 extending along the bore 257 of insert 244. As shown in FIG. 43, the enlarged head portion 314 of the first section 304 of screw 300 has a diameter slightly smaller than the diameter of the counterbore 238 defined by guide 220. Notably, the head portion 314 of screw 300 is preferably configured to releasably accommodate a driving tool capable of imparting turning movements to the screw section 304.

In a preferred form, and as shown in FIG. 41, the trailing end of screw section 304 is configured with a slot 318 for releasably accommodating a distal end of a driving tool. Notably, the first section 304 of screw 300 is fixed to the collapsible section 308 such that turning movements imparted to screw section 304 will likewise be imparted to the collapsible section 308.

The second screw section 306 is likewise connected to the collapsible section 308 in axially spaced relation relative to screw section 304. As shown, screw section 306 includes external threading 326 extending along the length thereof. Notably, the external threading 326 on screw section 306 is identical to the external threading 3 16 on screw section 304.

The collapsible section 308 serves to transfer the motion of screw section 304 to screw section 306. Moreover, the second screw section 306 defines an internally threaded portion 330 extending therealong. The threaded portion 330 of the second screw section 306 has a relatively fine pitched threading extending therealong. Notably, however, the threading extending along portion 330 is left-handed threading while the external threading 316 and 326 on screw portions 304 and 306, respectively, is right handed. As will be appreciated, the threading along screw portion 330 and 316, 326 can be right handed and left handed, respectively, without detracting or departing from the spirit and scope of the present invention. The important aspect to note is that the threading along portions 330 and 316, 326 are reversed from each other.

As shown in FIG. 41, the driver 302 of compression screw assembly 224 comprises a shank portion 334 and an enlarged head portion 336. The shank portion 334 of driver 302 has a diameter sized to allow the shank portion 334 to slidably to fit endwise into and through the central interior of screw 300. The shank portion 334 of driver 302 includes external threading 340 axially extending from a free end 342 of the driver 302. The head portion 336 of driver 302 is sized to prevent it from passing through the interior of screw 300. As will be appreciated, the axial length or distance separating head portion 336 of screw 302 from the free end 342 thereof is about equal to the distance separating the head portion 314 of screw 300 from the beginning portion of the interior threading 330 most closely adjacent the head portion 314.

In a preferred form, and as shown in FIG. 41, the trailing end of the head section 336 of driver 302 is configured with a slot 344 for releasably accommodating the distal end of a driving tool. As will be appreciated, configurations other than a slot would equally suffice without detracting or departing from the spirit and scope of the present invention.

During assembly of the surgical fastener assembly 210, and as shown in FIG. 43, the compressive screw 300 of the compressive screw assembly 224 is rotatably threaded into engagement with the internal threading 255 of the insert 244. A suitably configured tool 355 engages with the slot 318 and the head portion 314 of the screw 300 to drivingly rotate the first and second sections 304 and 306 of the screw 300 until the enlarged head 314 abuts the radial wall 240 defined by the counterbore 238 defined by the guide 220. Thereafter, the driver 302 is operably engaged with the screw 300. That is, and is shown in FIG. 44, the driver 302 is inserted through the central opening defined by the screw 300 into threaded engagement with the internal threading 330 of the second section 306 of screw 300. Notably, however, the driver 302 is turned in a direction opposed from that in which the screw 300 was rotated for insertion into the anchor. In this regard, a suitable tool 357 releasably engages with the slot 344 in the head region 336 of the driver 302 to rotate the driver 302. Rotation of the driver 302 is affected until the section 308 joining sections 304 and 306 collapses. The collapse of the center section 308 causes opposing forces to act against the external threading on sections 304, 306 and the internal threading 330 thereby preventing the compressive screw assembly 224 from inadvertently turning relative to the anchor 222.

FIG. 45 schematically illustrates an alternative form of anchor, generally represented by reference to numeral 422 that can be used as part of the surgical anchor assembly. The anchor 422 includes an elongated insert 444 having opposed first and second ends 446 and 448. The insert 444 is preferably formed from a material similar to that used to form insert 44. Insert 444 is sized such that when inserted within the bone, the first end 446 is disposed to one side of a fracture line while the second end 448 of the insert 444 is disposed to an opposite side of the fracture line.

Figure 63:
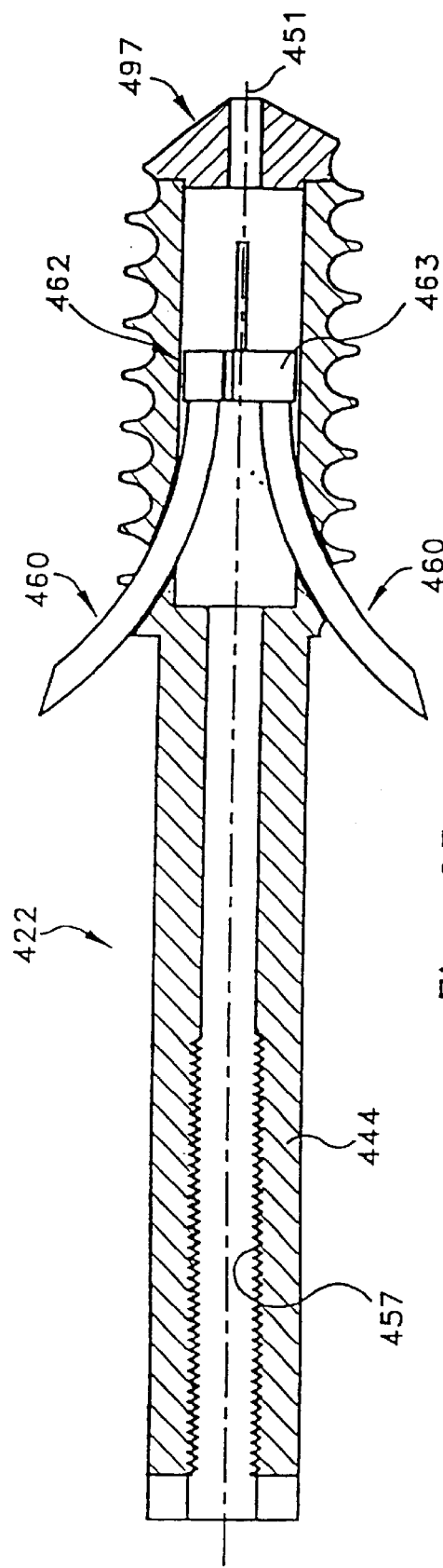
FIG. 63 is a longitudinal sectional view similar to FIG. 45 but showing the pins arranged in an extended relationship relative to the anchor.

As shown in FIGS. 45 and 46, the anchor 422 of the surgical fastener assembly further includes a series of elongated pins or barbs 460 operably associated toward the first end 446 of the insert 444. As shown in FIGS. 45 and 63, the pins or barbs 460 are operably associated with the anchor 422 for movement between a retracted position (FIG. 45) and a radially extended position (FIG. 63). As shown, the pins 460 are carried by the insert 444 for endwise and radial displacement relative thereto. In the illustrated embodiment of the invention, two pins 460 are carried by the anchor 422 in diametrically opposed relation relative to each other for positive endwise movement in opposite directions between the retracted and extended positions shown in FIGS. 45 and 63, respectively.

According to this aspect of the present invention, and as illustrated in FIGS. 46 and 47, the elongated insert 444 preferably has external threading 468 axially extending there along and leading rearwardly from the first end 446 thereof. The external threading 468 along the exterior of insert 444 has a relative coarse pitch to enhance the purchasing ability and the anchorage of the anchor 422 within the substance of the bone in response to turning movements being imparted to the anchor 422.

Extending axially forward from the second or trailing end 448, the insert 444 of anchor 422 has a constant generally cylindrical-like configuration 449 extending to the terminal end of the exterior threading 468 and having a slightly smaller outside diameter then that of the exterior threading 468. Notably, the cylindrical-like configuration 449 extending axially forward from the terminal end 448 of the insert 444 has a diameter which is generally equal to the diameter of the throughbore 36 (FIG. 2) in the guide operably associated therewith thereby facilitating sliding movement of the anchor 422 axially within the sleeve of the guide. Although not specifically shown, and as is conventional, cooperative instrumentalities are defined on the exterior configuration 449 of the insert 444 and of the respective guide to allow for axial movement of the anchor 422 relative to the guide along an axis 451 defined by the insert 444 while preventing rotational movement of the anchor 422 relative to the respective guide.

As shown in FIG. 47, insert 444 defines a constant diameter counterbore portion 452 extending axially inward from the first end 446 of insert 444. At an inner end, the counterbore portion 452 defines a radial wall 454. Between end 446 and wall 454, the insert further defines a pair of slanted openings 470 arranged in diametrically opposed relation relative to each other. Each opening intersects with and opens to the counterbore 452 defined by insert 444. Moreover, each opening 470 opens to the exterior of insert 444.

Extending axially forwardly from the second or opposed end 448, the insert 444 defines an elongated bore 455 that opens to the counterbore portion 452. Extending inwardly from the second end 448, bore 455 includes an internally threaded portion 457. Preferably, the internally threaded portion 457 of bore 455 has a relatively fine pitched threading extending therealong. As should be appreciated, the internal threading 457 corresponds to the external threading on the compressive screw assembly (not shown) arranged in operable combination with the insert 444.

As shown in FIG. 47, the second or trailing end 448 of insert 444 is furthermore configured to releasably accommodate a driving tool (not shown) capable of imparting turning movements to the anchor 422. In a preferred form, and as shown, the trailing or second end 448 of the insert 444 is suitably configured with a slot-like opening 469 for releasably accommodating a distal end of a driving tool. It will be appreciated, however, that any suitable configuration would equally suffice without detracting or departing from the spirit and scope of the present invention.

Turning to FIG. 49, the insert 444 is further provided with a suitable guide mechanism 475 for purposes to be described hereinafter. The guide mechanism 475 can take a myriad of different forms without detracting or departing from the spirit and scope of the present invention. One form of guide mechanism 475 is schematically illustrated in FIG. 49. In the illustrated embodiment, the guide mechanism 475 includes a pair of diametrically opposed guide keys 477 and 479 that extend along a lengthwise portion of the counterbore 452 defined by insert 444. As shown in FIG. 49, the guide keys 477 and 479 project radially inwardly toward each other. Notably, the distal end of each guide key 477 and 479 terminates short of the first end 446 of the fastener 444 such that there is an axial space between the terminal end of the guide of each guide key 477, 479 and the first end 446 of the insert 444.

Returning to FIG. 45, the pins or barbs 460 in this form of the present invention form part of a carrier assembly 462. Carrier assembly 462 preferably includes a slide 463 to which one end of each pin is fixedly connected such that the pins 460 will positively move upon axial movement of the slide 463 within the counterbore 452 of insert 444.

Turning to FIGS. 46, 50 and 51, each pin 460 has a flexible wire-like configuration shaped to slidably fit endwise within and through a respective one of the openings 470 defined in the insert 444. Suffice it to say, each pin 460 is provided with sufficient strength so as to allow for insertion in and through the bone tissue without substantially bending intermediate opposite ends thereof. In a most preferred form of the invention, each pin 460 is formed from a material selected from the class comprised of: titanium, a titanium alloy, stainless steel, or cobalt chromium alloy.

In the embodiment illustrated in FIGS. 46, 50 and 51, each pin 460 has a leading end 461 and an opposite pointed end 466. Toward end 466, each pin preferably has a curvilinear or arcuate configuration such that the free ends 466 extend into and through the opening 470. The length of each pin 460 is selected such that when the leading end 461 of the pin 460 is fully retracted within the anchor 422 (FIG. 45) the opposite pointed end 466 of the pin or barb 460 will be positioned within the outside diameter of the insert 444 to facilitate insertion of the surgical anchor assembly within the bone of the patient. Moreover, it is to be appreciated that the length of each barb or pin 460 is sized such that when the pins are displaced to their extended position (FIG. 63) the leading end 461 of each pin 460 remains operably associated with the carrier assembly 462 to allow for positive retraction of the pins 460 from their extended positions when desired or found necessary by the surgeon.

Figure 62:
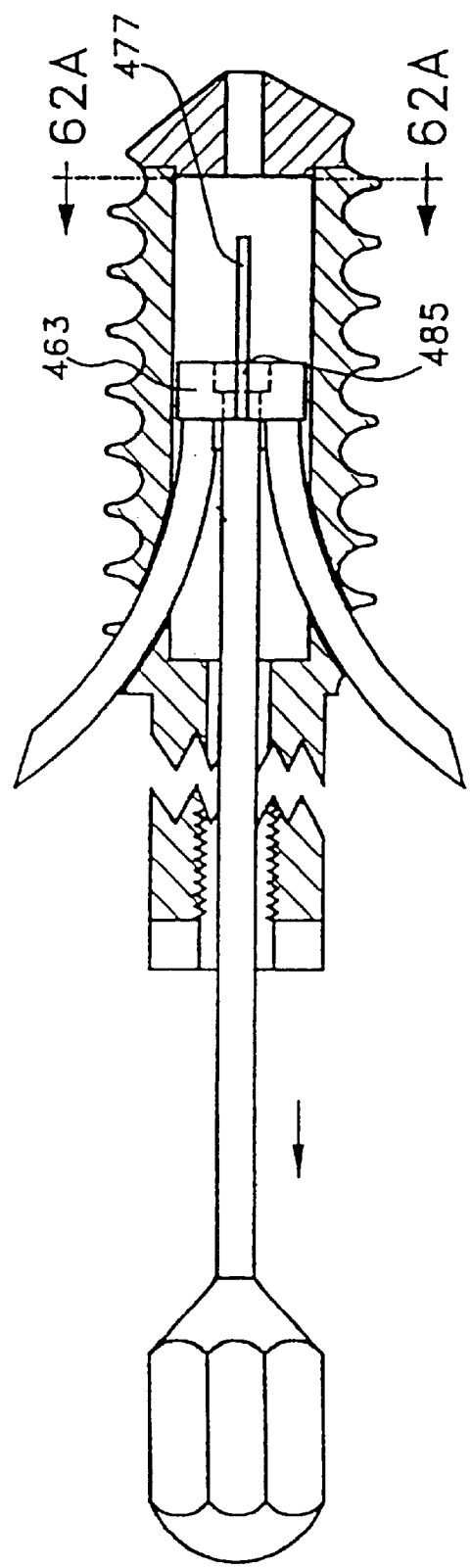
FIG. 62 is a view similar to FIG. 61 but showing the tool in operable relationship with the slide of the slide assembly for forcibly extending the pills or barbs radially outwardly from the anchor.

As mentioned, the carrier assembly 462 further includes a slide 463. The configuration of the slide 463 is illustrated in FIGS. 52 through 55. As shown, slide 463 has a generally cylindrical outer surface configuration having a diameter substantially equal to the diameter to the counterbore portion 452 (FIG. 46) of fastener 444. Slide 463 defines an identical pair of throughbores or openings disposed in diametrically opposed relation relative to each other. The diameter of the openings 481, 483 are sized to receive the end 461 of pin 460 and to allow the ends 461 of each pin 460 to be rigidly secured thereto. Additionally, the slide 463 defines a pair of diametrically opposed slots 485 and 487 that are arranged in other than a normal relation relative to the openings 481 and 483. Notably, the slots 485, 487 are sized to facilitate guided movement of the slide 463 relative to the guide keys 477 and 479 on the insert 444 (FIG. 62). Moreover, the slide 463 defines a tool engagement cavity 491 that passes endwise through the slide and has recesses 493 and 495 on opposite sides thereof.

As shown in FIG. 45, the carrier assembly 462 fits axially within the bore 452 defined by insert 444 for axial movement and with the pointed ends 466 of each pin 460 extending at least partially through the opening 470, but not beyond the periphery of fastener 444. After fitting the carrier assembly 462 within the bore 452 of insert 444, the open end of insert 444 is closed by an end cap 497.

A preferred form of end cap 497 is illustrated in FIGS. 56, 57 and 58. As shown, end cap 497 preferably includes a reduced annular portion 498 sized to snugly fit within the free open end of bore 452 defined by insert 444. Suitable retaining means such as staking, welding or the like securely fastens the end cap 497 to the remainder of the insert 444. End cap 497 is preferably formed from material that is biocompatible with bone tissue or a human substance and is preferably selected from the class comprised of: titanium, a titanium alloy, stainless steel, or cobalt chromium alloy. Other unnamed materials would equally suffice, however, without detracting or departing from the spirit or scope of the present invention. As shown in FIGS. 56 through 58, the end cap 497 defines a central throughbore or hole 499. Moreover, the exposed surface of end cap 497 is preferably chamfered to promote insertion of the anchor 422 into the bone.

FIGS. 59 and 60 schematically illustrate a tool that is configured to cooperate with and axially move the carrier assembly 462 in opposite directions within the bore 452 of the insert 444 whereby positively moving the pins 460 between retracted (FIG. 45) and extended (FIG. 63) positions. The tool 500 preferably includes an elongated shank 502 having axially spaced keys 504 and 506 at a distal end thereof. The shank 502 and keys 504 and 506 are configured to axially fit endwise within the bore 455 of insert 444 and extend into operable combination within the slide 463 of the carrier assembly 462. More specifically, the key 506 is specifically configured to fit endwise through the tool engagement cavity 491 such that the key 506 can operably engage with the surfaces 493 and 495 on the slide.

As shown in FIG. 45, guide slots 485 and 487 in the slide 463 are not axially aligned with the guide keys 477 and 479 extending radially inwardly from the bore 452. As will be appreciated by those skilled in the art, the guide keys 477 and 479 are radially offset from the guide slots 485 and 487, respectively, under the influence of the disposition of the pins 460 and their orientation relative to the guide slots 485 and 487. Accordingly, the slide assembly 462 cannot be inadvertently displaced axially within the bore 452 and the pins 460 remain in the retracted positions.

Figure 62A:
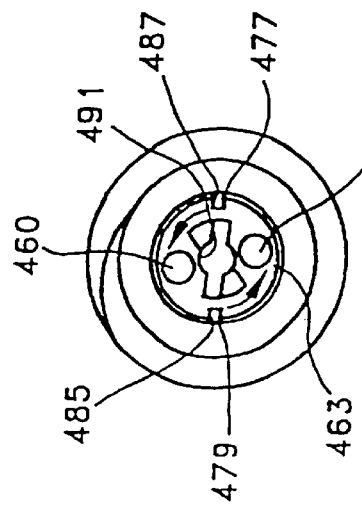
FIG. 62A is a sectional view taken along line 62A—62A of FIG. 62.
Figure 61A:
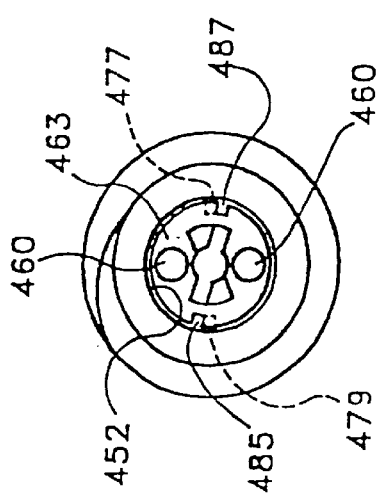
FIG. 61A is a sectional view taken along line 61A—61A of FIG. 45.

To affect extension of the pins or barbs 460 radially outwardly from the bore 52 of the fastener 444, the tool 500 is inserted through the fastener 444. More specifically, the keys are endwise inserted through the insert 444 and allow to pass into operable engagement with the slide. After moving the keys 504 and 506 into operable engagement with the slide, the tool 500 is rotated to effect rotation of the slide 463 as shown in arrows and FIGS. 62 and 62A. Rotation of the slide 463 is permitted by the resiliency of the length of the pins 460. The slide 463 is rotated until the slots 485 and 487 are aligned with the guide keys 477 and 479 and thereafter the tool 500 is moved to the left as shown in FIG. 62 to forcibly propel the pins 460 outwardly relatively to the insert 444 thereby enhancing securement of the surgical anchor 422 into the bone. When desired, the tool may also be used in operable engagement with the slide 462 to forcibly retract the pins 460 to the position shown in FIG. 45. That is, the keys are rearranged in operable engagement with the slide 463 and the tool 500 is pushed and turned or rotated to forcibly retract the pins to facilitate removal of the anchor assembly when necessary or desired by the surgeon.

Still another alternative form of compression screw assembly, generally represented by reference numeral 600, is illustrated in FIGS. 64 and 64A. The purpose of the compression screw assembly 600 is to maintain a guide 620 and anchor 622 in compressive relationship relative to each other as by fixing the guide 620 to the anchor 622. For purposes of this description, the guide 620 and anchor 622 are substantially similar to the guide 20 and anchor 22 described above. Thus, no further detailed description need be provided therefore at this time.

The compressive screw assembly 600 preferably includes a compression screw 630 and a driver 650. Both the compression screw 630 and driver 650 are formed from a material that is biocompatible with bone tissue or human substance.

Figure 65:
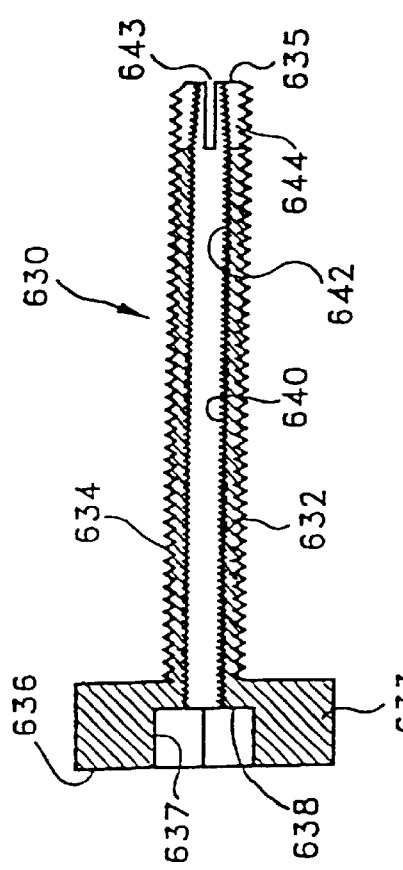
FIG. 65 is a longitudinal sectional view of a compression screw forming a component part of the compression screw assembly illustrated in FIGS. 64 and 64A.

As shown in FIG. 65, the compression screw 630 is provided with an elongated shank portion 632 and an enlarged head portion 633. The shank portion 632 of the compression screw 630 is provided with external threading 634 extending axially from a leading end 635 of the screw 630. The external threading 634 has a relatively fine pitch that corresponds to internal threading extending axially along an internally threaded bore 678 of anchor 622. The enlarged head portion 633 of screw 630 has a diameter slightly smaller than the diameter of a counterbore 688 formed in guide 620 and which is substantially similar to counterbore 38 in guide 20 (FIG. 2).

Figure 66:
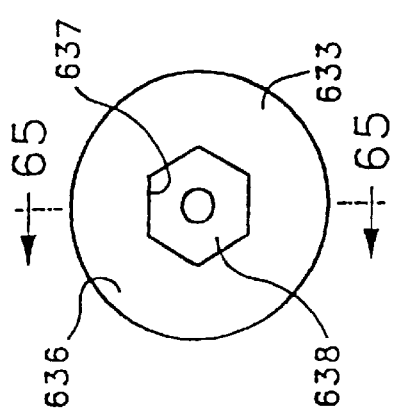
FIG. 66 is a left end elevational view of the compression screw illustrated in FIG. 65.

As shown in FIGS. 65 and 66, a trailing end 636 of screw 630 is preferably configured to releasably accommodate a driving tool (not shown) capable of imparting turning movements to the screw 630. In a preferred form, and as shown, the trailing end 636 of screw 630 is configured with a socket-like opening 637 having a bottom 638. The socket-like opening 637 is configured to releasably accommodate a distal end of a driving tool. In a most preferred form of the invention, and as shown, the socket or opening 637 has a hexagonal-like cross-sectional configuration. It will be appreciated, however, that any suitable configuration including an elongated slot would equally suffice without detracting or departing from the spirit and scope of the present invention.

Figure 67:
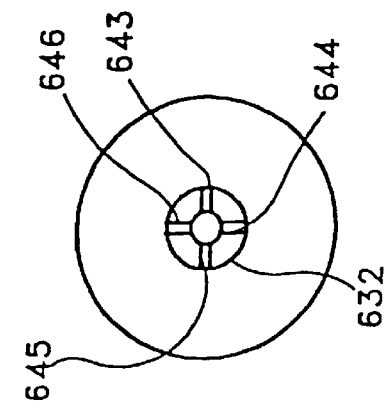
FIG. 67 is a right end elevational view of the compression screw illustrated in FIG. 65.

The screw 630 furthermore defines an elongated bore 640 that opens at opposite ends to the socket 637 and the leading end 635 of screw 630. As shown, the opening 640 has internal threading 642 extending along the length thereof. As shown in FIGS. 65 and 67, the distal or leading end 635 of the screw 630 is provided with a series of radial through slots 643, 644, 645, and 646 that are arranged in generally normal relation relative to each other and which extend axially inwardly from the fray or distal end 635 for a predetermined distance.

Moreover, and as shown in FIG. 65, the internal bore 640 and the internal threading 642 narrow toward the fray or distal end 635 of screw 630 in the area of the slots 643, 644, 645 and 646.

Figure 70:
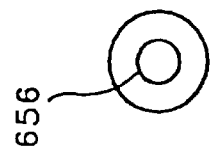
FIG. 70 is a right end elevational view of the driver illustrated in FIG. 68.
Figure 68:
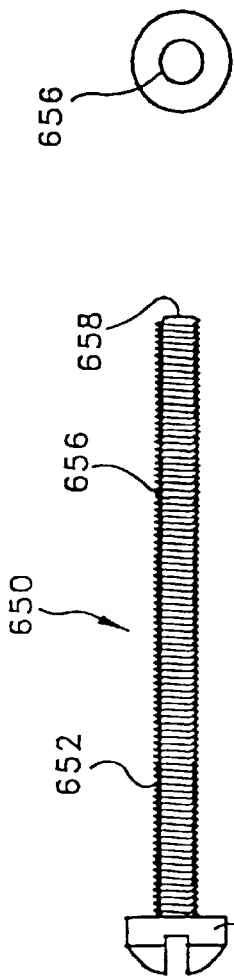
FIG. 68 is an elevational view of a driver used in combination with the compression screw assembly illustrated in FIGS. 65 through 67.
Figure 69:
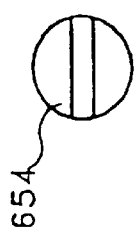
FIG. 69 is a left end elevational view of the driver illustrated in FIG. 68.

As mentioned above, the compression screw assembly 600 further includes a driver 650 to be arranged in combination with the screw 630. The driver 650 is illustrated in FIGS. 68, 69 and 70. Driver 650 includes a shank portion 652 and an enlarged headed portion 654. The shank portion 652 of driver 650 is provided with external threading 656 extending axially from a leading end 658 of the driver 650. The external threading 656 has a relatively fine pitch that corresponds to the internal threading 642 provided bore 640 of screw 630. The enlarged head portion 654 of driver 650 has a diameter slightly smaller than that which can be endwise accommodated within the socket 637 of screw 630. As will be appreciated from an understanding of the compression screw assembly 630, the length of the shank portion 652 is sufficient such that the distal or free end 658 operably extends to and through the slotted end of screw 630 when the head portion 654 bottoms at the floor 638 of socket 637.

As will be appreciated from an understanding of the compression screw assembly 600, the compression screw 630 is threaded into the anchor assembly 622 as shown in FIG. 64, to draw the guide 620 into compressive relationship relative to the anchor 622. Thereafter, the driver 650 is threaded into engagement with the internal threading 642 of screw 630. Notably, the outside diameter of the shank portion 632 of screw 630 is substantially constant as long as driver 650 remains out of engagement with the slotted end 635 of screw 630. Once the appropriate compression has been achieved between guide 620 and anchor 622, the driver 650 is further engaged with the compression screw as shown in FIG. 73. As a result, the slotted end 635 of screw 630 is expanded radially outwardly thus providing for a compressive fit which prevents the compression screw assembly 600 from rotating relative to the anchor 622 and thereby maintaining the compressive relationship between the guide 620 and anchor 622.

As mentioned above, and as schematically represented in FIG. 74, a series of screws 28 are used to fasten plate 32 of guide 20 to bone fragment 18. Another aspect of the present invention relates to a preferred form of construction for the screw 28 used to fasten the plate 32 of guide 20 to the bone fragment 18.

In the preferred embodiment, and as shown in FIG. 75, screw 28 comprises an elongated cannulated fastener 700 and a driver 702. As will be appreciated, fastener 700 is formed from a material that is biocompatible with bone tissue and includes a shank portion 710 and an enlarged head portion 712. The shank portion 710 of fastener 700 is provided with external threading 714 extending axially from a leading end 716 of the fastener 700. The external threading 714 has a pitch that promotes purchase and securement of the fastener 700 within the bone substance. The enlarged head portion 712 of fastener 700 is configured to cooperate with the shape of the throughhole 34 in the plate 32 of guide 20. In the illustrated embodiment, the head portion 712 of fastener 700 has a frusto-conical like configuration that cooperates with a countersunk configuration or recess in the throughhole 34 to secure the plate 32 to the bone 18. It will be appreciated, however, that shapes other than that shown for the head portion 712 and throughhole 34 would equally suffice without detracting or departing from the spirit and scope of the disclosure.

As shown in FIG. 76, a trailing end 718 of fastener 700 is preferably configured to releasably to accommodate a driving tool (not shown) capable of imparting turning movements to the fastener 700. In a preferred form, and as shown, the trailing end 718 of fastener 700 is configured with an elongated slot or opening 720. The slot 720 is configured to releasably accommodate a distal end of a driving tool. As will be appreciated, however, any suitable configuration including a socket would equally suffice for releasably accommodating a distal end of a driving tool without detracting or departing from the spirit and scope of the present invention.

Figure 79:
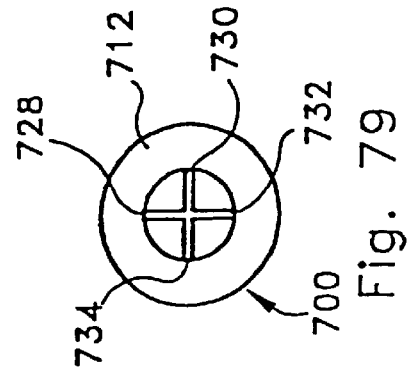
FIG. 79 is a right end view of the compression screw illustrated in FIG. 77.
Figure 77:
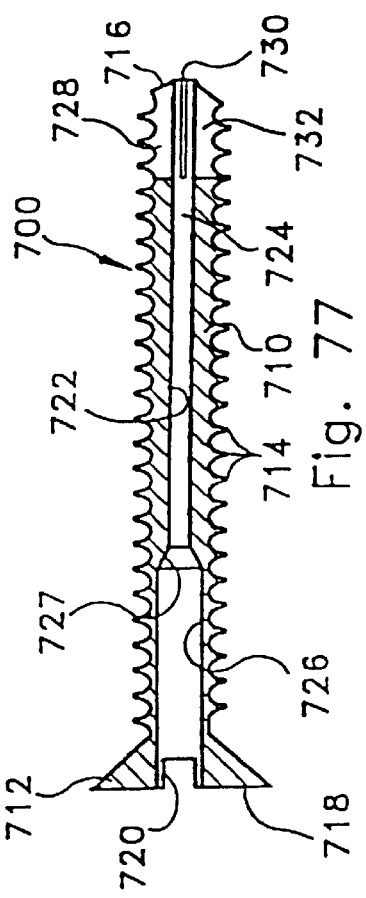
FIG. 77 is a sectional view of a compression screw illustrated in FIGS. 75 and 76 as taken along line 77—77 of FIG. 78.
Figure 78:
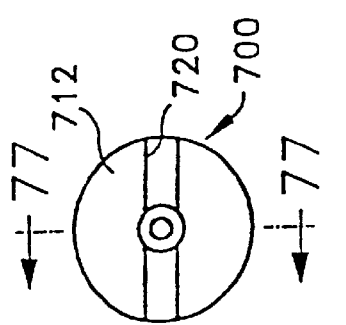
FIG. 78 is a left end view of the compression screw shown in FIG. 77.

The cannulated fastener 700 furthermore defines an elongated bore 722 that opens at opposite ends 716, 718 of fastener 700. As shown in FIGS. 76 and 77, the bore or opening 722 has a first section 724 opening to the first end 716 of fastener 700 and having a first diameter and a second counterbore portion 726 opening to the trailing or second end 718 of fastener 700 and having a second diameter. Notably, the diameter of bore 726 is larger than the diameter of bore or opening 722 and, thus, a radial wall or annular shoulder 727 is defined by the differences in diameters therebetween. As shown in FIGS. 77 and 79, the distal or leading end 716 of the fastener 700 is provided with a series of radial through slots 728, 730, 732 and 734 that are arranged in generally normal relation relative to each other and which extend axially inwardly from the first or distal end 716 of fastener 700 for a predetermined distance. As shown, and for purposes described hereinafter, the diameter of the first portion 724 of bore 722 narrows or is reduced in the area of the slots 728 through 734 while the outside diameter of the fastener remains substantially constant.

As will be appreciated from an understanding of this embodiment, the axial length of the shank portion 710 of fastener 700 is such that when the fastener is passed through the throughhole 34 in the plate 32 of guide 20 and secured within the bone 18, the axial lengthwise portion of the shank 710 with the slots formed therein will extend beyond the bone 18 by a distance equal to about the length of the slots 728 through 734. Of course, during surgery, a surgeon may have a collection of different fasteners to choose from; with each fastener having a different length such that a proper relationship of the fastener to bone thickness is readily obtainable for the surgeon.

Figure 82:
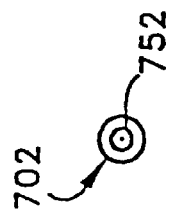
FIG. 82 is a right end elevational view of the driver illustrated in FIG. 80.
Figure 80:
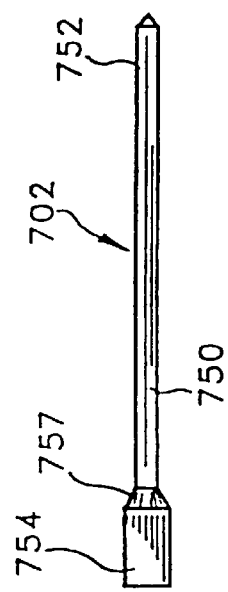
FIG. 80 is a side elevational view of a driver used in combination with the screw assembly illustrated in FIGS. 75 and 76.
Figure 81:
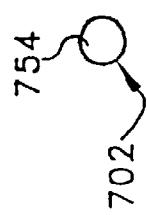
FIG. 81 is a left end elevational view of the driver illustrated in FIG. 80.

As mentioned above, this form of screw 28 further includes a driver 702 arranged in combination with fastener 700. A preferred form of driver 702 is illustrated in FIGS. 80 through 82. As shown, drive 702 preferably includes a one-piece member 750 formed from a material that is biocompatible with human bone tissue and substance. Driver member 150 includes a first section 752 with a substantially constant diameter along its length and an axially aligned second section 754 having a substantially constant diameter along its length. The second section 754 has a larger diameter than the first section 752 and, thus, a radial wall or annular should 757 is defined therebetween.

In the illustrated embodiment, the annular shoulder or annular wall 757 on the driver 702 generally corresponds to the radial wall or annular shoulder 727 defined by fastener 700. It is important to note, however, the axial length of the first section 752 extending between the radial wall or annular shoulder 757 and the free end of driver member 750 is generally equal to the distance separating the radial wall or annular shoulder 727 from the distal or free end 716 of fastener 700. Moreover, the first section 752 of driver 702 is sized to establish a sliding fit within the first section 724 of bore 722 defined by fastener 700. In a most preferred form of the invention, the second section 754 of driver 702 is sized to establish a sliding fit within the second section 726 of bore 722 defined by fastener 700.

Figure 83:
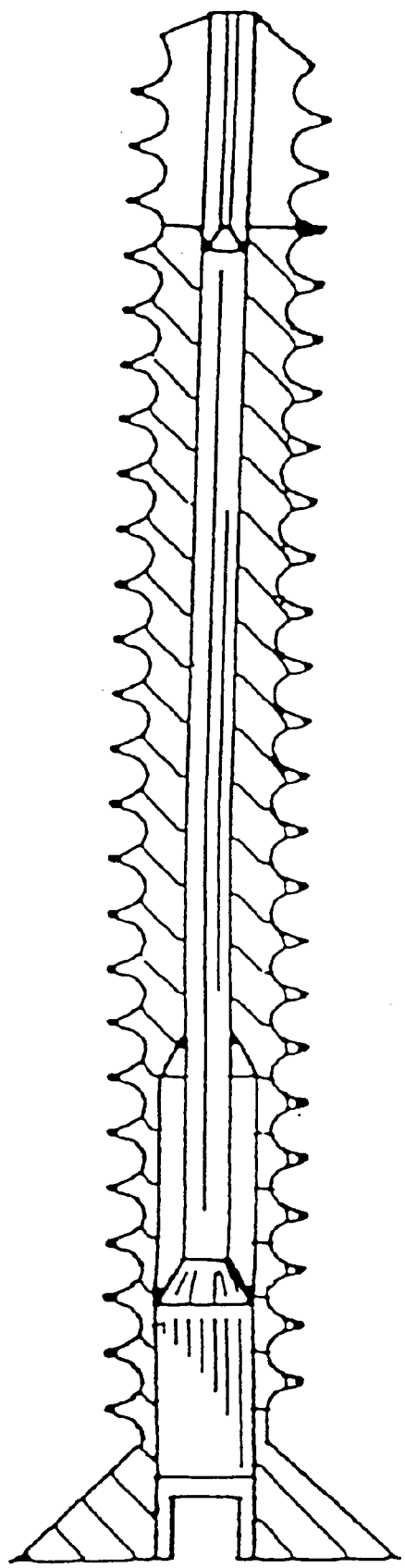
FIG. 83 is a view showing the driver partially arranged in operable association with the compression screw.

As will be appreciated from an understanding of the screw 28, and as shown in FIG. 75, the first or, forward end 716 of the fastener 700 is passed endwise through the throughbore 34 in plate 32 of guide 20 and the shank portion 710 is threaded into the bone 18 by turning the head portion 712. Ultimately, the head portion 712 will contact the plate 32 and draw the guide 620 into a secured relationship relative to the bone. At this point, the slotted free end of the fastener 700 will extend beyond the bone 18 on that side thereof opposite from the plate 32 of guide 20. Notably, as the fastener 700 is secured within the bone 18, the outside diameter of the shank portion 710 of screw 700 is substantially constant as long as the driver 702 remains out of engagement with the fastener 700. Once the appropriate securement has been achieved between guide 620 and cannulated fastener 700, the driver 702 is driven through the bore 722 of fastener 700 as shown in FIG. 83. When the driver 702 is fully inserted into the fastener 700, as when the shoulder 757 on the driver member 750 engages with the shoulder 727 on the fastener 700, the slotted end 716 of fastener 700 is expanded radially outwardly thus preventing inadvertent rotation of the fastener 700 thereby maintaining the secured relationship between the guide 20 and bone 18 as shown in FIG. 75.

Figure 84:
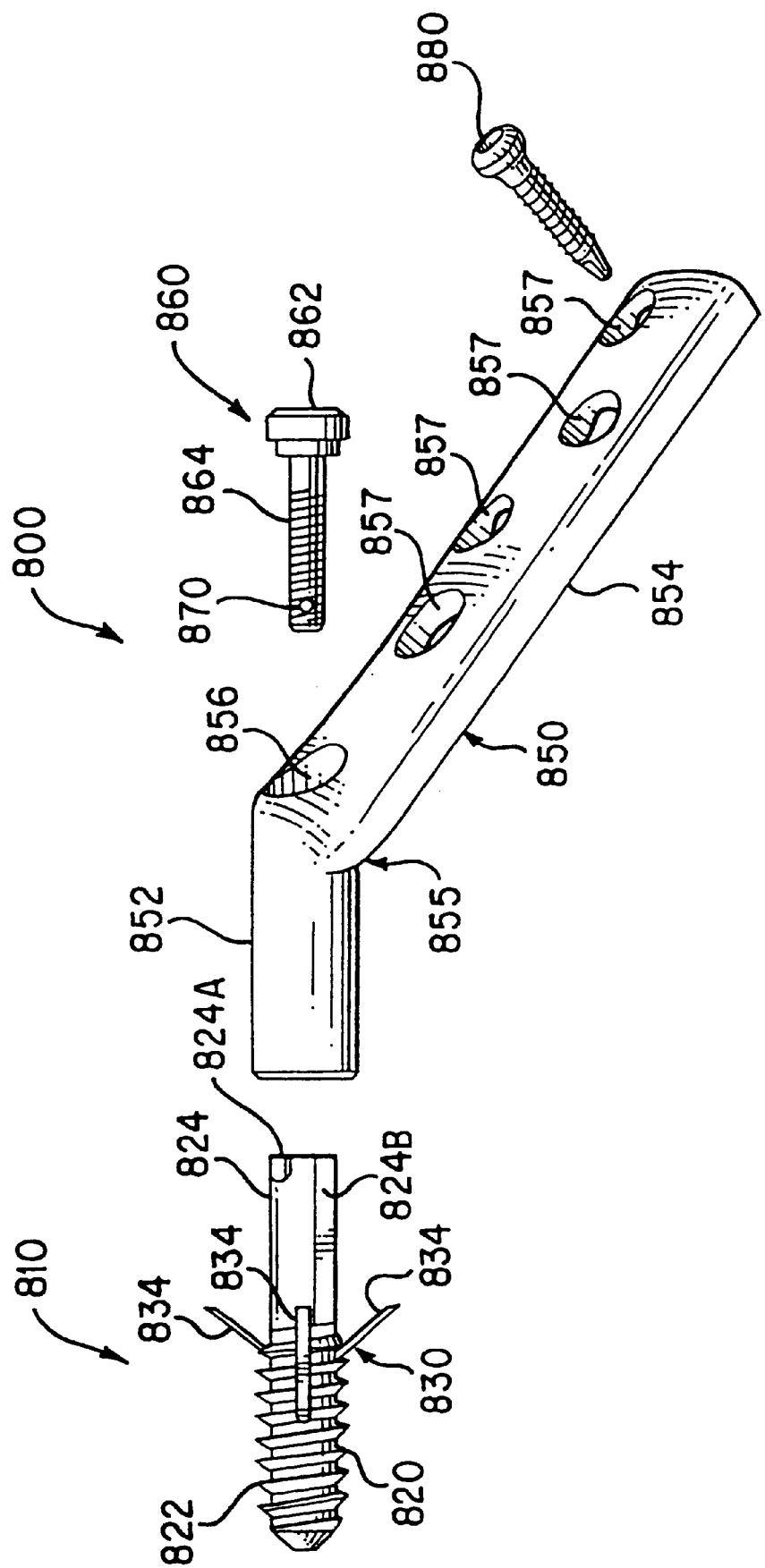
FIG. 84 is an exploded, perspective view of another alternative embodiment for a surgical fastener assembly in accordance with the principles of the present invention.

FIG. 84 illustrates an additional alternative embodiment for a surgical fastener assembly 800 in accordance with the principles of the present invention. As can be seen in FIG. 84, surgical fastener assembly 800 includes, as did previously disclosed embodiments, an anchor assembly 810, a guide 850, a fastener, or compression screw, 860 and screws 880, one of which is illustrated in FIG. 84. Surgical fastener assembly 800 is utilized in the same manner as are previously disclosed embodiments. A first portion 822 of anchor assembly 810 is threaded into a first bone portion and a second portion 824 of anchor assembly 810 is disposed through a second bone portion, where a fracture extends between the first bone portion and the second bone portion. Tangs 834 are extended from anchor assembly 810 where they extend into the first bone portion. Sleeve 852 of guide 850 is positioned around the second portion 824 of anchor assembly 810. Fastener 860 is inserted into and through guide 850 where fastener 860 threadedly engages with anchor assembly 810 and operably couples to guide 850. By threading fastener 860 into anchor assembly 810, guide 850, which is attached to the second bone portion, is drawn into a compressive relationship with anchor assembly 810, thus compressing the first bone portion with the second bone portion. Further description of the operation and use of surgical fastener assembly 800 will be provided later in this specification.

Figure 85:
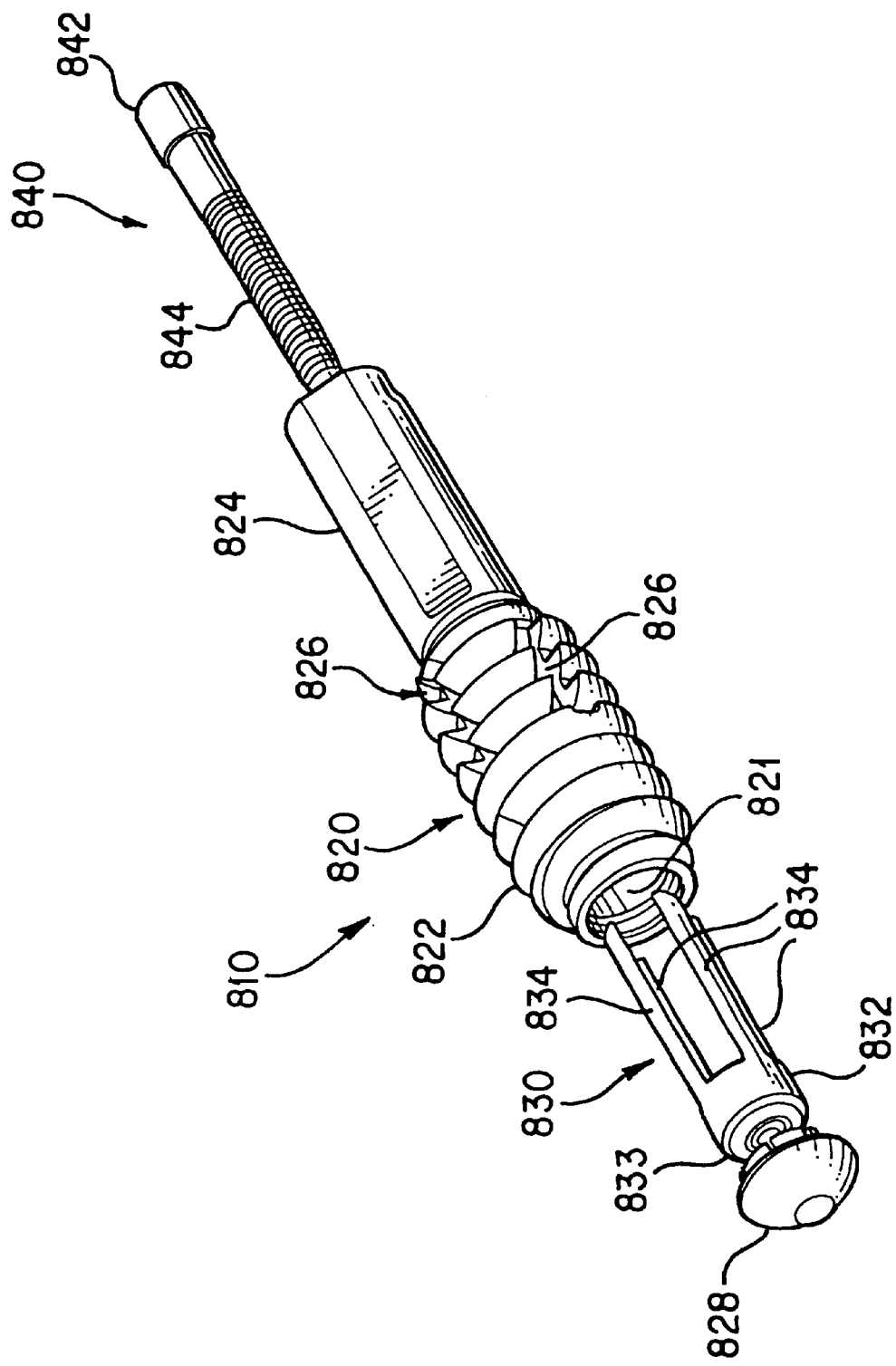
FIG. 85 is an exploded, perspective view of the anchor assembly of FIG. 84.

As will also be further described in additional detail, anchor assembly 810 includes an anchor 820, a tang, or pin, assembly 830, and an actuator 840, which is not visible in FIG. 84 but which can be seen in FIG. 85.

In further describing guide 850, as can be seen in FIG. 84 and as was described in connection with other disclosed embodiments, guide 850 includes a sleeve 852 and a plate 854. Sleeve 852 is located at a first end 855 of plate 854. Plate 854 includes a plurality of screw apertures 857 through which are received screws 880 which serve to secure plate 854 to the second bone portion. Sleeve 852 defines a longitudinal bore within it. The second unthreaded portion 824 of anchor 820, which is disposed within the second bone portion, is received within the bore of sleeve 852.

As can be seen in FIG. 84, a driving tool receiving slot 824A is provided within second portion 824 of anchor 820. Driving tool receiving slot 824A receives within it structure of a driving tool that is used to rotate anchor assembly 810, and thus anchor 820, in order to thread anchor assembly 810 into the first bone portion.

As can also been seen in FIG. 84, second portion 824 of anchor 820 also includes two flats 824B (only one of which is visible in FIG. 84) on the outside circumference of second portion 824. The flats 824B are on opposed sides of second portion 824 and are thus 180° from each other around the circumference of second portion 824. Each flat 824B provides a non-conforming surface (with respect to the circularly-shaped non-flats portion of the circumference of second portion 824) on the circumference of second portion 824. The internal bore of sleeve 852 of guide 850 is formed in a complementary configuration with respect to second portion 824 such that, as second portion 824 is received within sleeve 852, the flats 824B interact with the complementary surfaces defining the bore of sleeve 852 to prevent rotation of anchor assembly 810 within sleeve 852. Two flats 824B are provided 1800 from each other in order to provide for ease of aligning second portion 824 for positioning within sleeve 852. If only one flat was provided, second portion 824 could only be positioned in one orientation such that it could be received within sleeve 852. However, the present invention can be practiced by utilizing various quantities and configurations for flats 824B. Additionally, the present invention is not limited to only utilizing the above-described structure for preventing rotation of anchor assembly 810 within sleeve 852. Many other configurations for mating structures on the anchor assembly and sleeve could be utilized.

Guide 850 also defines a fastener aperture 856 through which fastener 860 extends when it is threadedly mated with anchor assembly 810. As was disclosed when discussing previous embodiments, when fastener 860 is inserted through fastener aperture 856, the threaded shank 864 of fastener 860 engages with internal threading that is included within second portion 824 of anchor 820. The head 862 of fastener 860 engages with the structure of guide 850 that defines fastener aperture 856 such that as fastener 860 is threaded within second portion 824 of anchor 820, guide 850 is drawn into a compressive relationship with anchor assembly 810.

As will be further discussed later in this specification, fastener 860 includes a retainer 870 on its threaded shank portion 864. When fastener 860 has been threaded into anchor assembly 810, retainer 870 locks together fastener 860 and anchor assembly 810 such that, in the absence of a force applied specifically to withdraw fastener 860 from anchor assembly 810, fastener 860 will not back-out of anchor assembly 810. Inadvertent backing-out of fastener 860 from anchor assembly 8 10 would lessen the compressive force which joins the first bone portion to the second bone portion.

Figure 86:
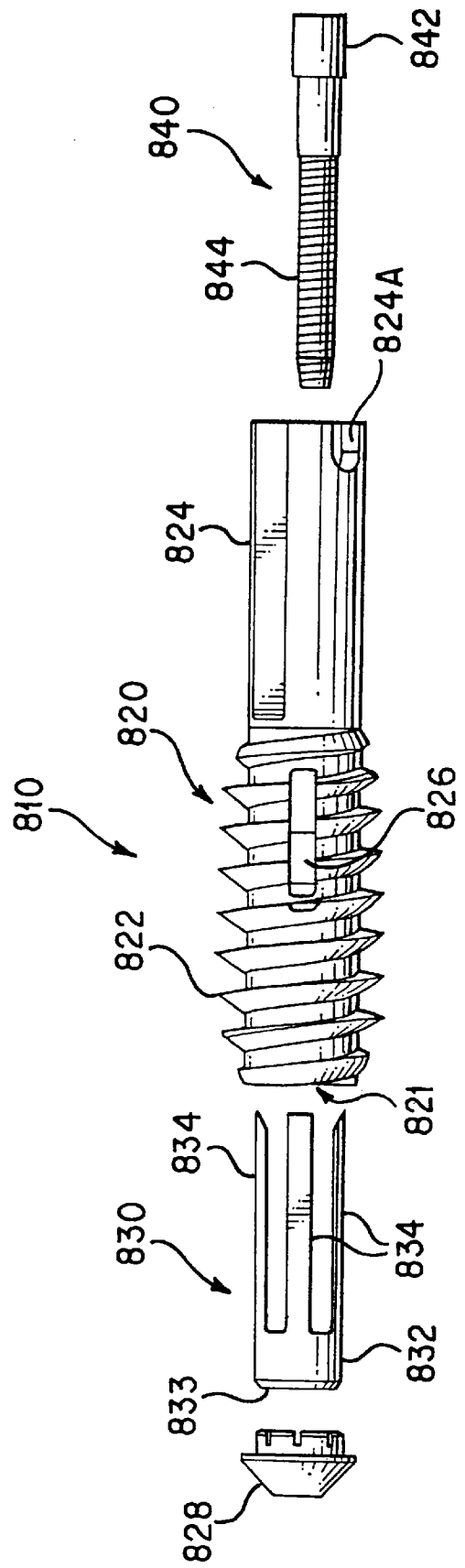
FIG. 86 is an exploded side view of the anchor assembly of FIG. 85.

FIGS. 85 and 86 illustrate anchor assembly 810. As was described previously, anchor assembly 810 includes anchor 820, tang assembly 830, and actuator 840. Each of these components will now be described in further detail. Anchor 820 is comprised of an elongated structure that defines a hollow bore which extends longitudinally through anchor 820. Anchor 820 includes a first externally threaded portion 822 and a second portion 824. As was explained earlier, first externally threaded portion 822 is threaded into the first bone portion and second portion 824 is disposed within the second bone portion. First portion 822 of anchor 820 includes an open end 821, through which, as will be explained, is inserted tang assembly 830. First portion 822 also defines a plurality of slots 826 that extend completely through the structure of anchor 820 such that openings exist within first portion 822 that extend from the bore of anchor 820 through the exterior structure of anchor 820. There is a slot 826 provided in anchor 820 for each of the tangs 834 that are included in tang assembly 830.

Tang assembly 830 is comprised of a circular base portion 832 and a plurality of tangs 834 which extend from base 832. Base 832 defines a bore that extends therethrough which is internally threaded. Tangs 834 extend from base 832 and, whereas the illustrated embodiment includes four tangs, any number of tangs can be utilized in the present invention. As can be understood, if other than four tangs were utilized, a like number of slots 826 would be provided in anchor 820.

Figure 88:
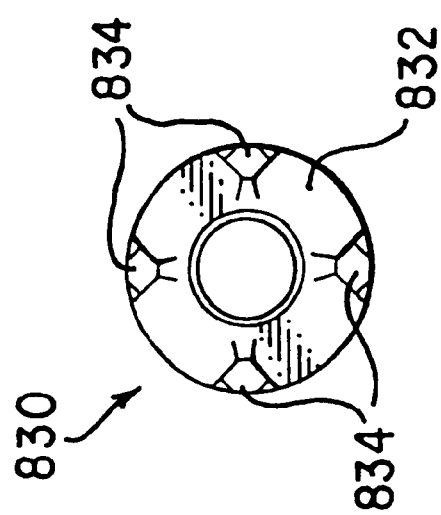
FIG. 88 is a front view of the tang assembly.
Figure 87:
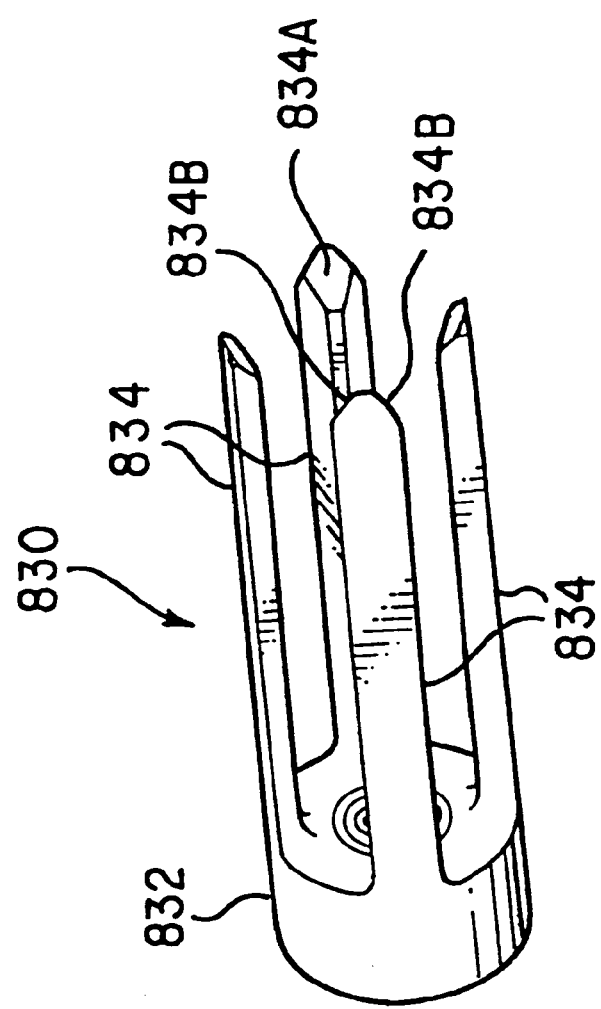
FIG. 87 is a perspective view of the tang assembly of FIGS. 85 and 86.

FIGS. 87 and 88 further illustrate tang assembly 830. As can be seen, each tang 834 includes an internally chamfered surface 834A and outside chamfered surfaces 834B. The operation of tang assembly 830 will be described later in this specification.

Tang assembly 830 is received within the bore that is defined by anchor 820. As tang assembly 830 is positioned within anchor 820, each tang 834 is positioned within one of the slots 826 that are included in anchor 820. The structure of anchor 820 that defines slots 826 may extend slightly within the bore defined by anchor 820 such that as the tangs 834 are positioned within the slots 826, the tang assembly 830 is not able to rotate about its longitudinal axis within anchor 820. The tang assembly 830 is not able to rotate within anchor 820 due to the interaction of the structure that defines slots 826 with tangs 834. The purpose of not allowing tang assembly 830 to rotate within anchor 820 will become clear later in this specification.

The present invention is not limited to any particular methodology for preventing rotation of tang assembly 830 within anchor 820. Any number of different structural configurations could be provided within the bore of anchor 820. Additionally, tangs 834 could be formed such that their ends could extend slightly up into slots 826 in order to prevent rotation. The tangs 834 would not yet extend completely up through slots 826 but yet would extend into slots 826 a sufficient distance such that they would contact the structure that defines the slots to prevent their rotation.

After tang assembly 830 has been inserted within anchor 820, cap 828 is fitted within open end 821 of anchor 820. Cap 828 may be snap-fitted within open end 821. Cap 828 serves to enclose first portion 822 of anchor 820 for purposes of retaining tang assembly 830 within anchor 820 when, for example, actuator 840 is not engaged with tang assembly 830, preventing material, e.g. bone particles, from entering the internal bore of anchor 820 as the anchor assembly 810 is threaded into the first bone portion, and for providing structure to allow anchor assembly 810 to be more easily threaded into the first bone portion.

After tang assembly 830 has been inserted within anchor 820, actuator 840 is positioned within anchor 820. Actuator 840 includes a head portion 842 and a partially threaded shank portion 844. Head portion 842 includes a bore along its longitudinal axis such that, as can be understood, a driving tool may be received within the bore in order to rotate actuator 840. Thus, for example, a hexagonally shaped bore may be provided that would receive within it a hexagonally shaped driving tool. As will be further explained, actuator 840 is inserted within anchor 820 where threaded shank portion 844 is threaded into the internally threaded bore that is defined by base 832 of tang assembly 830. Thus, actuator 840 is not threaded into the bore defined by anchor 820, but rather, is threaded into the bore defined by base 832 of tang assembly 830.

Figure 89:
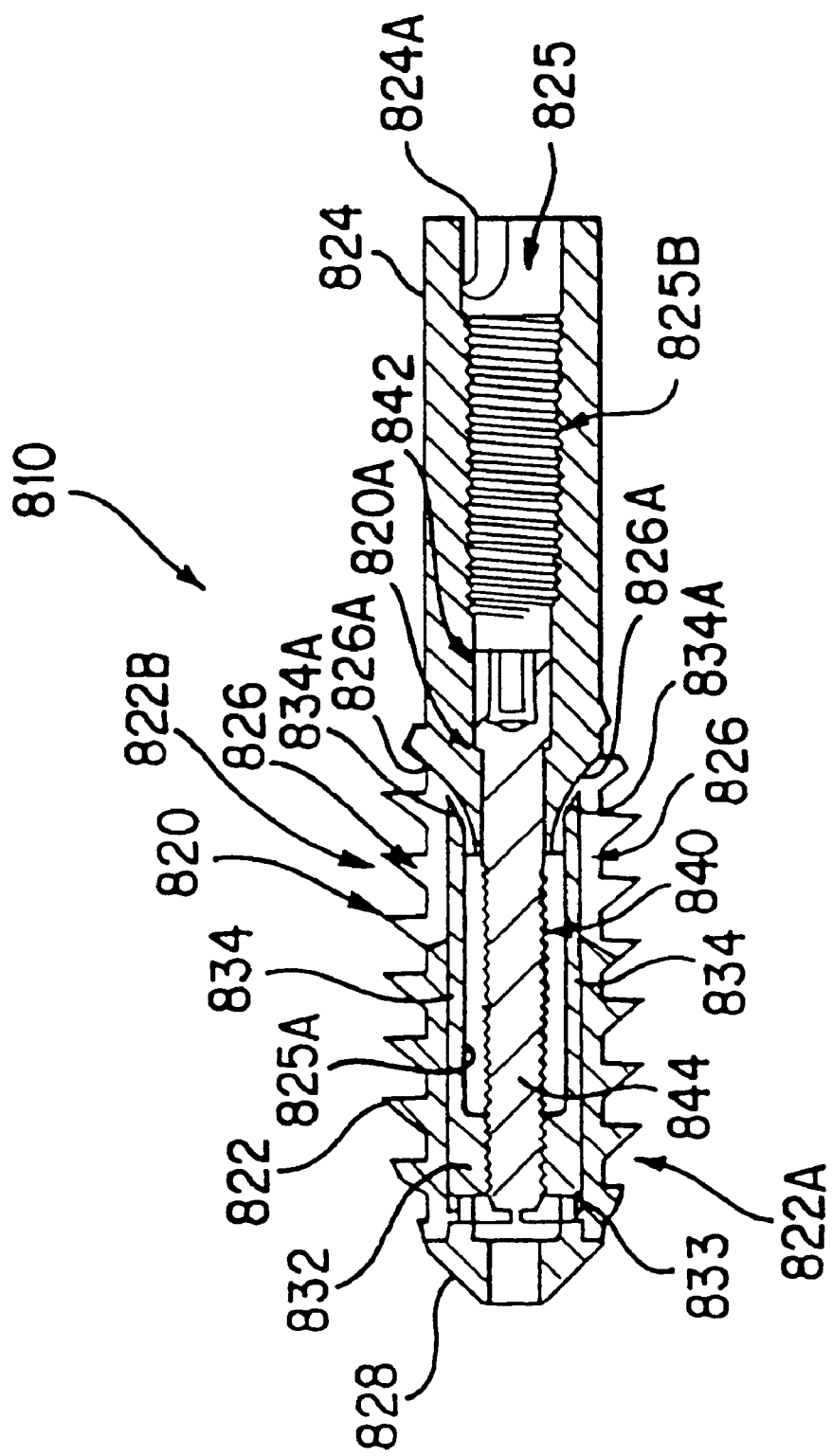
FIG. 89 is a cross-sectional view of the anchor assembly with the tangs in a retracted position.

The operation of anchor assembly 810 will now be described in further detail. FIG. 89 is a cross-sectional view of anchor assembly 810 where tangs 834 are in a retracted position within anchor 820. As can be seen in FIG. 89, anchor 820 defines a bore 825 within it that includes a larger diameter portion 825A; which is unthreaded and which receives within it tang assembly 830, and a smaller diameter portion 825B, a portion of which is threaded and which receives within it the threaded shank portion 864 of compression screw 860. As can be seen, tang assembly 830 has been positioned within bore 825A of anchor 820. Base portion 832 of tang assembly 830 is located at a first end 822A of bore 825A. When base 832 is in this position tangs 834 are retracted within anchor 820.

As can also be seen in FIG. 89, actuator 840 is positioned within bore 825 of anchor 820. The threaded shank portion 844 of actuator 840 extends within bore portion 825A and the head 842 of actuator 840 is received within bore portion 825B. As can be seen, a shoulder 820A is formed within anchor 820 which engages with head 842 of actuator 840. Shoulder 820A restricts actuator 840 from being inserted further within bore 825 beyond the point at which shoulder 820A contacts head 842. As can be seen, threaded shank portion 844 has been threaded into base 832 of tang assembly 830.

In FIG. 89, each tang 834 is positioned within, and consequently aligned with, a slot 826. However, in this position for tang assembly 830, tangs 834 do not extend up through slots 826 and thus do not extend beyond the outer surface of anchor 820. As can also be seen in FIG. 89, a portion of the structure of anchor 820 that defines slots 826 includes a slanted or curved surface 826A. Curved surface 826A defines a rear end of each slot 826. As can also be seen, the internally chamfered surface 834A of each tang 834 is oriented such that it faces curved surface 826A.

FIGS. 90 and 91 illustrate anchor assembly 810 in a configuration where tangs 834 have been moved to a position where they extend from anchor 820. In order to extend tangs 834 from anchor 820, a user would insert a driver tool through bore 825 of anchor 820 and engage the driver tool with head 842 of actuator 840. The user would rotate, in a clockwise direction, actuator 840 within anchor 820. Thus, as can be understood, actuator 840 is free to rotate within bore 825 of anchor 820. Since threaded shank portion 844 of actuator 840 is threaded into base 832 of tang assembly 830, as actuator 840 is rotated in a clockwise direction, base 832, and consequently tang assembly 830, is moved up the threaded shank 844 of actuator 840 and toward the second end 822B of bore 825A. As can be understood, as tang assembly 830 is moved toward second end 822B, the chamfered ends 834A of tangs 834 will engage with the slanted surfaces 826A of each slot 826; Thus, due to the complimentary surfaces of tangs 834 and slots 826, as tang assembly 830 is moved along threaded shank 844 of actuator 840, tangs 834 will be moved up through slots 826 and be extended from anchor 820.

In order for tangs 834 to be able to extend up through slots 826, tangs 834 are manufactured from a deformable material. Thus, tangs 834 may be formed from stainless steel or any other material that is able to deform as tangs 834 are moved up through slots 826. Tangs 834 may be formed from any of a variety of materials with a consideration being that tangs 834 must be deformable such that they can extend outward from anchor 820. However, tangs 834 must be strong enough such that they can provide for purchase between anchor 820 and the first bone portion. Thus, as described above, tangs 834 are not pre-formed into a configuration where, when they are moved within anchor 820, they extend from anchor 820 because of their pre-formed configuration, e.g., in an arcuate shape. Rather, in the present embodiment, tangs 834 are formed of a deformable material and the movement of tangs 834 within anchor 820 form the tangs such that they are able to extend from anchor 820.

As can also be seen in FIG. 91, structure of anchor 820 that defines bore 825 engages with base 832 at second end 822B of bore 825A such that tang assembly 830 is not able to be moved further within bore 825A beyond second end 822B. This will prevent tangs 834 from being extended too far through slots 826, which could result in the tangs 834 not being shaped in a desired form when extended from anchor 820. For example, if base 832 was moved too far within bore 825, tangs 834 could be bent backwards and thus not achieve the desired anchoring strength within the first bone portion. Additionally, if base 832 was moved too far within bore 825, base 832 could become threadedly disengaged from actuator 840. However, in the disclosed embodiment this will not occur because base 832 defines a bore with a diameter that is smaller than the diameter of the unthreaded portion of shank 844. Thus, the base 832 of tang assembly 830 cannot travel on shank 844 beyond the threaded portion of shank 844.

Thus, as explained above, clockwise rotation of actuator 840 within anchor 820 moves tang assembly 830 within anchor 820. As base 832 of tang assembly 830 is moved toward second end 822B of bore 825A, tangs 834 engage with the curved surfaces 826A that define the rear of slots 826 in anchor 820 such that tangs 834 will extend out through slots 826 and from anchor 820. The interaction of tangs 834 and curved surfaces 826A deform tangs 834 such that they extend from anchor 820 and are inserted within the first bone portion.

FIG. 92 illustrates tang assembly 830 as it would be configured after it has been moved within anchor 820 to extend tangs 834 from anchor 820. Whereas it was not discussed previously when describing tang assembly 830, base 832 also includes a chamfered surface 833. Chamfered surface 833 may be seen in FIGS. 85 and 86 and the purpose of chamfered surface 833 is to engage with cap 828 to aid in preventing end cap 828 from being dislodged during tang retraction within anchor 820, as will be explained below. Thus, chamfered surface 833 wedges cap 828 into place within anchor 820.

In order to retract tangs 834 back within anchor 820 after the tangs have been deployed from the anchor as described above, the operator would rotate actuator 840 in a counter-clockwise direction. Thus, as can be understood, since tangs 834 of tang assembly 830 are embedded within the first bone portion, as actuator 840 is rotated counter-clockwise within anchor 820, actuator 840 will be backed-out of base 832. Thus, actuator 840 can be entirely removed from tang assembly 830 and, consequently, from bore 825 of anchor 820. In order to retract tangs 834 into anchor 820, one possible methodology is to drive base 832 back toward first end 822A of bore 825A. One possible method for driving base 832 back toward first end 822A is to insert a tool within bore 825 that would engage with base 832 and apply sufficient force to base 832 to drive base 832 toward first end 822A such that tangs 834 are retracted back into anchor 820. The driving tool is not required to be threaded into base 832, rather, it is only necessary to engage with base 832 such that sufficient force may be applied to base 832 to force it toward first end 822A. As base 832 is driven toward first end 822A, tangs 834 will be withdrawn from the first bone portion and retracted back through slots 826. Thus, as tangs 834 are drawn back through slots 826, tangs 834 will again deform such that they ,will return substantially to their original configuration such that they can once again be received within bore 825A of anchor 820. As such, tangs 834 are able to withstand at least one complete extension and retraction cycle without materially failing.

It is possible to utilize actuator 840 as the driving tool for forcing base 832 of tang assembly 830 toward first end 822A of bore 825A, as described above. After actuator 840 has been completely retracted from base 832 by rotating actuator 840 counter-clockwise, actuator 840 may be re-inserted within bore 825 such that it engages with base 832. Actuator 840 does not necessarily have to threadedly engage with base 832, but rather, only needs to structurally engage with base 832 such that force can be applied to base 832 in order to force it back toward first end 822A. The present invention is not limited to any particular engagement methodology for engaging a driver tool with base 832 to drive base 832 toward first end 822A. A variety of engagement methodologies may be utilized. All that is required is that a driving tool, which could be actuator 840, engage with base 832 such that sufficient force may be applied to base 832 to move it within bore 825 toward first end 822A. Thus, by utilizing the above-described methodology for retracting tangs 834 back within anchor 820, threaded engagement is not required between a driving tool and each individual tang.

Whereas a methodology for retracting tangs 834 within anchor 820 has been described above, the present invention is not limited to utilizing only this methodology. For example, if sufficient force is applied to actuator 840, counter-clockwise rotation of actuator 840, while threaded shank portion 844 is still threadedly engaged with base portion 832, could serve to retract tangs 834 within anchor 820. In this manner, counter-clockwise rotation of actuator 840 within base 832 would drive base 832 toward first end 822A of bore 825A which would in-turn retract tangs 834 within anchor 820.

Figure 93:
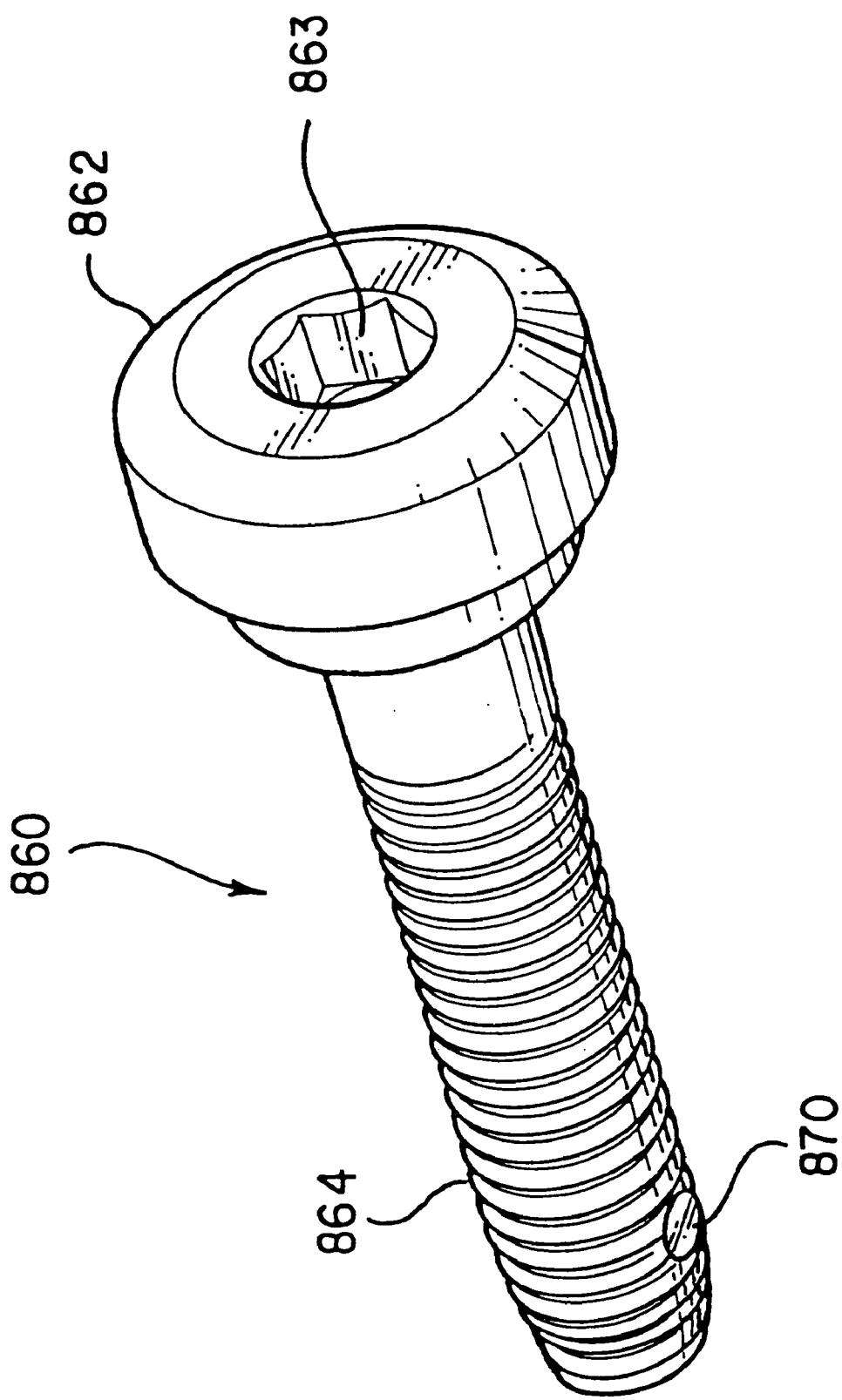
FIG. 93 is a perspective view of the compression screw with a retainer disposed on the outer surface of the screw.

FIG. 93 illustrates an embodiment for fastener, or compression screw, 860. As was mentioned previously, compression screw 860 includes a head portion 862 and a threaded shank portion 864. Head portion 862 defines within it a hexagonally shaped bore 863 that receives a driving tool within it. Also as was described previously, threaded shank portion 864 extends through fastener aperture 856 in guide 850 and is threadedly received within second portion 824 of anchor 820. Head portion 862 operably engages with guide 850 such that as shank portion 864 is further threaded into second portion 824 of anchor 820, anchor assembly 810 and guide 850 are brought into a compressive relationship with each other thus joining the first bone portion with the second bone portion.

As was mentioned previously, included on threaded shank portion 864 of fastener 860 is a retainer 870. Retainer 870 is formed as an ultrahigh molecular weight polyethylene (UHMWPE) insert, or any other material with like properties, and is positioned within a bore that is included in threaded shank portion 864. A portion of retainer 870 extends beyond the outer circumference of threaded shank portion 864. As threaded shank portion 864 is threaded into anchor assembly 810, it can be understood that retainer 870 will be compressed between the structure defining the bore in second portion 824 of anchor 820 and shank portion 864 of fastener 860. Since retainer 870 is formed of a deformable material, it will deform slightly such that shank portion 864 can be threaded into anchor assembly 810, however, it will provide additional frictional force between anchor assembly 810 and shank portion 864 such that, in the absence of a force specifically applied to retract fastener 860 from anchor assembly 810, fastener 860 will not back-out from anchor assembly 810. Thus, retainer 870 provides a self-locking capability for fastener 860 within anchor assembly 810. Examples of other deformable materials that may be utilized for retainer 870 are nylon, acetal, polytetrafluoroethylene (PTFE), and polyetheretherketone (PEEK). However, again, the present invention is not limited to only utilizing these exemplary deformable materials for retainer 870.

As can be understood from the above description, surgical fastener assembly 800 is utilized to join a first bone portion to a second bone portion where there is a fracture therebetween. In utilizing surgical fastener assembly 800, a user would thread externally threaded portion 822 of anchor 820 into the first bone portion. Guide 850 is secured to the second bone portion. Second portion 824 of anchor 820 is received within sleeve 852 of guide 850. As explained previously, anchor assembly 810 is prevented from rotating within sleeve 852 by the interaction of flats 824B and the internal structure defining the bore within sleeve 852.

When anchor 820 is threaded into the first bone portion, tangs 834 are in a retracted position within anchor 820. Actuator 840 is threadedly engaged with tang assembly 830. A driving tool is inserted through guide 850, which has been secured to the second bone portion, and through second portion 824 of anchor 820, which has been received within sleeve 852 of guide 850, to engage with actuator 840 to rotate actuator 840 in a clockwise direction. This clockwise rotation of actuator 840 will move tang assembly 830 within anchor 820 and will extend tangs 834 from anchor 820, as described previously. Tangs 834 embed themselves within the first bone portion such that the purchase between anchor 820 and the first bone portion is enhanced.

After tangs 834 have been extended from anchor 820, fastener 860 is inserted through fastener aperture 856 where fastener 860 is threadedly received within second portion 824 of anchor 820. Head 862 of fastener 860 operably engages with guide 850. Thus, as fastener 860 is further threaded into anchor assembly 810, guide 850 is drawn into a compressive relationship with anchor assembly 810 such that the second bone bone portion is joined to the first bone portion.

In order to remove the surgical fastener assembly 800 from the body of the patient, a user would decouple fastener 860 from anchor assembly 810. Guide 850 can then be removed from the second bone portion by removing screws 880 from the second bone portion. In order to remove anchor assembly 810, tangs 834 are retracted within anchor 820 by any of the methods described previously. Once tangs 834 have been retracted into anchor 820, anchor assembly 810 may be unthreaded from the first bone portion.

The disclosed embodiments are illustrative of the various ways in which the present invention may be practiced. Other embodiments can be implemented by those skilled in the art without departing from the spirit and scope of the present invention.

What is claimed is:

1. A surgical apparatus for coupling first and second bone portions across a fraction therebetween, comprising:
    an anchor, the anchor including a first externally threaded portion disposed in the first bone portion and a second portion which is at least partially disposed in the second bone portion;
    a pin operably associated with the first portion of the anchor, wherein when the pin is in a retracted position the pin is disposed within the anchor and wherein when the pin is in an extended position at least a portion of the pin extends outward from the anchor;
    a slide, the slide disposed within a bore of the anchor and connected to the pin;
    a guide, the guide adapted to be fixedly secured to the second bone portion and including a sleeve, the second portion of the anchor received within the sleeve; and
    a fastener, the fastener including a head portion and an externally threaded shank portion wherein the shank portion threadedly engages with the anchor and the head portion operably engages with the guide.

2. The surgical apparatus of claim 1 wherein the pin has an arcuate configuration.

3. The surgical apparatus of claim 1 wherein the pin extends from a base, the base defining an internally threaded bore and the base movably disposed within the first portion of the anchor.

4. The surgical apparatus of claim 3 wherein the slide is externally threaded along a first portion thereof and wherein the first portion of the slide is threadedly coupled to the internally threaded bore of the base.

5. The surgical apparatus of claim 1 wherein a plurality of pins are operably associated with the first portion of the anchor.

6. A surgical apparatus comprising:
    an anchor, the anchor including external threading extending along a first portion thereof and the anchor defining a longitudinal bore and at least one slot;
    pin operably associated with the first portion of the anchor, wherein when the pin is in a retracted position the pin is disposed within the longitudinal bore of the anchor and wherein when the pin is disposed within the longitudinal bore of the anchor and wherein when the pin is in an extended position at least a portion of the pin extends outward from the anchor through the slot;

a slide, the slide disposed within the bore of the anchor and connected to the pin;

a guide, the guide adapted to be fixedly secured to the second bone portion, a sleeve, a second portion of the anchor received within the sleeve; and a fastener, the fastener including a head portion and an externally threaded shank portion wherein the shank portion threadedly engages with the anchor and the head portion operably engages with the guide.

7. The surgical apparatus of claim 6 wherein the pin has an arcuate configuration.

8. The surgical apparatus of claim 6 wherein the pin extends from a base, the base defining an internally threaded bore and the base movably disposed within the longitudinal bore of the anchor.

9. The surgical apparatus of claim 8 wherein the slide is externally threaded along a first portion thereof and wherein the first portion of the slide is threadedly coupled to the internally threaded bore of the base.

10. The surgical apparatus of claim 6 wherein the pin is formed from a deformable material.

11. The surgical apparatus of claim 6 further comprising a retainer, at least a portion of the retainer positioned between structure defining the longitudinal bore of the anchor and the fastener.

12. The surgical apparatus of claim 6 wherein the retainer is inserted within the fastener and wherein the retainer is formed of a deformable material.

13. The surgical apparatus of claim 6, wherein the slide defines a pair of guide slots.

14. The surgical apparatus of claim 13, further comprising a pair of guide keys extending along a lengthwise portion of the counterbore defined by the anchor, wherein the pair of guide keys are radially offset from the pair of guide slots.

* * * * *